US008680139B2

(12) United States Patent
Cao et al.

(10) Patent No.: US 8,680,139 B2
(45) Date of Patent: Mar. 25, 2014

(54) ANTI-NEOPLASTIC COMPOUNDS, COMPOSITIONS AND METHODS

(75) Inventors: Ping Cao, Savoy, IL (US); Joseph Weinstock, Wayne, PA (US); William D. Kingsbury, Wilmington, NC (US); Craig A. Leach, Ardmore, PA (US); Suresh Kumar Kizhakkethil-George, Downingtown, PA (US); Benjamin Nicholson, Merion Station, PA (US)

(73) Assignee: Progenra, Malvern, PA (US)

( * ) Notice: Subject to any disclaimer, the term of this patent is extended or adjusted under 35 U.S.C. 154(b) by 0 days.

(21) Appl. No.: 13/262,422

(22) PCT Filed: Mar. 31, 2010

(86) PCT No.: PCT/US2010/029358
§ 371 (c)(1),
(2), (4) Date: Jan. 17, 2012

(87) PCT Pub. No.: WO2010/114881
PCT Pub. Date: Oct. 7, 2010

(65) Prior Publication Data
US 2012/0114765 A1 May 10, 2012

Related U.S. Application Data

(60) Provisional application No. 61/165,728, filed on Apr. 1, 2009, provisional application No. 61/165,713, filed on Apr. 1, 2009.

(51) Int. Cl.
*A61K 31/381* (2006.01)
*C07D 333/18* (2006.01)

(52) U.S. Cl.
USPC .............. 514/445; 549/29; 549/62; 549/63; 514/430; 514/438

(58) Field of Classification Search
USPC .............. 549/29, 62, 63; 514/430, 438, 445
See application file for complete search history.

(56) References Cited

U.S. PATENT DOCUMENTS

| 4,451,660 | A | 5/1984 | Dolman et al. | |
|---|---|---|---|---|
| 4,649,154 | A | 3/1987 | Dolman et al. | |
| 4,994,485 | A | 2/1991 | Dolman et al. | |
| 7,910,595 | B2 * | 3/2011 | Betebenner et al. | 514/264.11 |
| 8,236,950 | B2 * | 8/2012 | Betebenner et al. | 544/251 |
| 2006/0217381 | A1 | 9/2006 | Paulus | |
| 2007/0032499 | A1 | 2/2007 | Guedat et al. | |
| 2007/0212712 | A1 | 9/2007 | Ai et al. | |
| 2008/0103149 | A1 | 5/2008 | Guedat et al. | |

FOREIGN PATENT DOCUMENTS

| EP | 0 031 173 | 7/1981 |
|---|---|---|
| GB | 1 459 571 | 12/1976 |
| GB | 1 577 743 | 10/1980 |
| JP | 3-133975 A | 6/1991 |
| JP | 4-021677 A | 1/1992 |
| WO | 2004/009023 A2 | 1/2004 |
| WO | 2005/066152 A1 | 7/2005 |
| WO | 2005/070916 A1 | 8/2005 |
| WO | 2007/016338 A2 | 2/2007 |

OTHER PUBLICATIONS

Betebenner et al (2008): STN International HCAPLUS database, Columbus (OH), accession No. 2008: 1339253.*
Baxter et al (2006): STN International HCAPLUS database, Columbus (OH), accession No. 2006: 699970.*
Banks et al (1982): STN International HCAPLUS database, Columbus (OH), accession No. 1982: 455685.*
Dolman et al (1984): STN International HCAPLUS database, Columbus (OH), accession No. 1984: 454909.*
Balint, E. et al., "Mdm2 binds p73a without targeting degradation", Oncogene, 18: 3923-3929 (1999).
Brooks, C.L. et al., "The p53-Mdm2-HAUSP complex is involved in p53 stabilization by HAUSP", Oncogene, 26: 7262-7266 (2007).
Caxapob, B.H., Khimicheskaya Tekhnologiya, 50: 93-96 (2007).
Chauhan, D. et al., "Deubiquitylating Enzyme USP-7, a Novel Therapeutic Target in Multiple Myeloma", Abstract No. 610, 51st ASH Annual Meeting and Exposition, New Orleans, LA, Dec. 7, 2009.
Colland, F., "Small-molecule inhibitor of USP7/HAUSP ubiquitin protease stabilizes and activated p53 in cells", Mol. Cancer Ther., 8(8): 2286-2295 (2009).
Consiglio, G., "Aromatic nucleophilic substitution reactions of some 3-nitro-2-p-nitro-phenoxy-5-X-thiophenes with substituted anilines in methanol", J. Chem. Research (S), 266-267 (2002).
Consiglio, G., "Linear Free Energy Relationships in the Thiophen Series. Part 2. The Kinetics of the Reactions of Some 2-Bromo-3-nitro-5-X-thiophens with Substituted Anilines in Methanol", J. Chem. Soc., Perkin Transactions 2: Physical Organic Chemistry, 2: 388-92 (1981).
Consiglio, G. et al., "Catalysis in aromatic nucleophilic substitution. Part 12. Kinetics of the reactions of some 2-phenoxy- and 2-(p-nitrophenoxy)-3-nitro-5-X-thiophenes with benzylamine and N-benzylmethylamine in benzene", J. Chem. Soc., Perkin Trans. 2: Physical Organic Chemistry, 325-334 (1998).
Cummins, J.M., "Disruption of HAUSP gene stabilizes p53", Nature, 1-2 (2004).
Faustrup, H., et al., "USP7 counteracts SCFβTrCP—but not APC-Cdh1-mediated proteolysis of Claspin", J. Cell Biol., 184(1): 13-19 (2009).
Haupt, Y. et al., "Mdm2 promotes the rapid degradation of p53", Nature, 387: 296-299 (1997).
Hershko, A. et al., "The Ubiquitin System", Annu. Rev. Biochem., 67: 425-79 (1998).

(Continued)

*Primary Examiner* — Golam M M Shameem
(74) *Attorney, Agent, or Firm* — Patrick J. Hagan; Dann, Dorfman, Herrell and Skillman, P.C.

(57) ABSTRACT

Disclosed are novel compounds which are useful as therapeutics, especially in anti-neoplastic therapy and in other therapeutic regimes where cysteine protease inhibition is implicated.

12 Claims, No Drawings

(56) References Cited

OTHER PUBLICATIONS

Honda, R., "Oncoprotein MDM2 is a ubiquitin ligase E3 for tumor suppressor p53", FEBS Letters, 420: 25-27 (1997).

Komander, D., "Breaking the chains: structure and function of the deubiquitinases", Nature, 10: 550-563 (2009).

Li, M. et al., "A Dynamic Role of HAUSP in the p53-Mdm2 Pathway", Molecular Cell, 13: 879-886 (2004).

Nicholson, B., "Characterization of ubiquitin and ubiquitin-like-protein isopeptidase", Protein science, 17: 1035-1043 (2008).

Nijman, S., "A Genomic and Functional Inventory of Deubiquitinating Enzymes", Cell, 123: 773-786 (2005).

Song, M., "The deubiquitinylation and localization of PTEN are regulated by a HAUSP-PML network", Nature, 455: 817-817 (2008).

van der Horst, A., "FOXO4 transcriptional activity is regulated by monoubiquitination and USP7/HAUSP", Nat. Cell Biol., 8(10): 1064-73 (2006).

Thurston, D.E. et al., Chemistry and Pharmacology of Anticancer Drugs, CRC Press, pp. 37-84 (2007).

Chen, Z. et al., "Selective Chk1 inhibitors differentially sensitize p53-deficient cancer cells to cancer therapeutics", Int. J. Cancer, 119(2): 2784-94 (2006) [Abstract only].

Sheng, Y. et al., "Molecular recognition of p53 and MDM2 by USP7/HAUSP", Nature Structural & Molecular Biology, 13(3): 285-291 (2006).

* cited by examiner

ANTI-NEOPLASTIC COMPOUNDS, COMPOSITIONS AND METHODS

CROSS-REFERENCE TO RELATED APPLICATIONS

The present application is the U.S. national phase of PCT/US10/29358, filed Mar. 31, 2010, which claims the benefit of U.S. Provisional Patent Application Nos. 61/165,713, filed Apr. 1, 2009 and 61/165,728, filed Apr. 1, 2009, the entire disclosures of which are incorporated by reference herein.

FIELD OF THE INVENTION

The present invention relates generally to the field of cysteine protease inhibitors, pharmaceutical compositions comprising such inhibitors and methods of use thereof.

BACKGROUND OF THE INVENTION

There are five major classes of proteases, categorized based on their mechanism of catalysis. These are the serine, cysteine, aspartic, threonine and metallo-proteases. Members of the cysteine protease class include deubiquitylation enzymes, caspases, calpains, cathepsins, viral, bacterial, protozoan or parasitic cysteine proteases.

Many proteins in the cell are regulated by the ubiquitin-proteasomal pathway (A. Hershko et al., Annu. Rev. Biochem., Annu Rev Biochem, 67: 425-79 (1998)). The conjugation and deconjugation of ubiquitin (Ub), a small (76 amino acids; 8.6 kDa) polypeptide, to proteins is mediated by families of enzymes (A. Hershko et al., supra). Typically, polyubiquitylated proteins are degraded by the proteasome.

Ubiquitin deconjugation is mediated by deubiquitylating enzymes (DUBs also known as deubiquitinating enzymes) that cleave the peptide bond of ubiquitin fused at its C-terminus to other proteins (including ubiquitin) or small molecules such as amines or thiols. In particular, DUBs may serve to spare certain proteins, or at least prolong their cellular lifetime, by removing the polyubiquitin tag, thereby preventing proteasomal degradation. DUBs are typically cysteine proteases and can be grouped into multiple classes. The largest class of DUBs, the ubiquitin specific protease (USP) family, cleave ubiquitin from a wide range of protein substrates (D. Komander et al., Nat. Rev. Mol. Cell. Biol., 10(8): 550-63 (2009); S. M. Nijman et al., Cell, 123(5): 773-86 (2005)). DUBs have been linked genetically and/or biochemically to a variety of diseases, including cancer, inflammatory disease, neurodegenerative disease, muscle wasting, infertility, and viral infection.

DUBs have gained interest as targets for the treatment of cancer. Attention was brought to the proteaseome pathway as a target for cancer therapy with the approval of the proteasome inhibitor bortezomib (Velcade®) for the treatment of multiple myeloma. Extended treatment with bortezomib is limited by its associated toxicity and drug resistance. However, therapeutic strategies that target specific aspects of the ubiquitin-proteasome pathway upstream of the proteasome, such as DUBs, are predicted to be better tolerated.

The DUB USP7 plays a key role in regulating the ubiquitylation of the RING-finger E3 ligase Mdm2 (and its human homolog Hdm2) (M. Li et al., Mol. Cell, 13(6): 879-86 (2004); J. Cummins et al., Nature, 428(6982): 1 p following 486 (2004)). Hdm2 binds the tumor suppressor, p53 and facilitates its degradation by the proteasome by polyubiquitylating p53 (R. Honda et al., FEBS Lett, 420(1): 25-7 (1997); Y. Haput et al., 387(6630): 296-9 (1997)). Importantly, a recent publication illustrates the therapeutic relevance of directly inhibiting USP7 catalytic activity as opposed to blocking the protein-protein interaction with its substrate (C. L. Brooks et al., Oncogene, 26(51): 7262-6 (2007).

In addition to the proven link between USP7, Hdm2 and p53, inhibition of USP7 is predicted to impact cancer by a variety of other mechanisms. For example, Hdm2 also binds to and inhibits the p53 paralog, p73 (E. Balint, Oncogene, 18(27): 3923-9 (1999)). Additional reported substrates of USP7 include claspin (H. Faustrup et al., Cell Biol., 184(1): 13-9 (2009)), the anti-proliferative protein PTEN (M. S. Song et al., Nature, 455(7214): 813-7 (2008)) and the anti-proliferative transcription factor, FOXO4 (A. van der Horst et al., Nat. Cell Biol., 2006. 8(10): 1064-73 (2006)).

Combination therapy approaches consisting of two or more therapeutic agents are widely used to treat many diseases including neoplastic diseases. When used effectively, combination therapies often exhibit synergistic therapeutic effects resulting in a reduction in dose and toxicity of the therapeutic agents.

Genotoxic agents such as Doxorubicin, Etoposide or Chlormethine are approved chemotherapeutic agents that damage tumor cell DNA by a variety of mechanisms resulting in tumor cell death (D. E. Thurston et al., Chemistry and Pharmacology of Anticancer Drugs, CRC Press, 37-84 (2007)). The USP7 substrate claspin is required for G2/M cell cycle arrest following DNA damage and inhibition of USP7 is predicted to prevent activation of the checkpoint kinase Chk1 and allow tumor cells to continue to proliferate in the presence of genotoxic agents. The continued proliferation of tumor cells in the presence of genotoxic agents results in tumor cell death. Thus a combination therapy utilizing a USP7 inhibitor with a genotoxic agent is predicted to result in synergistic tumor cell death.

U.S. Pat. Nos. 4,451,660 and 4,649,154, EP 31173, GB1459571, GB 1577743, US2007/0212712, US2006/0217381, JP03133975 and JP 04021677 disclose compounds comprising nitrothiophene. Nitrothiophene derivatives also were reported by Khimicheskaya Tekhnologiya, 50: 93-96 (2007), Journal of Chemical Research, Synopses, 7: 266-267 (2001), Journal of the Chemical Society, Perkin Transactions 2: Physical Organic Chemistry, 2: 325-334 (1998), Journal of the Chemical Society, Perkin Transactions 2: Physical Organic Chemistry, 2, 388-92 (1981). U.S. Pat. No. 4,994,485, WO 2005/070916 A1 and WO 2005/066152 A1 relate to cyanothiophene derivatives. Insofar as is known, however, it has not previously been disclosed nor suggested that nitrothiophene or cyanothiophene derivatives are effective for inhibiting deubiquitinating enzymes.

A number of inhibitors of USP7 have been reported. These include tetracyclic compounds (US2008/0103149 A1) and cyano-pyrazine derivatives (US2007/0032499 A1). See also WO 2004/009023 and F. Colland et al., Mol. Cancer. Ther., 8: 2286-95 (2009). However, no clinically approved compounds have emerged from these leads. Thus, clinically effective inhibitors of USP7 would fulfill a therapeutic need.

To date, there have been no reports of DUB inhibitors or activators that have successfully entered the clinic. One of the primary hurdles in the discovery and development of compounds that modulate DUB activity is the lack of a reliable, robust, high-throughput assay for the screening for inhibitors or activators of USPs. Progenra, the assignee of this application, has developed such an assay (U.S. Provisional Application No. 61/083,756). By utilizing its novel assay, Progenra has succeeded in identifying small molecule inhibitors of USP7.

SUMMARY OF THE INVENTION

The present invention in one aspect provides novel compounds which are useful as therapeutic agents, especially in antineoplastic therapeutics and in other therapeutic regimes where cysteine protease inhibition is implicated. These compounds have the structure of Formula (I):

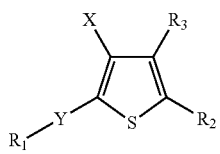

wherein
X represents halogen, nitro, cyano, —SCF$_3$, or —SO$_2$CF$_3$;
Y represents —S—, —O—, —SO$_2$— or —SO—;
R$_1$ represents an unsubstituted or substituted aryl group, or an unsubstituted or substituted heteroaryl group;
R$_2$ represents halogen, formyl, a substituted lower alkyl, unsubstituted or substituted lower alkenyl or unsubstituted or substituted lower alkanoyl group, an unsubstituted or substituted aroyl group, —SO$_2$—NR$_4$R$_5$, —SO$_2$—R$_6$; —CONR$_4$R$_5$, —NHCONR$_4$R$_5$, —NHCOR$_4$, —COOR$_6$ or cyano;
R$_3$ represents —H, lower alkyl, —NR'R", or an unsubstituted or substituted aryl group wherein R' and R" independently represent —H, unsubstituted or substituted lower alkyl or unsubstituted or substituted phenyl;
R$_4$ and R$_5$ each, independently, represent —H, an unsubstituted or substituted lower alkyl group, an unsubstituted or substituted cycloalkyl group, an unsubstituted or substituted aryl group, an unsubstituted or substituted heteroaryl group, an unsubstituted or substituted heterocycle group, or R$_4$ and R$_5$ together with the nitrogen atom to which they are attached form an unsubstituted or substituted heterocycle group;
R$_6$ represents —H or an unsubstituted or substituted alkyl (C$_1$-C$_6$) group; said substituted lower alkyl group, said substituted lower alkenyl group, said substituted lower alkanoyl group and said substituted cycloalkyl group have 1-3 substituents selected from the group of —NR'R", —OR', oxo, unsubstituted or substituted phenyl, unsubstituted or substituted heteroaryl, unsubstituted or substituted heterocycle, unsubstituted or substituted cycloalkyl, —SR$_6$, —COOR$_6$, —CONR$_{4a}$R$_{5a}$, —SOR$_6$, —SO$_2$R$_6$, wherein R' and R" are as previously defined, and R$_{4a}$ and R$_{4b}$ independently represent —H, unsubstituted or substituted lower alkyl, unsubstituted or substituted cycloalkyl, unsubstituted or substituted heterocycle or R$_{4a}$ and R$_{5b}$ together with the nitrogen atom to which they are attached form an unsubstituted or substituted heterocycle group;
said substituted aryl group, said substituted aryol group and said substituted phenyl group have 1-5 substituents selected from the group of —NO$_2$, unsubstituted or substituted lower alkyl, —NR'R", —SO$_2$R$_6$, halogen, —OR$_6$, heterocycle, —SO$_2$NR'R", —SR$_6$, lower alkanoyl, —NRCOOR$_6$, —NHC(=NH)—NH$_2$, —NHCOR$_6$, —C(=NH)—NH$_2$ and —CN;
said substituted heteroaryl group and substituted heterocycle group have 1-5 substituents selected from the group of unsubstituted or substituted lower alkyl, unsubstituted or substituted cycloalkyl, —OR$_6$, —NR'R", —COOR$_6$, lower alkanoyl, oxo, —SO$_2$R$_6$, —C(=NH)—NH$_2$, —NHC(=NH)—NH$_2$, —C(=NH)—NH$_2$ and —CN.

and the stereoisomer, pharmaceutically acceptable salt and N-oxide forms of said compound;

except that when —Y—R$_1$ represents —O-phenyl, and the phenyl group thereof is substituted with one or more substituents, including —O—CH(—R$_a$)—COR$_b$, wherein R$_a$ is hydrogen or lower alkyl and R$_b$ is hydroxyl, lower alkoxy or dialkylamino, then R$_2$ does not represent cyano, acetyl, halogen or —COOR$_c$, wherein R$_c$ is hydrogen or lower alkyl; and with the proviso that said formula does not include the compounds selected from the group consisting of 1-[5-(2,3-dichlorophenyl)sulfanyl-4-nitro-2-thienyl]ethanone; 1-[5-(4-chlorophenyl)sulfanyl-4-nitro-2-thienyl]ethanone; 2-[(5-ethylsulfonyl-3-nitro-2-thienyl)sulfanyl]aniline; 5-(4-chlorophenyl)sulfanyl-4-nitro-thiophene-2-sulfonamide; and 4-nitro-5-[[5-trifluoromethyl)-2-pyridyl]sulfanyl] thiophene-2-sulfonamide.

In another aspect, the present invention provides pharmaceutical compositions comprising at least one compound of formula (I), above, or a pharmaceutically acceptable salt thereof, together with a pharmaceutically acceptable excipient, carrier or diluent.

In a further aspect, the present invention provides therapeutic methods of using the compounds of formula (I), above, or a pharmaceutically acceptable salt thereof.

One such method involves inhibiting cysteine protease activity of a deubiquitylating enzyme in a subject by administering to the subject an effective amount of at least one compound according to the present invention or a pharmaceutically acceptable salt thereof. In preferred embodiments of this method, the deubiquitylating enzyme is USP7.

Another method of the invention involves inhibiting USP7 in a subject by administering to the subject an effective amount of a compound according to the present invention or a pharmaceutically acceptable salt thereof.

In certain therapeutic methods, at least one compound of formula (I), above, is administered as a therapeutic agent to a subject for the treatment of a neoplastic disease or condition. Preferably, the therapeutic agent is administered to a subject for the treatment of various forms of cancer, including, without limitation, leukemia, non-small cell lung cancer, colorectal cancer, CNS cancer, melanoma, ovarian cancer, renal cancer, prostate cancer, breast cancer, multiple myeloma, or osteosarcoma.

The anti-cancer therapeutic methods described herein may be carried out as a monotherapy or as a combination therapy in conjunction with radiation therapy and/or additional chemotherapeutic agents, preferably one or more DNA-damaging anti-cancer agent.

The therapeutic methods of the invention may also be practiced using at least one of the following compounds, or a pharmaceutically acceptable salt thereof: 1-[5-(2,3-dichlorophenyl)sulfanyl-4-nitro-2-thienyl]ethanone (sometimes referred to herein as "P5091"); 1-[5-(4-chlorophenyl) sulfanyl-4-nitro-2-thienyl]ethanone; 2-[(5-ethylsulfonyl-3-nitro-2-thienyl)sulfanyl]aniline; 5-(4-chlorophenyl)sulfanyl-4-nitro-thiophene-2-sulfonamide; 4-nitro-5-[[5-trifluoromethyl)-2-pyridyl]sulfanyl]thiophene-2-sulfonamide.

DETAILED DESCRIPTION OF THE INVENTION

Preferred compounds of formula (I), above, are those in which:
X represents —NO$_2$ or —CN;
Y represents —S— or —O—;
R$_1$ represents substituted aryl or substituted heteroaryl;

$R_2$ represents (i) $COONR_4R_5$, wherein $R_4$ and $R_5$ are as defined previously, or (ii) $C(=O)R_d$ or $CH(-OH)R_d$, wherein $R_d$ represents an unsubstituted or substituted lower alkyl group.

Among the preferred compounds described immediately above, especially preferred are those in which X represents $-NO_2$, Y represents $-S-$, $R_1$ represents a halogen-substituted heteroaryl group with chlorine substitution being most preferred, e.g., a 3,5-dichloropyridyl group, or a halogen-substituted aryl group, with chlorine substitution being most preferred, e.g., 2,4-, 3,5-, 2,3-, 2,6- or 3,4-dichlorophenyl; and $R_2$ represents $-COONR_4R_5$, wherein one of $R_4$ or $R_5$ represents hydrogen and the other of $R_4$ and $R_5$ represents substituted aryl which is a phenyl group substituted with at least one of unsubstituted or substituted alkoxy (e.g., dialkylaminoalkoxy), alkylsulfonyl, sulfamoyl, heterocycle or guanidino; an unsubstituted heteroaryl group which is a quinoline or isoquinoline group or a 5-member heteroaryl group having 1 or 2 heteroatoms selected from the group of N, O, S; a substituted heteroaryl, which is a substituted pyridyl group, a substituted isoxazolyl group or a substituted pyrazolyl group, which are substituted by at least one optionally substituted alkyl, cycloalkyl, alkoxy, monoalkylaminoalkyl, dialkylaminoalkyl, dialkylaminoalkylamino group; substituted heterocyclic, which is an alkyl-substituted piperidino group; and substituted heteroarylalkyl, which is an alkyl-substituted pyrazinyl group.

Preferred $R_2$ substituents for the thiophene amide derivatives of the invention are $-OR'$ and $-NR'R''$, wherein R' and R'' are as previously defined. Such substituents include, without limitation, dialkylaminoalkoxy, dialkylaminoalkylamino, or the like, which enhance water solubility of the compounds.

Definitions:

As used in the preceding sections and throughout the rest of this specification, the following terms, unless otherwise clearly indicated, shall be understood to have the following meanings.

The term "alkyl" refers to a saturated, branched or linear hydrocarbon group. Typical alkyl groups include, but are not limited to, methyl, ethyl, propyl, isopropyl, butyl, isobutyl, t-butyl, pentyl, isopentyl, hexyl and the like. In preferred embodiments, the alkyl groups are ($C_1$-$C_6$) alkyl, with ($C_1$-$C_3$) being particularly preferred. "Lower alkyl" refers to $C_1$-$C_6$ alkyl.

"Alkenyl" refers to an unsaturated branched or linear hydrocarbon group containing a carbon-carbon double bond. Typical alkenyl groups include, but are not limited to, ethenyl, propenyl, n-butenyl, i-butenyl, 3-methylbut-2-enyl, n-pentenyl, heptenyl, octenyl, nonenyl, decenyl. "Lower alkenyl" refers to $C_2$-$C_6$ alkenyl.

"Lower alkanoyl" refers to $-COR_e$ wherein $R_e$ represents lower alkyl.

"Halogen" refers to fluoro, chloro, bromo or iodo.

"Alkoxy" refers to an alkyl-O— group where alkyl is as previously described. Exemplary alkoxy groups include, for example, methoxy, ethoxy, propoxy, butoxy and heptoxy.

"Alkylthio" refers to an alkyl-S— group wherein alkyl is as previously described. Exemplary alkylthio groups include methylthio, ethylthio, i-propylthio and heptylthio.

"Monoalkylamino" refers to an —NHR' group wherein R' is as previously described. Exemplary monoalkylamino groups include methylamino and ethylamino.

"Dialkylamino" refers to an —NR'R" group wherein each of R' and R" is as previously described. Exemplary dialkylamino groups include ethylmethylamino, dimethylamino and diethylamino.

The term "aryl" refers to a moiety having an unsaturated cyclic hydrocarbon group which has a conjugated (4n=2) π electron system. Typical aromatic moieties include, but are not limited to, phenyl, naphthyl, biphenyl, indenyl and the like. In preferred embodiments, the aromatic moiety contains 5-20 carbons in the ring system, with 5-10 carbon atoms being particularly preferred.

The term "aroyl" refers to the moiety $-COR_f$ wherein $R_f$ represents aryl.

The term "heteroaryl" refers to an aryl moiety wherein one or more carbon atoms are each independently replaced with a heteroatom. Typical heteroatoms include nitrogen, oxygen, and sulfur. The heteroatom may be in oxy form such as, for example, $N^+$—$O^-$. Examples of heteroaryl groups include pyrrolyl, furanyl, thienyl, pyrazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl pyridazinyl, triazinyl, picolinyl, imidazopyridinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, benzopyranyl, chromenonyl, thianaphthenyl, benzoxazolyl, benzooxadiazolyl, benzisoxazolyl, cinnolinyl, phthalazinyl, naphthyridinyl, [1,2,4]triazolo[1,5-a]pyrimidinyl and quinoxalinyl.

"Cycloalkyl" refers to a saturated or partially saturated mono- or bicyclic, optionally fused, alkyl ring system containing 3 to 10 carbon atoms. Examples of cycloalkyl groups include such groups as cyclopropyl, cyclobutyl, cyclopentyl, cyclohexyl, cyclohexenyl, cycloheptyl, norbornanyl and adamantanyl.

"Heterocycle" refers to a $C_3$-$C_8$ cycloalkyl group wherein one or more carbon atoms are each independently replaced with a heteroatom. Typical heteroatoms include nitrogen, oxygen, and sulfur. Examples of heterocycle groups include azetidinyl, 3H-benzooxazolyl, 1,1-dioxo-thiomorpholinyl, 1,4-diazapinyl, pyrrolidinyl, pyrrolinyl, imidazolidinyl, imidazolinyl, imidazolidinyl, oxazolidinyl, oxopiperidinyl, pirazolidinyl, pirazolinyl, pyrazalinyl, piperidinyl, piperazinyl, hexahydropyrimidinyl, quinuclidinyl, methyl-8-azabicyclo[3,2,1]octanyl, morpholinyl, thiomorpholinyl, dihydrobenzofuranyl, tetrahydrofuranyl, tetrahydropyranyl, tetrahydropyranolopyridinyl, tetrahydro-1,3a,7-triaza-azulenyl, dihydro-oxazolyl, dithiolyl, oxathiolyl, dioxazolyl, oxathiazolyl, pyranyl, oxazinyl, oxathiazinyl, and oxadiazinyl. Included within the definition of "heterocycle" are fused ring systems, including, for example, ring systems in which an aromatic ring is fused to a heterocycle ring and ring systems in which a heteroaromatic ring and/or a cycloalkyl ring is fused to a heterocycle ring. Examples of such fused ring systems include, for example, 2,3-dihydrobenzofuran, 2,3-dihydro-1,3-benzoxazole, 2,3-dihydrobenzo[b][1,4]dioxinyl, benzodioxolyl, 3-oxo-3,4-dihydro-2H-benzo[b][1,4]oxazinyl, phthalic anhydride, indoline, isoindoline, tetrahydroisoquinoline, chromane and isochroman.

The terms "substituted" or "optionally substituted" refer to chemical moieties, wherein one or more hydrogen atoms may be replaced by a halogen atom, a $NH_2$, SH, $NO_2$ or OH group, or by an alkyl, alkenyl, alkanoyl, heteroalkyl, aryl, heteroaryl, cycloalkyl or heterocycle group as defined herein. The last-mentioned groups may be optionally substituted.

The terms "subject" and "patient" are used interchangeably herein to refer to a warm blooded animal such as a mammal, preferably a human, or a human child, which is afflicted with, or has the potential to be afflicted with one or more diseases and/or conditions described herein.

The expression "neoplastic disease or condition" refers to any condition characterized by the presence of an aberrant growth of abnormal cells or tissue, including, but not limited to all cancers and tumors, whether benign or malignant.

"Therapeutically effective amount" refers to an amount of a compound of the present invention effective to inhibit or treat the initiation, growth and/or progression of a neoplastic disease or condition. The term "treat", "treatment" or "treating" when used herein in relation to cancer therapy refers to the administration of a compound of the invention as a monotherapy, or part of a combination therapy, for inhibiting the growth or metastasis of any neoplastic tissue that may exist in a patient and/or stimulating regression thereof, including reducing the size and/or number of such neoplasms and/or inducing the death of neoplastic cells. Effective treatment may also be manifested by providing a patient relief from or alleviation of the clinically recognized symptoms or other diagnostic indicators of a neoplastic disease or condition. The methods described herein may also be used to delay the onset or prevent the occurrence of a neoplastic disease or condition in a patient.

"Pharmaceutically acceptable" refers to those compounds, materials, compositions, and/or dosage forms which are, within the scope of sound medical judgment, suitable for contact with the tissues of human beings and non-human animals without excessive toxicity, irritation, allergic response, or other adverse complications commensurate with a reasonable benefit/risk ratio.

"Pharmaceutically acceptable salts" refers to salts of compounds of the present invention derived from the combination of such compounds with non-toxic acids or bases.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, paratoluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic compounds such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically-acceptable salts, other salts are included within the scope of this invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and the like. Mixtures of such solvates can also be prepared. The source of such solvates can be from the solvent of crystallization, inherent in the solvent of preparation or crystallization, or adventitious to such solvent. Such solvates are also within the scope of the present invention.

The present invention also encompasses pharmaceutically acceptable prodrugs of the above-described compounds. As used herein, "prodrug" refers to any compound which is converted by metabolic processes within the body of a subject to an active agent that has a formula within the scope of the present invention. Since prodrugs are known to enhance numerous desirable qualities of pharmaceuticals (e.g., solubility, bioavailability, manufacturing, etc.) the compounds of the present invention may be produced for delivery in prodrug form. Conventional procedures for the selection and preparation of suitable prodrug derivatives are described, for example, in *Prodrugs*, Sloane, K. B., Ed.; Marcel Dekker New York (1992).

All other terms used in the description of the present invention have their art-recognized meanings.

As will be apparent to anyone skilled in the art, the compounds of the present invention may have one or more chiral centers, and in that case, exist in various stereoisomeric forms. The compounds of the present invention encompass all such optical isomers, diastereomers and enantiomers. The compounds are normally prepared as a racemic mixture or racemate and can conveniently be used as such, but individual enantiomers can be isolated or synthesized by conventional techniques if so desired. Such racemates and individual enantiomers and mixtures thereof form part of the present invention.

It is well known in the art how to prepare and isolate such optically active forms from a mixture of enantiomers. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: New York, 1994, and Jacques, J, et al. *Enantiomers, Racemates, and Resolutions*; Wiley: New York, 1981, each incorporated by reference herein in their entireties.

Synthesis Methods

The compounds of this invention may be made by various methods known in the art. Such methods include those of the following reaction schemes, as well as the methods specifically exemplified below. Modifications of such methods and schemes that involve techniques commonly practiced in the art of organic synthesis may also be used. The variable numbering and structure numbering shown in the synthetic schemes are distinct from, and should not be confused with, the variables or structure numbering in the claims or other parts of the specification. The variables in the schemes are meant only to illustrate how to make certain of the compounds of this invention. General routes suitable to prepare chemical species exemplified herein are shown in the schemes I-VII. The reagents and starting materials are commercially available, or readily synthesized by well-known techniques by one of ordinary skill in the art. All preparative methods disclosed herein are contemplated to be implemented on any scale, including milligram, gram, multigram, kilogram, multikilogram or commercial industrial scale.

ABBREVIATIONS

The symbols and conventions used in the reaction schemes and preparative examples set forth below are consistent with those used in the contemporary scientific literature, for example, the journal of the American Chemical Society or the Journal of Biological Chemistry. Specifically, the following abbreviations may be used in the examples and throughout the specification:

| | |
|---|---|
| g | (grams); |
| L | (liters); |
| mL | (milliliter) |
| μL | (microliter); |
| RT | (room temperature); |
| h | (hour); |
| mg | (milligrams); |
| TEA | (triethylamine); |
| TFA | (trifluoroacetic acid); |
| MeOD | (deuterated methanol); |
| mL | (milliliters); |
| mmol | (millimole); |
| M | (mole); |
| min | (minute); |
| TLC | (thin layer chromatography); |
| THF | (tetrahydrofuran); |
| DCM | (methylene chloride); |
| CDCl$_3$ | (deuterated chloroform); |
| SO$_2$Cl | (sulfonyl chloride) |
| EtOH | (ethanol); |
| NaOMe | (sodium methoxide); |
| NaBH$_4$ | (sodium boronhydride); |
| MeOH | (methanol); |
| i-PrOH | (isopropanol); |
| CuBr | (copper(I) bromide); |
| NaOH | (sodium hydroxide); |
| CuCN | (copper(I) cyanide); |
| CuSO$_4$ | (copper(II) sulfate); |
| EtOAc | (ethylacetate); |
| DMSO | (dimethylsulfoxide); |
| HCl | (hydrochloric acid); |
| DMF | (N,N-dimethylformide); |
| CHCl$_3$ | (chloroform); |
| ACN | (Acetonitrile) |
| Me | (methyl); |
| Ac | (acetyl); |
| Et | (ethyl); |
| t-Bu | (tert-butyl); |
| N$_2$ | (nitrogen); |
| K$_2$CO$_3$ | (potassium carbonate); |
| Et$_2$O | (diethyl ether); |
| HOAc | (acetic acid); |
| Sat'd | (saturated); |
| MgSO$_4$ | (magnesium sulphate); |
| Na$_2$SO$_4$ | (sodium sulfate); |
| CS$_2$ | (carbon disulfide) |
| HPLC | (high performance liquid chromatography); |
| ACTU | (2-Chloro-1,1,3,3-tetramethyluronium hexachloroantimonate); |
| HATU | (2-(7-Aza-1H-benzotriazole-1-yl)-1,1,3,3-tetramethyluronium hexafluorophosphate) |
| MCPBA | (3-chloroperoxybenzoic acid); |
| IMS | (industrial methylated spirits) |

The compounds of the present invention can be synthesized according to Scheme I-VII.

Scheme I

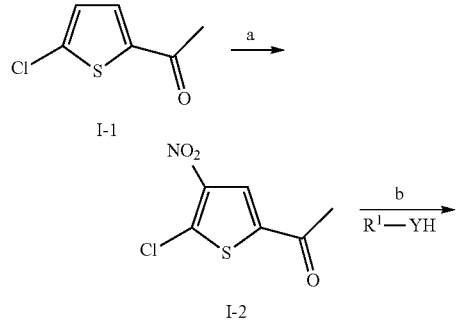

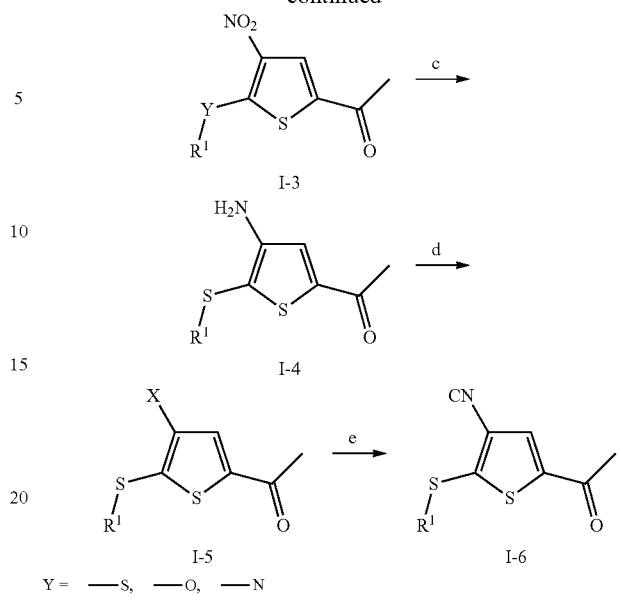

Reagents and conditions: (a) fuming HNO$_3$, RT; (b) NaOMe, MeOH, RT; (c) Fe/NH$_4$Cl, EtOH/H$_2$O, 80° C.; (d) tert-butylnitrite, copper(I) halide, ACN, 60° C.; (e) Cu(I)CN, pyridine, microwave, 150° C.

Scheme II

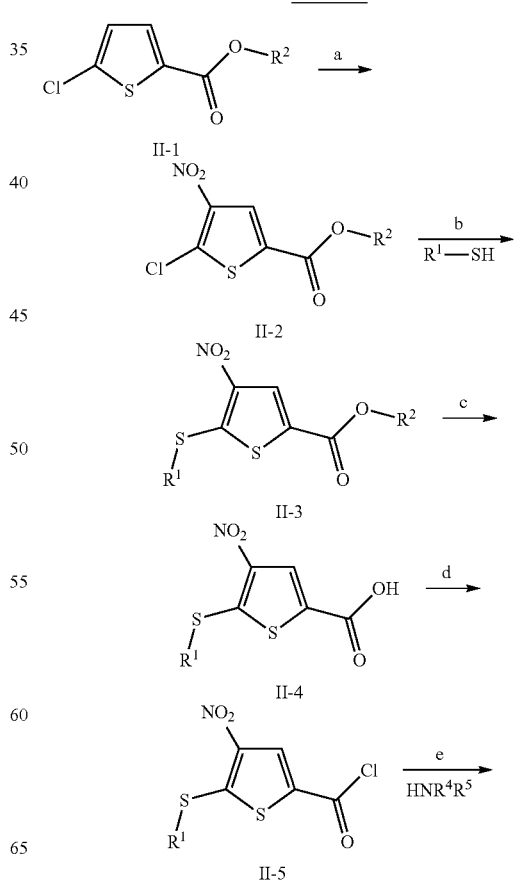

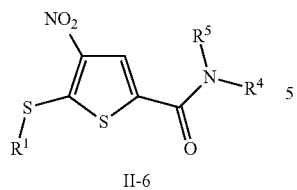

II-6

Reagents and conditions: (a) fuming HNO₃, H₂SO₄, room temperature; (b) NaOEt, EtOH, RT; K₂CO₃, DMF, RT or K₂CO₃, toluene, RT; (c) 1M NaOH, THF, RT; H₂SO₄, reflux or KOH, IMS/H₂O, RT; (d) SOCl₂, toluene, RT; ACTU, DCM or HATU, DCM, RT; (e) DIPEA or TEA, DCM.

Scheme III

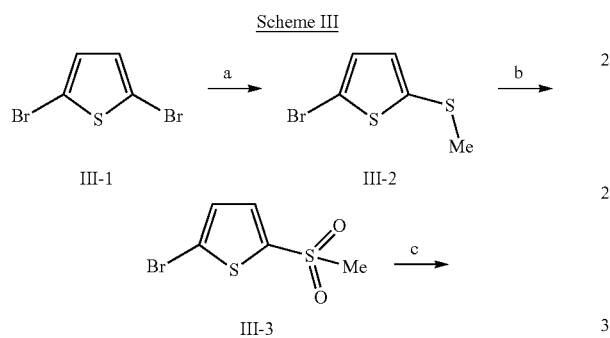

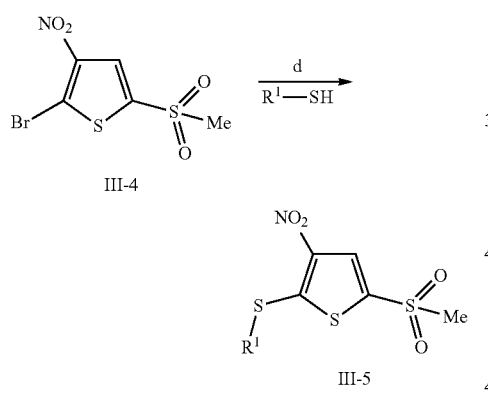

Reagents and conditions: (a) n-BuLi, MeSSMe, THF, −78° C.; (b) m-CPBA, DCM, RT; (c) NaNO₃, H₂SO₄, 0° C.; (d) K₂CO₃, DMF, RT.

Scheme IV

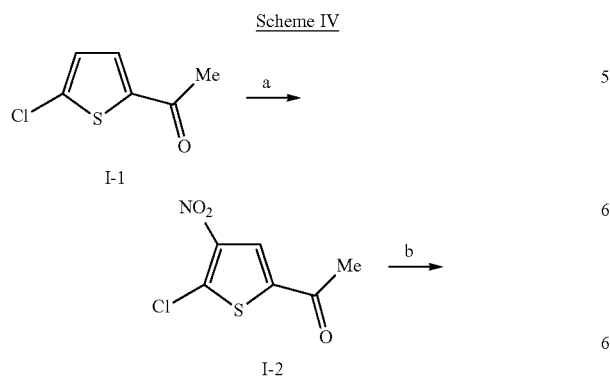

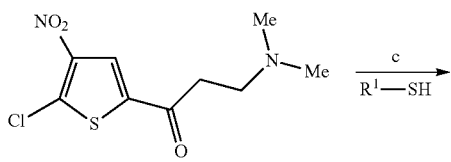

IV-1

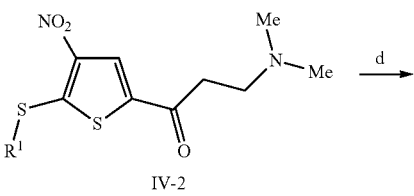

IV-2

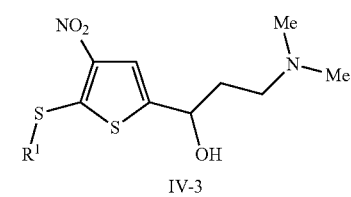

IV-3

Reagents and conditions: (a) fuming HNO₃, RT; (b) paraformaldehyde, dimethylamine, conc. HCl, i-PrOH, 80° C.; (c) K₂CO₃, DMF, RT; (d) NaBH₄, MeOH, RT.

Scheme V

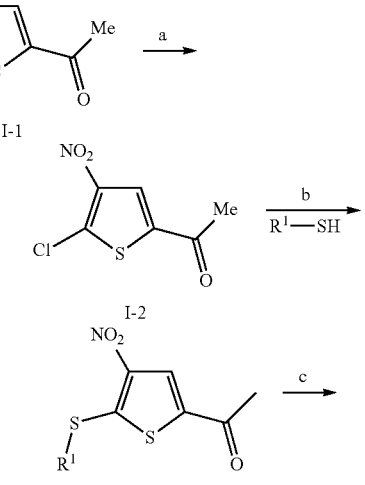

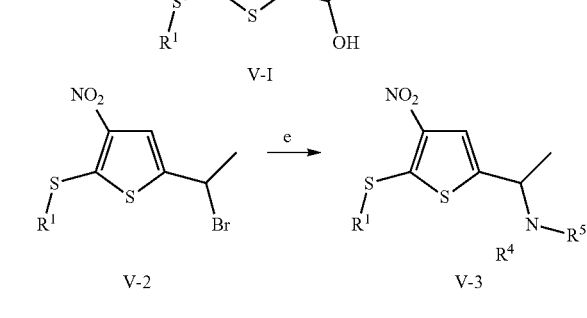

Reagents and conditions: (a) fuming HNO$_3$, RT; (b) NaOMe, MeOH, RT; (c) NaBH$_4$, MeOH, RT; (d) PBr$_3$, DCM, RT; (e) primary amines, MeOH, THF, 80° C. or microwave, 100° C.

Scheme VI

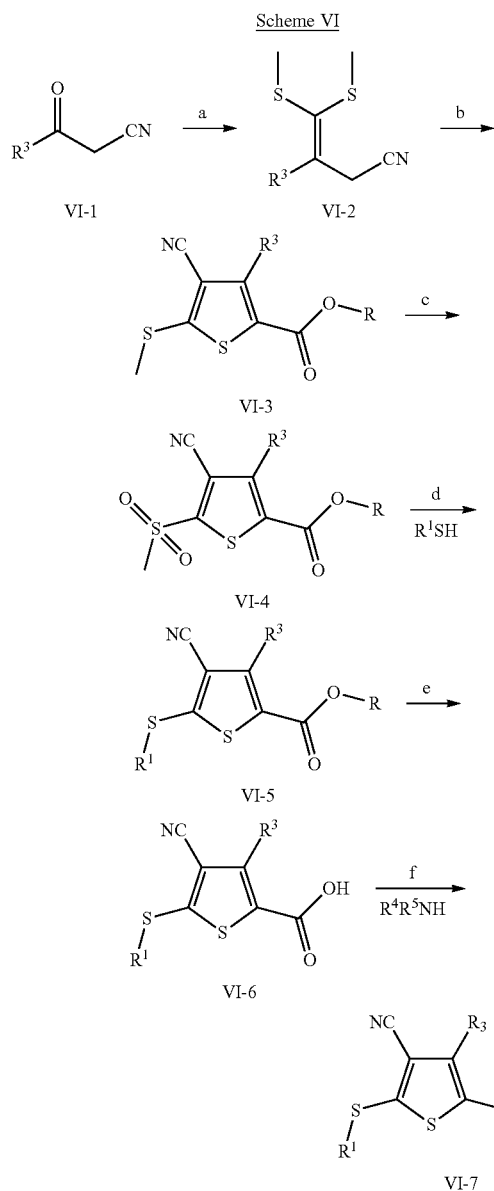

Reagents and conditions: (a) CS$_2$, NaH, MeI, DMSO, RT, 1 h; (b) methyl thioglycolate, TEA, MeOH, 85° C., 10 min; (c) m-CPBA, DCM, RT, 5 h; (d) arylthiol, DIPEA, i-PrOH, 150° C., microwave, 10 min; (e) 1N NaOH, THF, 40° C., 2 h or LiOH, THF, H$_2$O, RT, over night; (f) SOCl$_2$, toluene, TEA, RT; ACTU, DIPEA, DCM, 40° C., 2-4 h or HATU, amine, DIPEA, DMF, RT, over night.

Scheme VII

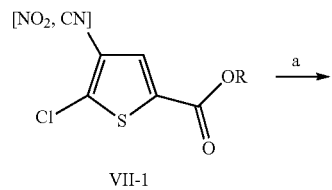

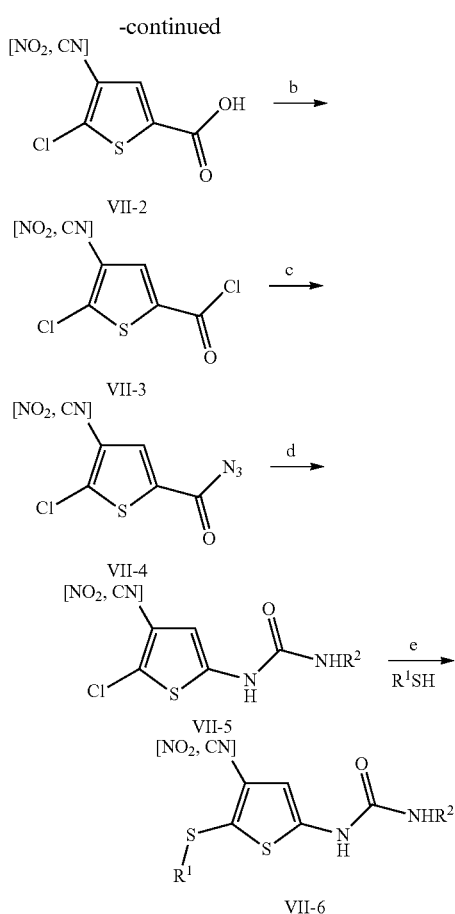

Reagents and conditions: (a) 18 N H$_2$SO$_4$, 100° C., over night; (b) oxalyl chloride, DMF, DCM, RT, 4 h; (c) NaN$_3$, THF, RT, 6 h; (d) Toluene, amine, 80° C.; (e) K$_2$CO$_3$, DMF, RT, 18 h.

Formulation and Route of Administration

Any compound of the invention may be administered to a subject by itself, or in the form of a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiological acceptable carriers, diluents, excipients, or auxiliaries which facilitate processing of the compounds into preparations which can be used pharmaceutically. A specific formulation method will be dependent upon the route of administration chosen.

For topical administration the compounds of the invention may be formulated as solutions, gels, ointments, creams, suspensions etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the compounds of the invention may be formulated in aqueous solutions, preferably in physiologically compatible buffers such as Hank's solution, Ringer's solution, or physiological saline buffer. The solution may contain formulatory agents such as suspending, stabilizing and/or dispersing agents.

Alternatively, the compounds may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the compounds can be readily formulated by combining the compounds with pharmaceutically acceptable carriers well known in the art. Such carriers enable the compounds of the invention to be formulated as tablets, pills, dragees, capsules, liquid gels, syrups, slurries, suspensions and the like, for oral ingestion by a patient to be treated. For oral solid formulations, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium, carboxymethylcellulose, and/or polyvinylpyrrolidone (PVP); granulating agents; and binding agents. If desired, disintegrating agents may be added, such as the cross-linked polyvinylpyrrolidine, atgar, or alginic acid or a salt thereof such as sodium alginate.

If desired, solid dosage forms may be sugar-coated or enteric-coated using standard techniques.

For oral preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compounds may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and suitable powder base such as lactose or starch.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery system may be employed. Liposomes and emulsions are well known examples of delivery vehicles that may be used to deliver the compounds of the invention. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. A variety of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

As the compounds of the invention may contain charged side chains or termini, they may be included in any of the above-described formulations as the free acids or bases or as pharmaceutically acceptable salts. Pharmaceutical salts tend to be more soluble in aqueous and other protic solvents than are the corresponding free acid or base forms.

Effective Dosage

The anti-neoplastic compounds of the invention can be used to manufacture a medicament in a suitable dosage unit form for ease of administration and uniformity of dosage. "Dosage unit form", as used herein, refers to a physically discrete unit of anti-neoplastic agent appropriate for the patient to be treated. Each dosage should contain the quantity of active material calculated to produce the desired therapeutic effect either as such, or in association with the selected pharmaceutical carrier medium and/or the supplemental active agent(s), if any.

The compounds of this invention, or pharmaceutical compositions thereof, are administered or applied in a therapeutically effective amount, as previously defined. The amount administered should be effective to ameliorate, or prevent the symptoms of the disease or disorder, or prolong the survival of the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture (i.e. the concentration of test compound that inhibits 50% of USP7). Such information can be used to more accurately determine useful doses in humans.

Initial dosages can also be estimated from in vivo data. e.g. animal models, using techniques that are well known in the art. One having ordinary skill in the art could readily optimize administration to humans based on animal data.

Dosage amount and interval may be adjusted individually to provide therapeutically effective serum levels of the compounds described herein. Usual patient dosages for administration by injection range from about 0.1 to 50 mg/kg/day, preferably from about 0.5 to 5 mg/kg/day. Therapeutically effective serum levels may be achieved by administering multiple doses each day.

In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on a number of factors, including age, weight and gender of the subject being treated, the severity of the disease or condition, the manner of administration and the judgment of the prescribing physician or other medical specialist. However, an effective amount of compound of the present invention for the treatment of cancer should be in the range of 0.1 to 100 mg/kg body weight of recipient (mammal) per day. More usually the effective amount should be in the range of 0.1 to 10 mg/kg body weight per day. The amount per day would usually be from 3 to 3000 mg. This amount maybe given in a single dose per day or in a number (such as two, three, four, five, or more) of sub-doses per day such that the total daily dose is the same. An effective amount of salt, solvate, or physiologically functional derivative thereof, may be determined as a portion of the effective amount of the compound of the present invention per se.

Toxicity

Preferably, a therapeutically effective dose of the compound described herein will provide therapeutic benefit without causing appreciable toxicity.

Toxicity of the compounds described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The ratio of the median lethal dose to the median effective dose is the therapeutic index, used in quantitative comparison of drugs. Compounds which exhibit high therapeutic indices are preferred. The data obtained from these cell culture assays and animal studies can be used in formulation of a dosage range that is not toxic for use in humans. The dosage of the compounds described herein lies preferably within a range of circulating concentrations that include the effective dose with little or no toxicity. The dosage may vary within this range depending on the dosage form employed and the route of administration utilized. The exact formulation, route of administration and dosage can be chosen by the individual physician in view of the patient's condition. (See, e.g., Fingl et al., In: The Pharmacological Basis of Therapeutics, Ch. 1, p. 1, 1975).

Utility

The compounds of the present invention are useful, inter alia, as therapeutic agents. Particularly, the compounds have demonstrated cysteine protease inhibitory activity, which is capable of producing an anti-neoplastic effect. In one embodiment, the present invention provides a method for treating or preventing diseases and disorders, such as those disclosed herein, which comprises administering to a subject in need of such treatment or prevention a therapeutically effective amount of a compound of the present invention.

In an additional embodiment, the present invention provides a method for inhibiting the deubiquitylating enzyme USP7 activity comprising providing a compound of the present invention in an amount sufficient to result in effective inhibition. The compounds of the present invention can be administered to treat neoplastic diseases or conditions, including various forms of cancer, such as multiple myeloma, leukemia, prostate cancer, breast cancer, colorectal cancer, non-small cell lung cancer, CNS cancer, melanoma, ovarian cancer, renal cancer, or osteosarcoma. In preferred embodiments, the compounds can be administered to treat such diseases and disorders such as multiple myeloma, acute myeloid leukemia, chronic lymphocytic leukemia, colon cancer or prostate cancer.

Although not wishing to be bound to any particular theory regarding the mechanism of action of the compounds of formula I in inhibiting the cysteine protease activity of DUBs, it is believed that the observed effect is due to inhibition of substrate binding. Experiments carried out to date have successfully demonstrated inhibition of the cysteine protease activity of deubiquitylating enzyme.

As previously mentioned, the compounds of the invention may be administered for the treatment of a neoplastic disease or disorder in a combination therapy with other suitable treatment modalities. In the case of cancer, such other suitable treatment modalities include, without limitation, administration of radiation therapy, e.g., gamma radiation therapy, and/ or a supplemental chemotherapeutic agent.

It is intended that a combination therapy, as practiced in accordance with this invention, includes the use of any chemically compatible combination of two or more compounds of formula (I), above, with each other, or one or more compounds of formula (I) with an additional anti-cancer agent outside the scope of formula (I), whether currently known or hereafter developed, so long as the combination does not eliminate the anti-neoplastic activity of the compound(s) of the invention, or the anti-neoplastic activity of any pharmaceutical composition containing such compound(s).

The preferred therapeutic agents for use in combination with the compound(s) of formula (I) for the treatment or prevention of cancer are genotoxic anti-cancer agents. Representative examples of such therapies are the following:

1. γ-irradiation
2. genotoxic alkylating reagents
   a. Dacarbazine, procarbazine, Carmustine, Lomustine, Uramustine, Busulfan, Streptozocin, Altreamine, Ifosfamine, Chrormethine, cyclophasphamide Cyclophosphamide, chlorambucil, Fluorouracil (5-Fu) Melphalan, Triplatin tetranitrate
   b. Satraplatin, Nedaplatin, Cisplatin, Carboplatin, Oxaliplatin
3. Tubulin inhibitors
   a. Taxol, Docetaxel, Vinblastin, Epothilone, Colchicine, Cryptophycin, BMS-247550, Rhizoxin, Ecteinascidin, Dolastin 10, Cryptophycin 52, IDN-5109
4. Topoisomerase inhibitors
   a. Topo I inhibitors: Irinotecan, Topotecan, Camptothecins (CPT)
   b. Topo II inhibitors: Amsacrine, Etoposide, Teniposide, Epipodophyllotoxins
5. CHK1 and CHK2 inhibitors
   a. TCS2312, PF-0047736, AZ07762, A-69002, A-641397
   b. LY2603618, C3742, SC-203885
6. others: doxorubicin, Epirubicin, bleomycin, mytomycin c Through combination therapy, reduction of adverse drug reaction and potentiation of anticancer activity are achievable by the combined effects of anticancer agents having different mechanisms of action, including reduction of the non-sensitive cell population; prevention or delaying of occurrence of drug resistance; and dispersing of toxicity by means of a combination of drugs having different toxicities.

When an anti-cancer agent used in combination has a particular medication cycle, it is preferable to establish an appropriate medication cycle for the compound of formula (I) and such anti-cancer agent, so that the desired effects are attained. Specifically, the frequency of administration, dosage, time of infusion, medication cycle, and the like, may be determined properly according to individual cases, considering the kind of anticancer agent, state of the patients, age, gender, etc.

In using the combination therapy of the present invention, the same dose as that usually given as a monotherapy or a slightly reduced dose (for example, 0.10-0.99 times the highest dose as a single agent) may be given through a normal administration route.

Combination therapy involving administration of a compound of formula (I) and an additional anti-cancer agent can be readily implemented provided a suitable administration route, frequency of administration and dosage are properly selected. Examples include: (1) administration of a composition containing a compound of formula (I) and a supplemental anti-cancer agent, i.e., as a single formulation; (2) administration of two species of formulations separately prepared from a compound of formula (I) and a supplemental anti-cancer agent, respectively, through the same administration route; (3) time interval difference administration of two species of formulations separately prepared from a compound of formula (I) and an anti-cancer agent, respectively, through the same administration route (e.g., a compound of formula (I) is administered first, and then an additional anti-cancer agent, or vice versa); (4) administration of two species of formulations separately prepared from a compound of formula (I) and an additional anti-cancer agent, respectively, through different administration routes; and (5) time interval difference administration of two species of formulation separately prepared from a compound of formula (I) and an anti-cancer agent, respectively, through different administration routes (e.g., a compound of formula (I) is administered first, and then an anti-cancer agent, or vice versa).

In a preferred embodiment of combination therapy according to the present invention, a compound of formula (I) and another anti-cancer agent are separately formulated, and the resulting two types of compositions are administered concomitantly (including partially concomitant) or at a time interval through an administration route suitable to each composition and at a proper frequency of administration. In the time interval difference administration, it is necessary to administer the compositions at a time interval which promotes the anticancer effect. Preferably, the second composition is administered within 2 weeks, more preferably 7 days, yet more preferably 3 days, after administration of the first composition. In the event there is concern about an undesired drug-drug interaction between a compound of formula (I) and another anti-cancer agent, it is appropriate to administer them at an interval required for avoidance of such an interaction.

The methods of the present invention will normally include medical follow-up to determine the therapeutic or prophylactic effect brought about in the patient undergoing treatment with the compound(s) and/or composition(s) described herein. Efficacy of the methods may be assessed on the basis of tumor regression, e.g., reducing the size and/or number of neoplasms, inhibition of tumor metastasis, decrease in a serological marker of disease, or other indicator of an inhibitory or remedial effect.

The following examples describe the invention in further detail, with reference to specific embodiments. These are representative embodiments of the invention which are provided for illustrative purposes only, and which should not be regarded as limiting the invention in any way.

Unless otherwise indicated in the examples, all temperature is expressed in Centigrade (C). All reactions were conducted under an inert atmosphere at ambient temperature unless otherwise noted. Reagents employed without synthetic details are commercially available or made according to literature procedures.

$^1$H NMR spectra were recorded on a Varian Unity INOVA™ 300 MHz, Bruker AVANCE™ 250 equipped with a DUL 5 mm probe or a Bruker AVANCE™ 400 equipped with a broadband multinuclear including F (BBFO), broadband multinuclear excluding F(BBO) & dual probe. The nuclear magnetic resonance (NMR) spectral characteristics refer to chemical shifts (δ) expressed in parts per million (ppm) versus tetramethylsilane (TMS) as reference standard. Coupling constants (J) are in units of hertz (Hz). The nature of the shifts as to multiplicity is reported as s (singlet), d (doublet), t (triplet), q (quartet), dd (double doublet), dt (double triplet), m (multiplet), br (broad).

Mass spectra and liquid chromatography MS were recorded on a Micromass Platform or Agilent system. Detection is by MS, UV at 214 nM using either electrospray ionization (ESI), chemical ionization (CI), electron impact (EI) or by fast atom bombardment (FAB) methods.

HPLC data was recorded on an Agilent system with Acquity C-18 reverse phase column (2.1×100 mm, 1.7 μm) running gradient of 10-90% MeCN/H$_2$O (+0.1% ammonium acetate) over 10 minutes. Flow rate 0.3 mL/min. HPLC data was also recorded on an Agilent system with Luna C-18 reverse phase column (2.0×30 mm, 3.0 μm) running gradient of 5-95% MeCN/H$_2$O (+0.05% TFA) over 4 minutes. Flow rate 1.0 mL/min.

All reactions were monitored by thin-layer chromatography on 0.25 mm E. Merck silica gel plates (60F-254), visualized with UV light, 5% ethanolic phosphomolybdic acid, p-anisaldehyde solution, aqueous potassium permanganate or potassium iodide/platinum chloride solution in water.

EXAMPLES

Example 1

Step A:
1-(5-chloro-4-nitro-2-thienyl)ethanone: 2-Chloro-5-acetylthiophene (80.3 g, 0.5 mol) was added in portions to fuming nitric acid (500 mL) cooled to −5° C. with an ice/methanol bath. On completion of addition the reaction was removed from the cold bath and stirred at ambient temperature for 30 minutes before the reaction mixture was poured into ice water (4 L). After stirring for 10 minutes the solid which formed was collected by filtration and washed with water (500 mL). The solid was then dissolved in dichloromethane (500 mL) the water was separated and the organic solution was dried (MgSO$_4$). Removal of the solvent under reduced pressure gave an orange solid. The crude material was re-crystallized from IMS (350 mL) to give the title product as a light brown solid (46.89 g, 45% yield). $^1$H NMR (CDCl$_3$) δ: 8.07 (1H, s), 2.58 (3H, s).

Step B:
1-[5-(2-Chlorophenylsulfanyl)-4-nitro-2-thienyl]ethanone: To a 0.1 M stock solution of sodium methoxide in anhydrous methanol (11 mL, 1.1 mmol) was added the 2-chlorobenzenethiol (0.144 g, 1 mmol) and the resulting mixture stirred at ambient temperature for 15 minutes. 1-(5-Chloro-4-nitro-2-thienyl)ethanone (206 mg, 1 mmol) was added and the mixture was stirred at ambient temperature for 2 hours. After this time the reaction was quenched by the addition of water (15 mL) and the resulting precipitate was collected by filtration, washed with water (10 mL) and dried in vacuo at 40° C. overnight. The solid was then crystallized from acetonitrile to afford the title compound as a dark orange solid (165 mg, 52.6% yield). $^1$H NMR (300 MHz, CDCl$_3$) δ: 8.09 (1H, s), 7.77 (1H, ddd, J=7.58, 1.58, 0.36 Hz), 7.40-7.67 (3H, m), 2.49 (3H, s).

Example 2

1-[5-(2,4-Dichlorophenylsulfanyl)-4-nitro-2-thienyl]ethanone: Prepared according to the procedure described as in Step B for example 1 from 1-(5-Chloro-4-nitro-2-thienyl)ethanone (0.164 g, 0.8 mmol) and 2,4-dichlorobenzenethiol (0.143 g, 0.8 mmol). The title compound was obtained as an orange solid (132 mg, 47.3% yield). $^1$H NMR (300 MHz, CDCl$_3$) δ: 8.09 (1H, s), 7.68 (2H, m), 7.42 (1H, d), 2.50 (3H, s).

Example 3

1-[5-(2,4-Difluorophenylsulfanyl)-4-nitro-2-thienyl]ethanone: Prepared according to the procedure described as in Step B for example 1 from 1-(5-Chloro-4-nitro-2-thienyl)

ethanone (0.171 g, 0.83 mmol) and 2,4-fluorobenzenethiol (0.121 g, 0.83 mmol). The title compound was obtained as a cream colored solid (170 mg, 64.6% yield). $^1$H NMR (300 MHz, CDCl$_3$) δ: 8.08 (1H, s), 7.66 (1H, m), 7.07 (2H, m), 2.50 (3H, s).

Example 4

1-{4-Nitro-5-[2-(trifluoromethyl)phenylsulfanyl]-2-thienyl}ethanone: Prepared according to the procedure described as in Step B for example 1 from 145-Chloro-4-nitro-2-thienyl)ethanone (0.317 g, 1.55 mmol) and 2-triflouomethylbenzenethiol (0.276 g, 1.55 mmol). The title compound was obtained as a yellow solid (173 mg, 32.2% yield). $^1$H NMR (300 MHz, CDCl$_3$) δ: 8.07 (1H, s), 7.79 (2H, m), 7.66 (2H, m), 2.49 (3H, s).

Example 5

1-[5-(Naphth-1-ylsulfanyl)-4-nitro-2-thienyl]ethanone: Prepared according to the procedure described as in Step B for example 1 from 1-naphthalenethiol (320 mg, 2 mmol) and 1-(5-Chloro-4-nitro-2-thienyl)ethanone (412 mg, 2 mmol) to afforded the title compound as a yellow solid (192 mg, 29% yield). $^1$H NMR (300 MHz, CDCl$_3$) δ: 8.33 (1H, m), 8.11 (1H, m), 8.08 (1H, s), 7.98 (2H, m), 7.59 (3H, m), 2.43 (3H, s).

Example 6

1-[5-(3-Chlorophenylsulfanyl)-4-nitro-2-thienyl]ethanone: Prepared according to the procedure described as in Step B for example 1 from 1-(5-Chloro-4-nitro-2-thienyl)ethanone (0.502 g, 2.45 mmol) and 3-chlorobenzenethiol (0.353 g, 2.45 mmol). The title compound was obtained as a yellow solid (0.476 g, 62% yield). $^1$H NMR (300 MHz, CDCl$_3$) δ: 8.08 (1H, s), 7.68 (1H, m), 7.45-7.60 (3H, m), 2.49 (3H, s).

Example 7

1-[5-(2,6-Dichlorophenylsulfanyl)-4-nitro-2-thienyl]ethanone: Prepared according to the procedure described for as in Step B example 1 from 1-(5-Chloro-4-nitro-2-thienyl)ethanone (0.502 g, 2.45 mmol) and 3-chlorobenzenethiol (0.353 g, 2.45 mmol). The title compound was obtained as a pale orange solid (0.441 g, 52% yield). $^1$H NMR (300 MHz, CDCl$_3$) δ: 8.10 (1H, s), 7.44-7.59 (3H, m), 2.50 (3H, s).

Example 8

1-[5-(3,4-Dichlorophenylsulfanyl)-4-nitro-2-thienyl]ethanone: Prepared according to the procedure described as in Step B for example 1 from 1-(5-Chloro-4-nitro-2-thienyl)ethanone (0.502 g, 2.45 mmol) and 3,4-dichlorobenzenethiol (0.438 g, 2.45 mmol). The title compound was obtained as an off-white solid (0.631 g, 74.6% yield). $^1$H NMR (300 MHz, CDCl$_3$) δ: 8.10 (1H, s), 7.80 (1H, s), 7.70 (1H, d), 7.50 (1H, d), 2.50 (3H, s).

Example 9

1-[5-(3,5-Dichlorophenylsulfanyl)-4-nitro-2-thienyl]ethanone: Prepared according to the procedure described as in Step B for example 1 from 1-(5-Chloro-4-nitro-2-thienyl)ethanone (0.502 g, 2.45 mmol) and 3,5-dichlorobenzenethiol (0.438 g, 2.45 mmol). The title compound was obtained as a yellow solid (0.403 g, 47.5% yield). $^1$H NMR (300 MHz, CDCl$_3$) δ: 8.08 (1H, s), 7.57 (3H, m), 2.51 (3H, s).

Example 10

1-{5-[4-(Trifluoromethyl)phenylsulfanyl]-4-nitro-2-thienyl}ethanone: Prepared according to the procedure described as in Step B for example 1 from 1-(5-Chloro-4-nitro-2-thienyl)ethanone (0.502 g, 2.45 mmol) and 4-trifluorobenzenethiol (0.436 g, 2.45 mmol). The title compound was obtained as a peach colored solid (0.711 g, 84% yield). $^1$H NMR (300 MHz, CDCl$_3$) δ: 8.09 (1H, s), 7.81 (4H, m), 2.50 (3H, s).

Example 11

1-[5-(2-Naphthylsulfanyl)-4-nitro-2-thienyl]ethanone: Prepared according to the procedure described as in Step B for example 1 from 1-(5-Chloro-4-nitro-2-thienyl)ethanone (0.502 g, 2.45 mmol) and naphthalene-2-thiol (0.392 g, 2.45 mmol). The title compound was obtained as a cream colored solid (0.585 g, 73% yield). $^1$H NMR (300 MHz, CDCl$_3$) δ: 8.23 (1H, m), 8.09 (1H, s), 7.99 (1H, d), 7.92 (2H, m), 7.63 (3H, m), 2.46 (3H, s).

Example 12

1-[5-(4-Bromophenylsulfanyl)-4-nitro-2-thienyl]ethanone: Prepared according to the procedure described as in Step B for example 1 from 4-Bromobenzenethiol (1.03 g, 5.5 mmol) and 1-(5-chloro-4-nitro-2-thienyl)ethanone (1.14 g, 5.5 mmol). The title compound was obtained as an orange solid (1.15 g, 58% yield). $^1$H NMR (300 MHz, CDCl$_3$) δ: 8.07 (1H, s) 7.68 (2H, d, J=8.69 Hz), 7.53 (2H, d, J=8.69 Hz), 2.49 (3H, s).

Example 13

1-[4-nitro-5-(4-nitrophenylsulfanyl)-2-thienyl]ethanone: Anhydrous N,N-dimethylformide (5 mL) was degassed with nitrogen for 30 minutes then sodium hydride (60% dispersion in mineral oil, 0.11 g, 2.75 mmol) was added. 4-Nitrobenzenethiol (0.38 g, 2.43 mmol) was added in portions at ambient temperature and the resulting mixture was stirred at ambient temperature under nitrogen for 20 minutes. Then 1-(5-chloro-4-nitro-2-thienyl)ethanone (0.5 g, 2.43 mmol) was added and the reaction mixture was stirred at ambient temperature overnight under nitrogen. The reaction mixture was diluted with water (40 mL) and stirred for 30 minutes. The precipitated solid was collected by filtration and washed with water (2×4 mL). The crude solid was recrystallised from acetonitrile (12 mL) to afford the title compound as a brown solid (0.302 g, 38% yield). $^1$H NMR (300 MHz, CDCl$_3$) δ: 8.38 (2H, d, J=8.85 Hz), 8.09 (1H, s), 7.89 (2H, d, J=8.85 Hz), 2.50 (3H, s).

Example 14

1-(4-nitro-5-thiazol-2-ylsulfanyl-2-thienyl)ethanone: To a solution of thiazole-2-thiol (0.05 g, 0.5 mmol) in toluene (10ML), was added 1-(5-Chloro-4-nitro-2-thienyl)ethanone (0.102 g, 0.5 mmol) and K$_2$CO$_3$ (0.69 g, 5 mmol). The resulting reaction mixture was stirred at ambient temperature for 18 h. The reaction mixture was diluted with water (10 mL) and was extracted with ethyl acetate. The organic extract was dried (Na$_2$SO$_4$), concentrated under vacuum and the residue purified by silica gel chromatography using a mixture of 70:30 ethyl acetate and hexane as eluent to afford the title product as a solid (60 mg, 43% yield). $^1$H NMR (400 MHz, d$_6$-DMSO) δ: 8.51 (2H, s), 8.26 (2H, dd), 8.23 (2H, dd), 2.54 (3H, s). MS m/z: 287.9 [M+H]$^+$.

Example 15

1-[5-(1-methylimidazol-2-yl)sulfanyl-4-nitro-2-thienyl]ethanone: Prepared according to the procedure described for example 14 from 1-(5-Chloro-4-nitro-2-thienyl)ethanone (0.1 g, 0.49 mmol) and N-methyl imidazole-2-thiol (0.056 g, 0.49 mmol). The title compound was obtained as a solid (50 mg, 36% yield). $^1$H NMR (400 MHz, d$_6$-DMSO) δ: 8.48 (2H, s) 7.64 (2H, dd) 7.28 (2H, dd), 3.42 (3H, s), 2.52 (3H, s). MS m/z: 283.9 [M+H]$^+$.

Example 16

1-[4-nitro-5-(4-phenylphenyl)sulfanyl-2-thienyl]ethanone: Prepared according to the procedure described for example 1 from 1-(5-Chloro-4-nitro-2-thienyl)ethanone (82 mg, 0.4 mmol) and 4-phenylbenzenthiol (74 mg, 0.4 mmol). The title compound was obtained as a solid (30 mg, 21% yield). $^1$H NMR (400 MHz, CDCl$_3$) δ: 8.09 (1H, s), 7.74 (2H, m) 7.65 (2H, m), 7.52 (2H, m), 7.44 (2H, m), 2.49 (3H, s). MS m/z: 355.9 [M+H]$^+$.

Example 17

Step A:
3,5-dichloropyridine-4-thiol sodium salt: Sodium hydrosulfide hydrate (0.248 g, 3.14 mmol) was suspended in anhydrous methanol (10 mL), 3,4,5-trichloropyridine (0.475 g, 2.62 mmol) was added and the mixture was stirred at 35° C. for 17 hours. The reaction mixture was filtered to remove solid residues and the filtrate was concentrated to give a solid. The solid was triturated with dichloromethane to afford the title product as a white solid (0.4 g, 76% yield). $^1$H NMR (400 MHz, d$_6$-DMSO) δ: 7.88 (2H, s). MS m/z: 179.9 [M+H]$^+$.
Step B:
1-[5-[(3,5-dichloro-4-pyridyl)sulfanyl]-4-nitro-2-thienyl]ethanone: To a solution of 1-(5-chloro-4-nitro-2-thienyl)ethanone (113 mg, 0.55 mmol) in toluene (2 mL), was added 3,5-dichloropyridine-4-thiol sodium salt (100 mg, 0.55 mmol) and potassium carbonate (113 mg, 0.825 mmol). The resulting reaction mixture was stirred at ambient temperature for 18 hours. After this time, the reaction mixture was filtered to remove the solid residues. The organic solution was diluted with ethyl acetate (15 mL) and was washed with water (2 mL×2) and brine (1 mL×2), dried (Na$_2$SO$_4$) and concentrated under vacuum. The residue was purified by silica gel chromatography using a mixture of 96:4 hexane and ethyl acetate as eluent to afford the title product as a solid (22 mg, 12% yield). $^1$H NMR (400 MHz, MeOD) δ: 8.85 (2H, m) 8.36 (1H, s), 2.52 (3H, s). MS m/z: 348.8 [M+H]$^+$.

Example 18

Step A:
3,4,5-trichloro-1-oxido-pyridin-1-ium: To a stirred solution of 3,4,5-trichloropyridine (1 g, 5.45 mmol) in dichloromethane (20 mL) at 0° C., was added dropwise a 30% hydrogen peroxide solution (1.2 mL, 10.9 mmol). Following the addition, the temperature was allowed to rise to room temperature and was stirred for 15 hours. The reaction mixture was diluted with dichloromethane (50 mL) and was washed with water (10 mL) and then by brine (25 mL×2). The organic phase was dried (Na$_2$SO$_4$), concentrated under vacuum to afford the title product as a white solid (0.8 g, 74% yield). $^1$H NMR (400 MHz, d$_6$-DMSO) δ: 8.78 (2H, s). MS m/z: 197.90 [M+H]$^+$.
Step B:
3,5-dichloro-1-oxido-pyridin-1-ium-4-thiol: Prepared according to the procedure described for example 17 from 3,4,5-trichloro-1-oxido-pyridin-1-ium (0.75 g, 3.8 mmol) and sodium hydrosulfide hydrate (0.38 g, 4.57 mmol). The title compound was obtained as a brown solid (0.52 g, 70% yield). $^1$H NMR (400 MHz, d$_6$-DMSO) δ: 7.89 (2H, s). MS m/z: 195.9 [M+H]$^+$.
Step C:
1-[5-(3,5-dichloro-1-oxido-pyridin-1-ium-4-yl)sulfanyl-4-nitro-2-thienyl]ethanone: To a solution of 1-(5-Chloro-4-nitro-2-thienyl)ethanone (0.209 g, 1 mmol) in N,N-dimethylformide (4 mL), was added 3,5-dichloro-1-oxido-pyridin-1-ium-4-thiol sodium salt (0.2 g, 1 mmol) and potassium carbonate (0.348 g, 2.56 mmol). The resulting reaction mixture was stirred at ambient temperature for 4 hours. The reaction mixture was poured onto ice (5 mL). After stirring for 10 minutes the solid which formed was collected by filtration and washed with water (10 mL) and air dried. The crude solid product was purified by silica gel flash chromatography using a mixture of 90:10 dichloromethane and methanol as eluent to afford the title product as a yellow solid (0.23 g, 63% yield). $^1$H NMR (400 MHz, d$_6$-DMSO) δ: 8.93 (1H, s) 8.54 (1H, s), 2.54 (3H, s). MS m/z: 363.0 [M+H]$^+$.

Example 19

1-[5-(2,3-dichlorophenyl)sulfanyl-4-nitro-2-thienyl]ethanol: Sodium borohydride (54 mg, 1.44 mmol) was added to a suspension of 1-[5-(2,3-dichlorophenylsulfanyl)-4-nitro-2-thienyl]ethanone (0.5 g, 1.44 mmol) in methanol (10 mL) and the resulting mixture was stirred at ambient temperature. After 90 minutes, TLC showed no starting material remaining so the reaction was quenched by addition of water (20 mL). The resulting precipitate was collected by filtration and dissolved in dichloromethane (50 mL). The organic solution was dried over magnesium sulfate (MgSO$_4$), filtered and the solvent removed to give a yellow solid. The crude solid was re-crystallized from methanol to afford the title product as a yellow solid (0.164 g, 33% yield). $^1$H NMR (300 MHz, CDCl$_3$) δ: 7.65 (2H, m), 7.40 (1H, m), 7.33 (1H, t), 4.94 (1H, q), 1.99 (1H, d, J=4.74 Hz), 1.51 (3H, d, J=6.48 Hz).

Example 20

Step A:
1-[4-amino-5-(2,4-dichlorophenyl)sulfanyl-2-thienyl]ethanone: To a two necked 250 mL round bottom flask, charged with 1-[5-(2,4-Dichlorophenylsulfanyl)-4-nitro-2-thienyl]ethanone (7.0 g, 20.2 mmol) prepared as in example 2, 50 mL ethanol and 50 mL of water followed by ammonium chloride (4.32 g, 80.8 mmol) and iron powder (4.53 g, 80.8 mmol). The resulting reaction mixture was heated at 80° C. for 2 hours. After this time, the reaction mixture was cooled to ambient temperature and was passed through a cellite cartridge. The filtrate was concentrated and water was added to the residue and extracted with ethyl acetate. The combined organic layer was separated, dried (Na$_2$SO$_4$), filtered and concentrated to afford the title product (6.4 g, 78% yield). $^1$H NMR (400 MHz, d$_6$-DMSO) δ: 7.64 (1H, s), 7.44 (1H, s), 7.37 (1H, m), 6.68 (1H, m), 2.50 (3H, s).

Step B:

1-[5-(2,4-dichlorophenyl)sulfanyl-4-iodo-2-thienyl]ethanone: To a dark solution of $I_2$ (0.958 g 7.5 mmol) in acetonitrile (20 mL), was added t-butyl nitrite (0.4 g, 3.75 mmol) slowly. The resulting solution was heated to 60° C. for 20 min. To the above solution, was added dropwise of a solution of 1-[4-amino-5-(2,4-dichlorophenyl)sulfanyl-2-thienyl]ethanone (0.8 g, 2.5 mmol) in acetonitrile (20 mL). The resulting mixture was heated at 60° C. for 2 hours. After this time the reaction mixture was quenched with sodium hydroxide aqueous solution (1 M), and extracted with ethyl acetate. The organic layer was separated, dried ($Na_2SO_4$) and concentrated. The crude solid was purified by silica gel chromatography using a 98:2 mixture of hexane and ethyl acetate as eluent to afford the title product as a yellow solid (1.07 g, 46.2% yield). $^1$H NMR (400 MHz, $d_6$-DMSO) δ: 8.16 (1H, s), 7.82 (1H, dd), 7.47 (1H, dd), 7.05 (1H, dd), 2.54 (3H, s). MS m/z: 428.7 [M+H]$^+$.

Example 21

Step A:

1-[4-bromo-5-(2,4-dichlorophenyl)sulfanyl-2-thienyl]ethanone: To a dark solution of copper(I) bromide (0.451 g, 3.14 mmol) in acetonitrile (25 mL), was added t-butyl nitrite (0.892 g, 8.6 mmol) slowly. The resulting solution was heated at 60° C. for 20 min. To the above solution, was added dropwise a solution of 1-[4-amino-5-(2,4-dichlorophenyl)sulfanyl-2-thienyl]ethanone (1.0 g, 3.14 mmol) in acetonitrile (25 mL). The resulting mixture was heated at 60° C. for 2 hours. After this time, the mixture was quenched with a sodium hydroxide aqueous solution (1 M), extracted with ethyl acetate. The organic layer was separated, dried ($Na_2SO_4$) and concentrated. The crude solid was purified by silica gel chromatography using a 98:2 mixture of hexane and ethyl acetate as eluent to afford the title product as a yellow solid (0.7 g, 58% yield). $^1$H NMR (400 MHz, $d_6$-DMSO) δ: 8.20 (1H, s), 7.83 (1H, m), 7.47 (1H, dd), 7.11 (1H, m), 2.55 (3H, s). MS m/z: 380.8 [M+H]$^+$.

Step B:

1-[4-cyano-5-(2,4-dichlorophenyl)sulfanyl-2-thienyl]ethanone: To a CEM microwave tube, was charged with 1-[4-bromo-5-(2,4-dichlorophenyl)sulfanyl-2-thienyl]ethanone as prepared in example 21 (0.6 g, 1.6 mmol), copper(I) cyanide (0.85 g, 9.4 mmol), and pyridine (5 mL) as solvent. The mixture was subjected to microwave irradiation (200 W) on a CEM Discovery™ microwave machine at 150° C. for 30 minutes. After the irradiation, the mixture was cooled to ambient temperature and treated with 20 mL of saturated copper(II) sulfate aqueous solution and extracted with ethyl acetate. The combined organic layer was separated, washed with water, dried ($Na_2SO_4$) and concentrated. The crude was purified by silica gel chromatography using a 96:4 mixture of hexane and ethyl acetate as eluent to afford the title product (0.515 g, 78% yield). $^1$H NMR (400 MHz, $CDCl_3$) δ: 7.69 (1H, s), 7.56 (1H, m), 7.53 (1H, m), 7.33 (1H, m), 2.51 (3H, s). MS m/z: 326.2 [M+H]$^+$.

Example 22

Step A:

2-bromo-5-methylsulfanyl-thiophene: To a solution of 2,5-dibromothiophene (1 g, 4.13 mmol) in tetrahydrofuran (25 mL) cooled at −78° C. under $N_2$, n-BuLi solution in hexane (2M, 2.6 mL, 4.96 mmol) was added dropwise via a syringe. After the addition, the temperature was slowly warmed up to −30° C. and stirred at this temperature for 30 minutes. Then the reaction mixture was cooled to −78° C. and methyldisulfanylmethane (0.467 g, 4.96 mmol) was added dropwise. After the addition, the reaction mixture temperature was slowly warmed up to 0° C. and stirred at this temperature for 30 minutes. After this time, the reaction mixture was quenched with ice water (20 mL) and extracted with diethyl ether (25 mL×3). The combined organic layer was washed with water and brine, dried ($Na_2SO_4$) and concentrated under vacuum to afford as the crude product as brown oil (0.55 g, 64% yield). The crude product was used as such for the next step. $^1$H NMR (400 MHz, $CDCl_3$) δ: 6.91 (1H, d), 6.87 (1H, d), 2.46 (3H, s). MS m/z: 195.1 [M+H]$^+$.

Step B:

2-bromo-5-methylsulfonyl-thiophene: To a solution of 2-bromo-5-methylsulfanyl-thiophene (0.48 g, 2.3 mmol) in dichloromethane (20 mL) cooled at 0° C. in an ice bath, was added m-chloroperoxybenzoic acid (1.69 g, 9.2 mmol). After the addition, the temperature was warmed up to ambient temperature and stirred at this temperature for 6 hours. After this time, the reaction mixture was diluted with dichloromethane (30 mL) and washed with saturated sodium bicarbonate (20 mL) followed by water (10 mL×2) and brine (25 mL×2). The organic layer was separated, dried ($Na_2SO_4$) and concentrated under vacuum to afford as the title product as a white solid (0.31 g, 56% yield). $^1$H NMR (400 MHz, $CDCl_3$) δ: 7.49 (1H, d), 7.45 (1H, d), 3.01 (3H, s).

Step C:

2-bromo-3-nitro-5-methylsulfonyl-thiophene: 2-bromo-5-methylsulfonyl-thiophene (0.3 g, 1.24 mmol) was added to the concentrated sulfuric acid at 0° C. cooling in an ice bath. The resulted mixture was stirred at 0° C. for 5 minutes. Then sodium nitrate was introduced and the mixture was stirred at 0° C. for 1 hour. After this time, the reaction mixture was poured onto to the ice-water (10 mL) and was extracted with ethyl acetate. The organic phase was dried ($Na_2SO_4$) and concentrated under vacuum. The residue was purified by silica gel chromatography using a mixture of 95:5 hexane and ethyl acetate as eluent to afford the title product as a solid (0.17 g, 47% yield). $^1$H NMR (400 MHz, $d_6$-DMSO) δ: 8.37 (1H, s), 2.50 (3H, m).

Step D:

3,5-dichloro-4-[(5-methylsulfonyl-3-nitro-2-thienyl)sulfanyl]pyridine: 3,5-dichloropyridine-4-thiol sodium salt prepared as in example 17 (0.160 g, 0.39 mmol) and 2-bromo-5-methylsulfonyl-3-nitro-thiophene (0.1 g, 0.36 mmol) were dissolved in N,N-dimethylformide (3 mL). To the above mixture, potassium carbonate (0.192 g, 1.39 mmol) was added. The resulting reaction mixture was stirred at ambient temperature for 5 hours. After this time, the reaction mixture was quenched with ice water and stirred at ambient temperature for 20 minutes and the resulting precipitate was collected by filtration, washed with water (10 mL) and dried in vacuo at 40° C. overnight. The solid was triturated with dichloromethane and diethyl ether to afford the title product as an off-white solid (35 mg, 9% yield). $^1$H NMR (400 MHz, $d_6$-DMSO) δ: 9.03 (1H, s), 8.66 (1H, s), 3.56 (3H, s). MS m/z: 383.09 [M+H]$^+$.

Example 23

2-(2,4-dichlorophenyl)sulfanyl-5-methylsulfonyl-3-nitro-thiophene: Prepared by a similar procedure to that described as in Step D for example 22 from the 2-bromo-5-methylsulfonyl-3-nitro-thiophene (148 mg, 0.52 mmol) and 2,4-dichlorobenzenethiol (100 mg, 0.56 mmol) to afford the title product as a solid (50 mg, 25% yield). $^1$H NMR (400 MHz, d$_6$-DMSO) δ: 8.35 (1H, s), 8.10 (1H, m), 8.20 (1H, m), 7.74 (1H, m), 3.42 (3H, s). MS m/z: 381.81 [M+H]$^+$.

Example 24

Step A:
1-(5-chloro-4-nitro-2-thienyl)-3-dimethylamino-propan-1-one: To a solution of 1-(5-chloro-4-nitro-2-thienyl)ethanone (1 g, 4.9 mmol) in isopropanol (20 mL), was added dimethylamine (0.55 g, 6.8 mmol) and paraformaldehyde (0.22 g, 7.3 mmol) and concentrated hydrochloric acid (0.2 mL). The resulting reaction mixture was heated at 80° C. for 18 hours. After this time, the reaction mixture was cooled to 0° C. and stirred at 0° C. for 1 hour. A pale yellow precipitate formed and collected by filtration to afford the corresponding hydrochloride salt of the title product (0.55 g, 38% yield). $^1$H NMR (400 MHz, d$_6$-DMSO) δ: 10.39 (1H, m), 8.69 (1H, s), 3.68 (2H, m), 3.38 (2H, m), 2.80 (6H, s).

Step B:
1-[5-(2,4-dichlorophenyl)sulfanyl-4-nitro-2-thienyl]-3-dimethylamino-propan-1-one: To a solution of 1-(5-chloro-4-nitro-2-thienyl)-3-dimethylamino-propan-1-one hydrochloride salt from the above (0.180 g, 0.687 mmol) and 2,4-dichlorobenzenethiol (0.123 g, 0.687 mmol) in N,N-dimethylformide (3 mL), was added potassium carbonate (0.237 g, 1.71 mmol). The resulting reaction mixture was stirred at ambient temperature for 5 hours. After this time, the reaction mixture was quenched with ice water and stirred at room temperature for 20 min and the precipitate which formed was collected by filtration and washed with water, and dried under vacuum. The crude solid was purified by silica gel chromatography to afford a yellow solid. The resulting solid was treated with hydrochloric acid (2 M). The solution was concentrated and dried under vacuum to afford the corresponding hydrochloride salt of the title product (90 mg, 17% yield). $^1$H NMR (400 MHz, MeOD) δ: 8.61 (1H, s), 8.05 (1H, m), 7.98 (1H, dd), 7.72 (1H, dd), 3.48 (2H, m), 3.33 (2H, m), 2.78 (3H, s). MS m/z: 404.9 [M+H]$^+$.

Example 25

1-[5-(2,4-dichlorophenyl)sulfanyl-4-nitro-2-thienyl]-3-dimethylamino-propan-1-ol: Prepared according to the procedure described for example 19 from 1-[5-(2,4-dichlorophenyl)sulfanyl-4-nitro-2-thienyl]-3-dimethylamino-propan-1-one (0.06 g, 0.148 mmol). The title compound was obtained as a solid (25 mg, 40% yield). $^1$H NMR (400 MHz, d$_6$-DMSO) δ: 8.04 (1H, m), 7.98 (1H, m), 7.69 (1H, m), 7.58 (1H, s), 4.79 (1H, m), 3.06 (2H, m), 2.74 (6H, m), 1.98 (1H, m), 1.94 (1H, m). MS m/z: 421.0 [M+H]$^+$.

Example 26

1-[5-(2,4-dichlorophenyl)sulfanyl-4-nitro-2-thienyl]ethanol: Prepared according to the procedure described for example 19 from 1-[5-(2,4-Dichlorophenylsulfanyl)-4-nitro-2-thienyl]ethanone (1.0 g, 2.87 mmol). The title compound was obtained as a solid (1.0 g, 100% yield). $^1$H NMR (400 MHz, d$_6$-DMSO) δ: 8.02 (1H, m), 7.95 (1H, m), 7.70 (1H, m), 7.46 (1H, m), 4.88 (1H, m), 1.25 (3H, d). MS m/z: 349.8 [M+H]$^+$.

Example 27

Step A:
5-(1-bromoethyl)-2-(2,4-dichlorophenyl)sulfanyl-3-nitro-thiophene: To a solution of 1-[5-(2,4-dichlorophenyl)sulfanyl-4-nitro-2-thienyl]ethanol from example 26 (0.6 g, 1.7 mmol) in dichloromethane (10 mL), was added tribromophosphane (0.28 mL, 2.55 mmol). The resulting reaction mixture was kept under reflux for 2 hours. After this time, the reaction mixture was cooled to ambient temperature, quenched with sat'd sodium carbonate aqueous solution and extracted with ethyl acetate. The combined organic phase was dried (Na$_2$SO$_4$) and concentrated to afford the title compound (800 mg). The crude product was used as such for the next step.

Step B:
1-[5-(2,4-dichlorophenyl)sulfanyl-4-nitro-2-thienyl]ethanamine: 5-(1-bromoethyl)-2-(2,4-dichlorophenyl)sulfanyl-3-nitro-thiophene (0.2 g, 0.49 mmol) was dissolved in ammonia in MeOH (2 M, 8 mL). The resulting mixture was sealed in a steel bomb and was heated at 100° C. for 2 hours. The reaction mixture was concentrated and the crude solid was purified by silica gel chromatography using a 98:2 mixture of dichloromethane and methanol as eluent to afford the title product (16 mg, 10% yield). $^1$H NMR (400 MHz, d$_6$-DMSO) δ: 8.38 (1H, m), 8.08 (1H, m), 7.99 (1H, m), 7.82 (1H, s), 7.71 (1H, m), 4.61(1H, m), 1.45 (3H, d). MS m/z: 331.8 [M+H]$^+$.

Example 28

1-[5-(2,4-dichlorophenyl)sulfanyl-4-nitro-2-thienyl]-N-methyl-ethanamine:
To a solution of 5-(1-bromoethyl)-2-(2,4-dichlorophenyl)sulfanyl-3-nitro-thiophene (0.1 g, 0.243 mmol) in tetrahydrofuran (5 mL), was added N-methylamine (0.012 mL, 0.29 mmol). The resulting reaction mixture was heated at 80° C. under microwave irradiation (200 W) on a CEM Discovery™ microwave machine for 50 minutes. The reaction mixture was concentrated and the crude was purified by silica gel chromatography to afford the title compound as a yellow solid (30 mg, 33% yield). $^1$H NMR (400 MHz, d$_6$-DMSO) δ: 7.83 (2H, m), 7.54 (1H, m), 7.49 (1H, s), 3.83 (1H, q), 2.44 (3H, s), 1.32 (3H, d). MS m/z: 376.8 [M+H]$^+$.

Example 29

1-[5-(2,4-dichlorophenyl)sulfanyl-4-nitro-2-thienyl]-N,N-dimethyl-ethanamine: Prepared according to the procedure described for example 28 from 5-(1-bromoethyl)-2-(2,4-dichlorophenyl)sulfanyl-3-nitro-thiophene (0.1 g, 0.25 mmol) and dimethylamine (0.19 mL, 0.8 mmol). The title compound was obtained as a solid (15 mg, 16% yield). $^1$H NMR (400 MHz, MeOD) δ: 7.92 (1H, m), 7.88 (1H, m), 7.85 (1H, m) 7.58 (1H, m), 4.74 (1H, q), 2.81 (3H, m), 2.78 (3H, m), 1.67 (3H, d). MS m/z: 376.9 [M+H]$^+$.

Example 30

1-[5-(2,4-dichlorophenyl)sulfanyl-4-nitro-2-thienyl]-N-[(4-methoxyphenyl)methyl]ethanamine: 5-(1-bromoethyl)-2-(2,4-dichlorophenyl)sulfanyl-3-nitro-thiophene (0.8 g, 1.9 mmol), 4-methoxybenzylamine (0.4 mL, 2.85 mmol) and potassium carbonate (0.524 g, 3.8 mmol) were mixed in N,N-dimethylformide (15 mL). The resulting reaction mixture was stirred at ambient temperature for 3 hours. After this time, water was added and the reaction mixture was extracted with ethyl acetate. The organic phase was combined and was washed with brine. The organic layer was separated, dried (Na$_2$SO$_4$), concentrated and purified by preparative TLC using a 4:1 mixture of hexane and ethyl acetate as eluent to afford the title compound (100 mg, 11% yield). $^1$H NMR (400 MHz, CDCl$_3$) δ: 7.71 (2H, m), 7.64 (2H, m), 7.51 (1H, m), 7.40 (1H, m), 7.11 (1H, m), 6.85 (1H, m), 3.93 (1H, q), 3.83 (3H, s), 3.58 (2H, m), 1.34 (3H, d). MS m/z: 468.9 [M+H]$^+$.

Example 31

[5-(2,4-dichlorophenyl)sulfanyl-4-nitro-2-thienyl]-(3-nitrophenyl)methanone: Prepared according to the procedure described for example 18 from (5-chloro-4-nitro-2-thienyl)-(3-nitrophenyl)methanone (100 mg, 0.28 mmol) and 2,4-dichlorobenzenethiol (50 mg, 0.28 mmol). The title compound was obtained as a solid (35 mg, 28% yield). $^1$H NMR (400 MHz, d$_6$-DMSO) δ: 8.52 (2H, m), 8.26 (1H, m), 8.24 (1H, m), 8.11 (1H, m) 8.04 (1H, m), 7.87 (1H, m), 7.74 (1H, m).

Example 32

Step A:
5-chloro-4-nitrothiophene-2-carbaldehyde: 5-Chlorothiophene-2-carbaldehyde (2.0 g, 13.6 mmol) was added dropwise to a stirred fuming nitric acid (13 mL) cooled to −5° C. with an ice/methanol bath. When addition was complete the stirred reaction mixture was allowed to warm slowly to 5° C. over 1 hour, then it was poured into ice/water (200 mL). The precipitated solid was collected by filtration, dissolved in dichloromethane (100 mL), washed with water and the organic layer was separated and dried (MgSO$_4$). After filtration the solvent was removed under reduced pressure and the residual brown solid was crystallised from hexane (insoluble brown material was removed by decantation of the supernatant solution), to afford title product as an off-white solid (1.51 g, 58%). $^1$H NMR (300 MHz, CDCl$_3$) δ: 9.83 (1H, s), 8.20 (1H, s).
Step B:
5-(2,4-dichlorophenylsulfanyl)-4-nitrothiophene-2-carbaldehyde: To suspension of potassium t-butyloxide (0.412 g, 3.67 mmol) in anhydrous tetrahydrofuran (20 mL), 2,4-dichlorobenzenethiol (0.6 g, 3.34 mmol) was added. The resulting mixture was stirred at ambient temperature for 15 minutes. After this time, a solution of 5-chloro-4-nitrothiophene-2-carbaldehyde (0.64 g, 3.34 mmol) in anhydrous tetrahydrofuran (5 mL) was added and the reaction mixture was stirred at ambient temperature for 2 hours. Then the above mixture was further heated under reflux for 2 hours. After this time, the reaction was cooled to ambient temperature and was poured into water (150 mL). The product was extracted into dichloromethane (3×100 mL). The organic layer was separated, washed with saturated brine (2×250 mL) and dried (MgSO$_4$). The solvent was removed under reduced pressure to give a sticky orange solid. The crude solid was purified by silica gel chromatography using an 80:20 mixture of hexane and ethyl acetate as eluent. The fractions containing the product were combined and the solvents removed in vacuo. The residual yellow solid was triturated with a small amount of hexane, collected by filtration and dried in vacuo to afford the title compound as a yellow solid (0.92 g, 82% yield). $^1$H NMR (300 MHz, CDCl$_3$) δ: 9.70 (1H, s), 8.19 (1H, s), 7.70 (1H, d, J=8.37 Hz), 7.68 (1H, d, J=2.21 Hz), 7.44 (1H, dd, J=8.37, 2.21 Hz).

Example 33

Step A:
2,5-dibromo-3-nitro-thiophene: 2,5-dibromothiophene (10.0 g, 0.0413 mol) was added in portions to nitric acid (38 mL) and concentrated sulfuric acid (75 mL) cooled at 0° C. with an ice bath. On complete addition, the reaction was removed from the cold bath and was stirred for 30 minutes before the reaction mixture was poured onto ice water (400 mL) and extracted with ethyl acetate. The organic layer was separated, dried (Na$_2$SO$_4$), concentrated under vacuum and the residue purified by silica gel chromatography to afford the title product as solid (1.6 g, 13.7% yield).
Step B:
5-bromo-2-(2,4-dichlorophenyl)sulfanyl-3-nitro-thiophene: Prepared according to the procedure described as in Step B for example 1 from 2,5-dibromo-3-nitro-thiophene (1.4 g, 4.9 mmol) and 2,4-dichlorobenzenethiol (0.877 g, 4.9 mmol). The title compound was obtained as a solid (0.56 g, 30% yield). $^1$H NMR (400 MHz, d$_6$-DMSO) δ: 8.61 (1H, s), 8.11 (1H, m), 8.03 (1H, m), 7.76 (1H, m).

Example 34

1-[5-(2,4-dichlorophenyl)sulfinyl-4-nitro-2-thienyl]ethanone: To a solution of 1-[5-(2,4-Dichlorophenylsulfanyl)-4-nitro-2-thienyl]ethanone (200 mg, 0.58 mmol) as prepared in example 2 in dichloromethane (5 mL), m-chloroperoxybenzoic acid (198 mg, 1.14 mmol) was added slowly at 0° C. The mixture was stirred at ambient temperature for 10 hours. After this time the mixture was diluted with dichloromethane (25 mL) and washed with aqueous sodium bicarbonate solution (10 mL×3), then water (10 mL×2) and brine (5 mL). The organic phase was dried (Na$_2$SO$_4$), concentrated under vacuum to afford a yellow solid as the title product (0.14 g, 67% yield). $^1$H NMR (400 MHz, d$_6$-DMSO) δ: 8.65 (1H, s), 7.96 (1H, d), 7.63 (2H, m), 2.66 (3H, s). MS m/z: 362.10 [M+H]$^+$.

Example 35

1-[5-(2,4-dichlorophenyl)sulfonyl-4-nitro-2-thienyl]ethanone: To a solution of 1-[5-(2,4-dichlorophenyl)sulfinyl-4-nitro-2-thienyl]ethanone (100 mg, 0.275 mmol) in dichloromethane (2 mL), m-chloroperoxybenzoic acid (95 mg, 0.55 mmol) was added slowly at 0° C. The mixture was stirred at ambient temperature for 10 hours. Then the mixture was diluted with dichloromethane (10 mL) and washed with aqueous sodium bicarbonate solution (5 mL×3), then water (5 mL×2) and brine (5 mL). The organic phase was dried (Na$_2$SO$_4$), concentrated under vacuum and the residue was purified by chromatography to afford the title product (75 mg, 72% yield). $^1$H NMR (400 MHz, d$_6$-DMSO) δ: 8.62 (1H, s), 8.32 (1H, d), 8.0 (1H, s), 7.87 (1H, m), 2.67 (3H, s). MS m/z: 378.1 [M+H]$^+$.

Example 36

1-[4-nitro-5-(2,3,5,6-tetrafluorophenyl)sulfanyl-2-thienyl]ethanone: Prepared by a similar procedure to that described for example 18 from the 1-(5-chloro-4-nitro-2-thienyl)ethanone (200 mg, 0.98 mmol) and 2,3,5,6-tetrafluorobenzenethiol (178 mg, 0.98 mmol) to afford the title product as a solid (60 mg, 18% yield). $^1$H NMR (400 MHz, d$_6$-DMSO) δ: 8.54 (1H, s), 8.41 (1H, m). MS m/z: 349.75 [M+H]$^+$.

Example 37

1-(4-nitro-5-quinoxalin-2-ylsulfanyl-2-thienyl)ethanone: Prepared according to the procedure described for example 18 from 1-(5-Chloro-4-nitro-2-thienyl)ethanone (250 mg, 1.215 mmol) and quinoxaline-2-thiol (197 mg, 1.215 mmol). The title compound was obtained as a solid (200 mg, 50% yield). $^1$H NMR (400 MHz, d$_6$-DMSO) δ: 9.26 (1H, s), 8.63 (1H, s), 8.01 (1H, m), 7.98 (1H, m), 2.61 (3H, s). MS m/z: 331.88 [M+H]$^+$.

Example 38

7-[(5-acetyl-3-nitro-2-thienyl)sulfanyl]-4-methyl-chromen-2-one: Prepared according to the procedure described for example 1 from 1-(5-Chloro-4-nitro-2-thienyl)ethanone (200 mg, 0.98 mmol) and 4-methyl-7-sulfanyl-chromen-2-one (188 mg, 0.98 mmol). The title compound was obtained as a solid (80 mg, 23% yield). $^1$H NMR (400 MHz, d$_6$-DMSO) δ: 8.52 (1H, s), 8.02 (1H, m), 7.92 (1H, m), 7.79 (1H, m), 6.58 (1H, s), 3.33 (3H, s), 2.50 (3H, s). MS m/z: 362.01 [M+H]$^+$.

Example 39

1-[5-[(3-chloro-4-pyridyl)sulfanyl]-4-nitro-2-thienyl]ethanone: Prepared by a similar procedure to that described for example 18 from the 1-(5-chloro-4-nitro-2-thienyl)ethanone (250 mg, 1.22 mmol) and 3-chloropyridine-4-thiol (178 mg, 1.22 mmol) to afford the title product as a solid (65 mg, 17% yield). $^1$H NMR (400 MHz, d$_6$-DMSO) δ: 8.98 (1H, s), 8.75 (1H, d), 8.57 (1H, s), 7.94 (1H, d), 2.54 (3H, s). MS m/z: 315.05 [M+H]$^+$.

Example 40

1-[5-[3,5-bis(trifluoromethyl)phenyl]sulfanyl-4-nitro-2-thienyl]ethanone: Prepared by a similar procedure to that described for example 18 from the 1-(5-chloro-4-nitro-2-thienyl)ethanone (250 mg, 1.22 mmol) and 3,5-ditrifluoromethylbenzenethiol (300 mg, 1.22 mmol) to afford the title product as a solid (325 mg, 64% yield). $^1$H NMR (400 MHz, d$_6$-DMSO) δ: 8.64 (2H, s), 8.55 (1H, s), 8.48 (1H, s), 2.52 (3H, s). MS m/z: 414.11 [M+H]$^+$.

Example 41

Step A:
Ethyl 5-chloro-4-nitrothiophene-2-carboxylate: Ethyl 5-chlorothiophene-2-carboxylate (2.7 g, 14.1 mmol) was added in portions to concentrated sulfuric acid (5 mL) and the stirred solution was cooled to below 0° C. with a methanol/ice bath. Fuming nitric acid (1.78 g, 1.2 mL, 28.3 mmol) was added slowly, keeping the temperature below 0° C. throughout the addition. On completion of addition the stirred mixture was removed from the cold bath and warmed to ambient temperature for 2 hours. The reaction was quenched by addition to ice/water (100 mL) resulting in formation of a sticky solid. The product was extracted into dichloromethane (2×100 mL). The combined organic extracts were dried (MgSO$_4$), filtered and the solvent was removed to afford an orange oil. The crude material was purified by silica gel chromatography using a 95:5 mixture of hexane and ethyl acetate as eluent to afford the title product as a solid (2.23 g, 67% yield). $^1$H NMR (CDCl$_3$) δ: 8.14 (1H, s), 4.37 (2H, q, J=7.11 Hz), 1.37 (3H, t, J=7.11 Hz).
Step B:
Ethyl 5-(2,3-dichlorophenylsulfanyl)-4-nitrothiophene-2-carboxylate: Sodium metal (0.126 g, 5.5 mmol) was dissolved in absolute ethanol (10 mL) and to the resulting solution was added 2,3-dichlorobenzenethiol (0.895 g, 5 mmol). Ethyl 5-chloro-4-nitrothiophene-2-carboxylate (1.18 g, 5 mmol) was added and the reaction mixture was stirred for 1 hour at ambient temperature and was allowed to stand overnight. After this time, the mixture was diluted with water (30 mL) and the resulting precipitate was collected by filtration and dried in vacuo at 40° C. for 1 hour. Initial analysis showed some minor impurities so the crude material was stirred in absolute ethanol (10 mL) for 30 min, collected by filtration and dried in vacuo at 40° C. for 1 hour to afford the title product as a white solid (0.67 g, 35% yield). $^1$H NMR (CDCl$_3$) δ: 8.18 (1H, s), 7.71 (2H, m), 7.31 (1H, m), 4.31 (2H, q, J=7.11 Hz), 1.33 (3H, t, J=7.11 Hz).

Example 42

Step A:
5-(2,3-dichlorophenylsulfanyl)-4-nitrothiophene-2-carboxylic acid: A solution of potassium hydroxide (72 mg, 1.27 mmol) in water (3.5 mL) was added to a suspension of ethyl 5-(2,3-dichlorophenylsulfanyl)-4-nitrothiophene-2-carboxylate (0.24 g, 0.63 mmol) in IMS (2 mL) and the resulting mixture was stirred at ambient temperature for 72 hours. After this time the mixture was diluted with water (4.5 mL) and washed the diethyl ether (2×5 mL). The aqueous phase was then acidified to pH 1 by the addition of 20% hydrochloric acid. The oil formed which solidified after stirring for 2 minutes. The mixture was left to stir for 1 hour then the solid was collected by filtration, washed with water (3×2 mL) and dried in vacuo at 40° C. overnight. The crude solid was absorbed onto silica and purified by chromatography over silica using ethyl acetate as eluent. The fractions containing the product were collected and the solvent removed under reduced pressure. The resulting solid was triturated with a small volume of diethyl ether, collected by filtration and dried in vacuo at 40° C. overnight to afford the title product as a yellow solid (58 mg, 26% yield). $^1$H NMR (d$_6$-DMSO) δ: 8.08 (1H, s), 8.00 (2H, m), 7.64 (1H, m).
Step B:
5-(2,3-dichlorophenylsulfanyl)-N-methyl-4-nitrothiophene-2-carboxamide: Thionyl chloride (0.102 g, 0.86 mmol) was added to a suspension of 5-(2,3-dichlorophenylsulfanyl)-4-nitrothiophene-2-carboxylic acid (0.15 g, 0.43 mmol) in toluene (5 mL) and the stirred mixture was heated at 80° C. for 1 hour. TLC analysis showed no acid remaining so the mixture was allowed to cool to ambient temperature and then concentrated in vacuo to give the dark brown viscous oil. The oil was dissolved in 1,4-dioxane (1 mL) and added at 5° C. to stirred 40% aqueous methylamine solution (5 mL). The mixture was stirred for 15 minutes then the resulting solid was collected by filtration, washed with water (3×1 mL) and dried in vacuo at 40° C. overnight to afford the title product as a beige solid (55 mg, 35% yield). $^1$H NMR (CDCl$_3$) δ: 7.84 (1H, s) 7.70 (2H, m), 7.36 (1H, m), 6.01 (1H, broad s), 2.95 (3H, d, J=4.9 Hz).

Example 43

Methyl 5-[(3,5-dichloro-4-pyridyl)sulfanyl]-4-nitro-thiophene-2-carboxylate: 3,5-dichloropyridine-4-thiol sodium salt prepared as in example 17 (0.179 g, 1 mmol), methyl 5-chloro-4-nitro-thiophene-2-carboxylate (221 mg, 1 mmol) was mixed in toluene (5 mL). Then potassium carbonate (0.207 g, 1.5 mmol) was added. The resulting reaction mixture was stirred at ambient temperature for 4 hours. After this time, the reaction mixture was filtered and diluted with ethyl acetate. The organic solution was washed with water (2 mL×2), brine (2 mL×2), dried (Na$_2$SO$_4$), and concentrated under vacuum. The residue was purified by silica gel chromatography eluting with a 96:4 mixture of hexane and ethyl acetate to afford the title product as a solid (82.5 mg, 23% yield). $^1$H NMR (300 MHz, d$_6$-DMSO) δ: 9.05 (2H, s), 8.20 (1H, s), 3.82 (3H, s). MS m/z: 365.2 [M+H]$^+$.

Example 44

Step A:
5-[(3,5-dichloro-4-pyridyl)sulfanyl]-4-nitro-thiophene-2-carboxylic acid: An aqueous solution of sodium hydroxide (1N, 1.5 mL, 1.5 mmol) was added to a solution of Methyl 5-[(3,5-dichloro-4-pyridyl)sulfanyl]-4-nitro-thiophene-2-carboxylate (0.275 g, 0.75 mmol) in tetrahydrofuran (5 mL), and the resulting mixture was stirred at ambient temperature for 4 hours. After this time the mixture was diluted with water (4.5 mL) and washed the ethyl ether (2×5 mL). The aqueous phase was then acidified to pH 5 by the addition of hydrochloric acid solution (1 M), then the product was extracted into ethyl acetate (5×5 mL), dried (Na$_2$SO$_4$) and the solvent removed under reduced pressure to afford the title product as a white solid (123 mg, 47% yield). $^1$H NMR (300 MHz, d$_6$-DMSO) δ: 9.0 (2H, s), 8.1 (1H, s). MS m/z: 350.85, 352.90 [M+H]$^+$.
Step B:
5-[(3,5-dichloro-4-pyridyl)sulfanyl]-N-isopropyl-4-nitro-thiophene-2-carboxamide: Chloro-1,1,3,3-tetramethyluronium hexachloroantimonate (47 mg, 0.1 mmol) was added to a suspension of 5-[(3,5-dichloro-4-pyridyl)sulfanyl]-4-nitro-thiophene-2-carboxylic acid (39 mg, 0.11 mmol) in dichloromethane (1 mL) and the mixture was stirred at ambient temperature for 10 min. A solution of isopropylamine (9 mg, 0.12 mmol) and triethylamine (12 mg, 0.12 mmol) in dichloromethane (0.5 mL) was added to the above mixture and was stirred at ambient temperature for over night. After passing through a ISOLUTE™ PE-AX cartridge to remove excess amines, the resulting mixture was concentrated and the residue was purified by reverse-phase HPLC to afford the title product as a white solid (25 mg, 49% yield). $^1$H NMR (300 MHz, d$_6$-DMSO) δ: 9.0 (2H, s), 8.65 (1H, d), 8.50 (1H, s), 4.0 (1H, m), 1.25 (6H, d). MS m/z: 391.70, 393.80 [M+H]$^+$.

Example 45

N-benzyl-5-[(3,5-dichloro-4-pyridyl)sulfanyl]-4-nitro-thiophene-2-carboxamide: Prepared according to the procedure described for example 44 from 5-[(3,5-dichloro-4-pyridyl)sulfanyl]-4-nitro-thiophene-2-carboxylic acid (39 mg, 0.11 mmol) and benzylamine (13 mg, 0.12 mmol). The title product was obtained as a yellow solid (15 mg, 28% yield). $^1$H NMR (300 MHz, d$_6$-DMSO) δ: 8.72 (1H, s), 8.71 (1H, s), 8.35-8.39 (3H, m), 7.31 (2H, m), 7.27 (2H, m), 2.6 (2H, m). MS m/z: 439.85, 441.80 [M+H]$^+$.

Example 46

5-[(3,5-dichloro-4-pyridyl)sulfanyl]-4-nitro-thiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and ammonia (0.24 mL, 0.5 M in THF, 0.12 mmol). The title compound was obtained as a solid (4.5 mg, 12.8% yield). MS m/z: 347.80, 349.80 [M+H]$^+$.

Example 47

5-[(3,5-dichloro-4-pyridyl)sulfanyl]-N-(2-hydroxyethyl)-4-nitro-thiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 2-hydroxylethylamine (17.6 mg, 0.12 mmol). The title compound was obtained as a solid (7.8 mg, 17.0% yield). MS m/z: 347.80, 349.80 [M+H]$^+$.

Example 48

5-[(3,5-dichloro-4-pyridyl)sulfanyl]-N-(2-dimethylaminoethyl)-4-nitro-thiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and N',N'-dimethyl-ethane-1,2-diamine (7.3 mg, 0.12 mmol). The title compound was obtained as a solid (5.8 mg, 14.8% yield). MS m/z: 421.90, 423.90 [M+H]$^+$.

Example 49

5-[(3,5-dichloro-4-pyridyl)sulfanyl]-N,N-dimethyl-4-nitro-thiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and dimethylamine (4.5 mg, 0.12 mmol). The title compound was obtained as a solid (5.8 mg, 16.0% yield). MS m/z: 378.90, 380.80 [M+H]$^+$.

Example 50

Step A:
5-[(3,5-dichloro-4-pyridyl)sulfanyl]-4-nitro-thiophene-2-carboxylic acid: Ethyl 5-[(3,5-dichloro-4-pyridyl)sulfanyl]-4-nitro-thiophene-2-carboxylate (1.8 g, 4.74 mmol) was added to a solution of concentrated sulfuric acid (10 mL) diluted with water (20 mL), and the resulting mixture was heated at 100° C. for 5 hours. After this time, the mixture was poured into ice (4.5 mL) and stirred at room temperature for 20 minutes, then the resulting solid was collected by filtration, washed with water and dried in vacuo at 40° C. overnight to afford the title product as a white solid (1.3 g, 78% yield). $^1$H NMR (400 MHz, d$_6$-DMSO) δ: 9.0 (2H, s), 8.1 (1H, s). MS m/z: 350.85, 352.90 [M+H]$^+$.
Step B:
5-((3,5-dichloropyridin-4-yl)thio)-N-(2-(methylthio) ethyl)-4-nitrothiophene-2-carboxamide: Oxalyl chloride (0.934 g, 3.92 mmol) followed by N,N-dimethylformide (0.1 mL) was added dropwise to a suspension of 5-[(3,5-dichloro-4-pyridyl)sulfanyl]-4-nitro-thiophene-2-carboxylic acid (0.60 g, 1.71 mmol) in dichloromethane (30 mL) and the mixture was stirred at ambient temperature for 8 hour. After this time, TLC analysis showed no acid remaining so the mixture was allowed to be concentrated in vacuo to give a yellow solid. The resulting acid chloride solid was dissolved in dry tetrahydrofuran (10 mL). 2-(methylthio)ethanamine (0.047 g, 0.52 mmol) followed by triethylamine (0.066 g, 0.65 mmol) was added to a 2.5 mL aliquot of acid chloride solution in tetrahydrofuran at 0° C. The resulting mixture was stirred at ambient temperature for 3 hours. TLC analysis showed no acid chloride remaining so the mixture was diluted with ethylacetate and washed with water and brine. The organic layer was separated, dried (Na$_2$SO$_4$), filtered and the solvent was removed to afford a brown oil. The crude material was purified by silica gel chromatography using an 85:15 mixture of hexane and ethyl acetate as eluent to afford the title product as a brown solid (55 mg, 13% yield). $^1$H NMR (400 MHz, d$_6$-DMSO) δ: 8.99 (1H, m), 8.98 (2H, m), 8.41 (1H, s), 3.39 (2H, m), 2.59 (2H, m), 2.08 (3H, s). MS m/z: 422.20, 424.21 [M+H]$^+$.

Example 51

5-((3,5-dichloropyridin-4-yl)thio)-N-(2-methoxybenzyl)-4-nitrothiophene-2-carboxamide: Prepared according to the procedure described for example 50 from 5-[(3,5-dichloro-4-pyridyl)sulfanyl]-4-nitro-thiophene-2-carboxylic acid (0.1 mg, 0.28 mmol) and 2-methoxy-benzylamine (46 mg, 0.33 mmol). The title compound was obtained as a yellow solid (25.0 mg, 19.0% yield). $^1$H NMR (400 MHz, $d_6$-DMSO) δ: 9.20 (1H, m), 8.98 (2H, s), 8.58 (1H, s), 7.25 (1H, m), 7.18 (1H, m), 7.00 (1H, m), 6.90 (1H, m), 4.36 (2H, m), 3.79 (3H, s). MS m/z: 468.05, 470.05 [M+H]$^+$.

Example 52

5-((3,5-dichloropyridin-4-yl)thio)-N-(furan-2-ylmethyl)-4-nitrothiophene-2-carboxamide:
Prepared according to the procedure described for example 50 from 5-[(3,5-dichloro-4-pyridyl)sulfanyl]-4-nitro-thiophene-2-carboxylic acid (100 mg, 0.27 mmol) and Furfuryl amine (31 mg, 0.32 mmol). The title compound was obtained as a solid (45 mg, 39% yield). $^1$H NMR (400 MHz, $d_6$-DMSO) δ: 9.34 (1H, m), 8.99 (2H, m), 8.48 (1H, s), 7.58 (1H, m), 6.39 (1H, m), 6.29 (1H, m), 4.39 (2H, m). MS m/z: 428.04, 429.99 [M+H]$^+$.

Example 53

5-((3,5-dichloropyridin-4-yl)thio)-N-(2-methoxyethyl)-4-nitrothiophene-2-carboxamide: Prepared according to the procedure described for example 50 from 5-[(3,5-dichloro-4-pyridyl)sulfanyl]-4-nitro-thiophene-2-carboxylic acid (100 mg, 0.28 mmol) and 2-Methoxy ethylamine (25 mg, 0.32 mmol). The title compound was obtained as a solid (52 mg, 46% yield). $^1$H NMR (400 MHz, $d_6$-DMSO) δ: 8.99 (2H, m), 8.95 (1H, m), 8.46 (1H, m), 3.39 (2H, m), 3.35 (2H, m), 3.24 (3H, s). MS m/z: 405.99, 407.99 [M+H]$^+$.

Example 54

5-((3,5-dichloropyridin-4-yl)thio)-4-nitro-N-(2-phenoxyethyl)thiophene-2-carboxamide: Prepared according to the procedure described for example 50 from 5-[(3,5-dichloro-4-pyridyl)sulfanyl]-4-nitro-thiophene-2-carboxylic acid (100 mg, 0.28 mmol) and 2-Phenoxy ethylamine (45 mg, 0.32 mmol). The title compound was obtained as a solid (32 mg, 24% yield). $^1$H NMR (400 MHz, $d_6$-DMSO) δ: 9.11 (1H, m), 8.99 (2H, m), 8.47 (1H, s), 7.27 (2H, m), 6.93 (3H, m), 4.04 (2H, m), 3.56 (2H, m). MS m/z: 468.03, 470.03 [M+H]$^+$.

Example 55

5-((3,5-dichloropyridin-4-yl)thio)-4-nitro-N-(2-(thiophen-2-yl)ethyl)thiophene-2-carboxamide: Prepared according to the procedure described for example 50 from 5-[(3,5-dichloro-4-pyridyl)sulfanyl]-4-nitro-thiophene-2-carboxylic acid (100 mg, 0.28 mmol) and Thiophene-2-ethylamine (41 mg, 0.32 mmol). The title compound was obtained as a solid (35 mg, 27% yield). $^1$H NMR (400 MHz, $d_6$-DMSO) δ: 9.00 (1H, m), 8.99 (2H, m), 8.41 (1H, s), 7.33 (1H, m), 6.94 (2H, m), 3.44 (2H, m), 3.02 (2H, m). MS m/z: 458.00, 459.99 [M+H]$^+$.

Example 56

5-((3,5-dichloropyridin-4-yl)thio)-N-((3-methylthiophen-2-yl)methyl)-4-nitrothiophene-2-carboxamide: Prepared according to the procedure described for example 50 from 5-[(3,5-dichloro-4-pyridyl)sulfanyl]-4-nitro-thiophene-2-carboxylic acid (100 mg, 0.28 mmol) and 3-methylthiophene-2-methyllamine (41 mg, 0.32 mmol). The title compound was obtained as a solid (41 mg, 32% yield). $^1$H NMR (400 MHz, $d_6$-DMSO) δ: 9.35 (1H, m), 8.98 (2H, m), 8.45 (1H, s), 7.30 (1H, m), 6.83 (1H, m), 4.47 (2H, m), 2.20 (3H, s). MS m/z: 458.02, 459.98 [M+H]$^+$.

Example 57

N-(3-chlorobenzyl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carboxylic acid (100 mg, 0.28 mmol) and 3-chloro benzylamine (45 mg, 0.32 mmol). The title compound was obtained as a solid (66 mg, 50% yield). $^1$H NMR (400 MHz, $d_6$-DMSO) δ: 9.41 (1H, m), 8.98 (2H, m), 8.47 (1H, s), 7.34 (3H, m), 7.24 (1H, m), 4.39 (2H, m). MS m/z: 471.98, 473.99 [M+H]$^+$.

Example 58

N-([1,1'-biphenyl]-3-ylmethyl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carboxylic acid (100 mg, 0.28 mmol) and 3-phenyl benzylamine (55 mg, 0.32 mmol). The title compound was obtained as a solid (24 mg, 17% yield). $^1$H NMR (400 MHz, CDCl$_3$) δ: 8.74 (2H, m), 7.86 (1H, s), 7.55 (3H, m), 7.53 (1H, m), 7.46 (3H, m), 7.38 (1H, m), 7.26 (1H, m), 6.27 (1H, m), 4.63 (2H, m). MS m/z: 514.07, 516.04 [M+H]$^+$.

Example 59

5-((3,5-dichloropyridin-4-yl)thio)-N-(2-morpholinoethyl)-4-nitrothiophene-2-carboxamide: Prepared according to the procedure described for example 50 from 5-[(3,5-dichloro-4-pyridyl)sulfanyl]-4-nitro-thiophene-2-carboxylic acid (100 mg, 0.28 mmol) and 4-(2-aminoethyl) morpholine (42 mg, 0.32 mmol). The title compound was obtained as a solid (49 mg, 38% yield). $^1$H NMR (400 MHz, $d_6$-DMSO) δ: 8.98 (2H, m), 8.83 (1H, m), 8.43 (1H, s), 4.02 (4H, m), 3.31 (2H, m), 2.45 (2H, m), 2.38 (4H, m). MS m/z: 463.06, 465.05 [M+H]$^+$.

Example 60

N-(2-chlorobenzyl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carboxylic acid (100 mg, 0.28 mmol) and 2-chloro benzylamine (45 mg, 0.32 mmol). The title compound was obtained as a solid (29 mg, 22% yield). $^1$H NMR (400 MHz, $d_6$-DMSO) δ: 9.36 (1H, m), 8.98 (2H, m), 8.53 (1H, s), 7.45 (1H, m), 7.33 (3H, m), 4.46 (2H, m). MS m/z: 471.97, 473.95 [M+H]$^+$.

Example 61

(5-((3,5-dichloropyridin-4-yl)thio)-4-nitrothiophen-2-yl)(4-(2-hydroxyethyl)piperazin-1-yl)methanone: Prepared according to the procedure described for example 44 from 5-[(3,5-dichloro-4-pyridyl)sulfanyl]-4-nitro-thiophene-2-carboxylic acid (35 mg, 0.1 mmol) and 2-piperazin-1-yletha-nol (26.0 mg, 0.2 mmol). The title compound was obtained as a solid (23.0 mg, 50% yield). ¹H NMR (300 MHz, $d_6$-DMSO) δ: 8.75 (2H, s), 7.80 (1H, s), 4.87 (4H, m), 4.23 (4H, m), 4.04 (2H, m), 3.22 (2H, m). MS m/z: 462.90, 464.90 [M+H]⁺.

Example 62 tert-butyl 2-(5-((3,5-dichloropyridin-4-yl)thio)-4-nitrothiophene-2-carboxamido)acetate: Prepared according to the procedure described for example 44 from 5-[(3,5-dichloro-4-pyridyl)sulfanyl]-4-nitro-thiophene-2-carboxylic acid (145 mg, 0.5 mmol) and tert-butyl 2-aminoacetate (79 mg, 0.6 mmol). The title compound was obtained as a solid (98.0 mg, 42% yield). ¹H NMR (300 MHz, $d_6$-DMSO) δ: 8.74 (2H, s), 7.95 (1H, s), 4.06 (2H, m), 1.49 (9H, s) MS m/z: 463.80, 465.75 [M+H]⁺.

Example 63

N-([1,1'-biphenyl]-4-ylmethyl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carboxylic acid (100 mg, 0.28 mmol) and 4-phenyl benzylamine (55 mg, 0.32 mmol). The title compound was obtained as a yellow solid (65 mg, 45% yield). ¹H NMR (400 MHz, $d_6$-DMSO) δ: 9.41 (1H, m), 8.98 (2H, m), 8.49 (1H, s), 7.63 (4H, m), 7.46 (2H, m), 7.35 (3H, m), 7.38 (1H, m), 4.44 (2H, m). MS m/z: 514.03, 516.08 [M+H]⁺

Example 64

5-((3,5-dichloropyridin-4-yl)thio)-N-(2-(4-methylpiperazin-1-yl)ethyl)-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 2-(4-methylpiperazin-1-yl)ethanamine (16 mg, 0.12 mmol). The title compound was obtained as a solid (13.6 mg, 29% yield). MS m/z: 476.04, 478.04 [M+H]⁺.

Example 65

Prepared according to the procedure described for example 44 from 5-[(3,5-dichloro-4-pyridyl)sulfanyl]-4-nitro-thiophene-2-carboxylic acid (70 mg, 0.2 mmol) and 3-(4-methylpiperazin-1-yl)propan-1-amine (42.6 mg, 0.25 mmol). The title compound was obtained as a solid (76.0 mg, 78% yield). MS m/z: 490.04, 492.04 [M+H]⁺.

Example 66

(5-((3,5-dichloropyridin-4-yl)thio)-4-nitrothiophen-2-yl)(4-methylpiperazin-1-yl)methanone: Prepared according to the procedure described for example 44 from 5-[(3,5-dichloro-4-pyridyl)sulfanyl]-4-nitro-thiophene-2-carboxylic acid (35 mg, 0.1 mmol) and 1-methylpiperazine (10.0 mg, 0.1 mmol). The title compound was obtained as a solid (26.5 mg, 61% yield). MS m/z: 433 [M+H]⁺.

Example 67

5-((3,5-dichloropyridin-4-yl)thio)-N-(3-methoxybenzyl)-N-methyl-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 1-(3-methoxyphenyl)-N-methyl-methanamine (18.0 mg, 0.12 mmol). The title compound was obtained as a solid (18.5 mg, 38% yield). MS m/z: 484.01, 486.01 [M+H]⁺.

Example 68

5-((3,5-dichloropyridin-4-yl)thio)-4-nitro-N-(3-(trifluoromethoxy)benzyl)thiophene-2-carboxamide: Prepared according to the procedure described for example 50 from 5-[(3,5-dichloro-4-pyridyl)sulfanyl]-4-nitro-thiophene-2-carboxylic acid (145 mg, 0.41 mmol) and 3-(trifluoromethoxy)benzylamine (53 mg, 0.39 mmol). The title compound was obtained as a solid (55 mg, 26% yield). ¹H NMR (400 MHz, $d_6$-DMSO) δ: 9.45 (1H, m), 8.98 (2H, m), 8.47 (1H, s), 7.48 (2H, m), 7.30 (2H, m), 4.45 (2H, m). MS m/z: 522.09, 524.08 [M+H]⁺.

Example 69

5-((3,5-dichloropyridin-4-yl)thio)-N-(3,5-dimethoxybenzyl)-4-nitrothiophene-2-carboxamide: Prepared according to the procedure described for example 50 from 5-[(3,5-dichloro-4-pyridyl)sulfanyl]-4-nitro-thiophene-2-carboxylic acid (145 mg, 0.41 mmol) and 3,5-dimethoxy benzylamine (65 mg, 0.39 mmol). The title compound was obtained as a solid (55 mg, 34% yield). ¹H NMR (400 MHz, $d_6$-DMSO) δ: 9.35 (1H, m), 8.98 (2H, m), 8.48 (1H, s), 6.43 (2H, m), 6.38 (1H, m), 4.32 (2H, m), 3.70 (6H, m). MS m/z: 498.16, 500.08 [M+H]⁺.

Example 70

5-((3,5-dichloropyridin-4-yl)thio)-N-((2,3-dihydrobenzofuran-5-yl)methyl)-4-nitrothiophene-2-carboxamide: 2-(7-Aza-1H-benzotriazole-1-yl)-1,1,3,3-tetramethyluronium hexafluorophosphate (76.4 mg, 0.51 mmol), 2,3-dihydrobenzofuran-5-ylmethanamine (165.5 mg, 1.28 mmol) and diisopropylethylamine (12 mg, 0.12 mmol) was added to a suspension of 5-[(3,5-dichloro-4-pyridyl)sulfanyl]-4-nitro-thiophene-2-carboxylic acid (150 mg, 0.43 mmol) in dichloromethane (3 mL) and the resulting mixture was stirred at ambient temperature for 6 hours. TLC analysis showed no acid remaining so the mixture was diluted with dichloromethane and washed with water and brine. The organic layer was dried ($Na_2SO_4$), filtered and the solvent was removed to afford a solid. The crude material was purified by silica gel chromatography using a 70:30 mixture of hexane and ethyl acetate as eluent to afford the title product as a brown solid (11 mg, 5% yield). ¹H NMR (400 MHz, $d_6$-DMSO) δ: 9.28 (1H, m), 8.99 (2H, m), 8.46 (1H, s), 7.14 (1H, m), 7.00 (1H, m), 6.69 (1H, m), 4.48 (2H, m), 4.30 (2H, m), 3.15 (2H, m). MS m/z: 480.11, 482.11 [M+H]⁺.

Example 71

5-((3,5-dichloropyridin-4-yl)thio)-4-nitro-N-(3-phenyl-1H-pyrazol-5-yl)thiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 3-phenyl-1H-pyrazol-5-amine (16.0 mg, 0.12 mmol). The title compound was obtained as a solid (22.7 mg, 46.0% yield). MS m/z: 491.97, 493.97 [M+H]⁺.

Example 72

1-(5-((3,5-dichloropyridin-4-yl)thio)-4-nitrothiophene-2-carbonyl)piperidine-4-carboxamide: Prepared according to the procedure described for example 70 from 5-[(3,5-dichloro-4-pyridyl)sulfanyl]-4-nitro-thiophene-2-carboxylic acid (150 mg, 0.43 mmol) and nipecotamide (66 mg, 0.51 mmol). The title compound was obtained as a solid (120 mg, 54% yield). $^1$H NMR (400 MHz, d$_6$-DMSO) δ: 8.98 (2H, m), 7.93 (1H, s), 7.28 (1H, m), 6.82 (1H, m), 4.15 (2H, m), 2.36 (1H, m), 1.76 (2H, m), 1.48 (2H, m). MS m/z: 519.32, 521.38 [M+H]$^+$.

Example 73

(5-((3,5-dichloropyridin-4-yl)thio)-4-nitrothiophen-2-yl)(4-(hydroxymethyl)piperidin-1-yl)methanone: Prepared according to the procedure described for example 70 from 5-[(3,5-dichloro-4-pyridyl)sulfanyl]-4-nitro-thiophene-2-carboxylic acid (150 mg, 0.43 mmol) and piperidin-4-yl-methanol (59 mg, 0.51 mmol). The title compound was obtained as a solid (70 mg, 36% yield). $^1$H NMR (400 MHz, d$_6$-DMSO) δ: 8.98 (2H, m), 7.89 (1H, s), 4.50 (1H, m), 4.25 (2H, m), 3.24 (2H, m), 1.68 (3H, m), 1.09 (2H, m). MS m/z: 448.34, 450.34 [M+H]$^+$.

Example 74

(5-((3,5-dichloropyridin-4-yl)thio)-4-nitrothiophen-2-yl)(4-fluoropiperidin-1-yl)methanone: Prepared according to the procedure described for example 70 from 5-[(3,5-dichloro-4-pyridyl)sulfanyl]-4-nitro-thiophene-2-carboxylic acid (150 mg, 0.43 mmol) and 3-fluorobenzylamine (53 mg, 0.51 mmol). The title compound was obtained as a solid (102 mg, 54% yield). $^1$H NMR (400 MHz, d$_6$-DMSO) δ: 8.98 (2H, m), 7.96 (1H, s), 3.64 (4H, m), 1.95 (2H, m), 1.76 (2H, m). MS m/z: 436.19, 438.22 [M+H]$^+$.

Example 75

N-((1r,3r,5r,7r)-adamantan-2-yl)-5-((3,5-dichloropyridin-4-yl)thio)-4-nitrothiophene-2-carboxamide: Prepared according to the procedure described for example 70 from 5-[(3,5-dichloro-4-pyridyl)sulfanyl]-4-nitro-thiophene-2-carboxylic acid (150 mg, 0.43 mmol) and 2-adamantan amine (77 mg, 0.51 mmol). The title compound was obtained as a solid (60 mg, 29% yield). $^1$H NMR (400 MHz, d$_6$-DMSO) δ: 8.98 (2H, m), 8.81 (1H, s), 8.29 (1H, m), 3.94 (1H, m), 2.07 (2H, m), 1.98 (2H, m), 1.78 (6H, m), 1.69 (2H, m), 1.50 (2H, m). MS m/z: 484.30, 486.33 [M+H]$^+$.

Example 76

N-((3s,5s,7s)-adamantan-1-yl)-5-((3,5-dichloropyridin-4-yl)thio)-4-nitrothiophene-2-carboxamide: Prepared according to the procedure described for example 70 from 5-[(3,5-dichloro-4-pyridyl)sulfanyl]-4-nitro-thiophene-2-carboxylic acid (150 mg, 0.43 mmol) and 1-adamantyl amine (78 mg, 0.51 mmol). The title compound was obtained as a solid (22 mg, 11% yield). $^1$H NMR (400 MHz, d$_6$-DMSO) δ: 8.98 (2H, m), 8.59 (1H, s), 8.10 (1H, m), 1.99 (9H, m), 1.72 (6H, m). MS m/z: 482.23, 484.26 [M+H]$^+$.

Example 77

5-((3,5-dichloropyridin-4-yl)thio)-N-(4-hydroxycyclohexyl)-4-nitrothiophene-2-carboxamide: Prepared according to the procedure described for example 70 from 5-[(3,5-dichloro-4-pyridyl)sulfanyl]-4-nitro-thiophene-2-carboxylic acid (150 mg, 0.43 mmol) and trans-4-aminocyclohexanol (59 mg, 0.51 mmol). The title compound was obtained as a solid (45 mg, 23% yield). $^1$H NMR (400 MHz, d$_6$-DMSO) δ: 8.98 (2H, m), 8.58 (1H, m), 8.47 (1H, s), 4.56 (1H, d), 3.55 (1H, m), 3.37 (1H, m), 1.78 (4H, m), 1.20 (6H, m). MS m/z: 446.19, 448.18 [M+H]$^+$.

Example 78

5-((3,5-dichloropyridin-4-yl)thio)-4-nitro-N-(quinolin-8-yl)thiophene-2-carboxamide: Prepared according to the procedure described for example 70 from 5-[(3,5-dichloro-4-pyridyl)sulfanyl]-4-nitro-thiophene-2-carboxylic acid (150 mg, 0.43 mmol) and 8-amino quinoline (74 mg, 0.51 mmol). The title compound was obtained as a yellow solid (20 mg, 10% yield). $^1$H NMR (400 MHz, d$_6$-DMSO) δ: 10.83 (1H, m), 9.01 (3H, m), 8.83 (1H, m), 8.47 (1H, m), 8.28 (1H, m), 7.82 (1H, m), 7.66 (2H, m), 1.25 (1H, m). MS m/z: 477.23, 479.23 [M+H]$^+$.

Example 79

5-((3,5-dichloropyridin-4-yl)thio)-N-(4-(4-methylpiperazin-1-yl)phenyl)-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 4-(4-methylpiperazin-1-yl)aniline (19.0 mg, 0.12 mmol). The title compound was obtained as a solid (10.0 mg, 19% yield). MS m/z: 524.00, 526.00 [M+H]$^+$.

Example 80

(5-((3,5-dichloropyridin-4-yl)thio)-4-nitrothiophen-2-yl)(4,4-dimethylpiperidin-1-yl)methanone: Prepared according to the procedure described for example 50 from 5-[(3,5-dichloro-4-pyridyl)sulfanyl]-4-nitro-thiophene-2-carboxylic acid (200 mg, 0.56 mmol) and 4,4-dimethyl piperidine (83 mg, 0.65 mmol). The title compound was obtained as a solid (34 mg, 14% yield). $^1$H NMR (400 MHz, d$_6$-DMSO) δ: 8.97 (2H, s), 7.90 (1H, s), 3.57 (4H, m), 1.33 (4H, m), 0.95 (6H, s). MS m/z: 446.21, 448.23 [M+H]$^+$.

Example 81

Step A:
methyl 5-((2,4-dichlorophenyl)thio)-4-nitrothiophene-2-carboxylate: Prepared according to the procedure described for step A of example 18 from 2,4-dichloro-phenol (0.6 mL, 4.52 mmol) and methyl 5-chloro-4-nitro-thiophene-2-carboxylate (1.0 g, 4.52 mmol). The title compound was obtained as a white solid (1.2 g, 65% yield). $^1$H NMR (400 MHz, d$_6$-DMSO) δ: 8.17 (1H, m), 8.08 (1H, m), 8.01 (1H, m), 7.73 (1H, m), 3.78 (3H, s).
Step B:
5-((2,4-dichlorophenyl)thio)-4-nitrothiophene-2-carboxylic acid: Prepared according to the procedure described for step A of example 44 from methyl 5-(2,4-dichlorophenoxy)-4-nitrothiophene-2-carboxylate (1.45 g, 4.0 mmol). The title compound was obtained as a white solid (1.15 g, 83%). $^1$H NMR (400 MHz, d$_6$-DMSO) δ: 8.07 (1H, m), 8.06 (1H, m), 7.72 (1H, m). MS m/z: 348.04, 350.02 [M+H]$^+$.
Step C:
5-((2,4-dichlorophenyl)thio)-N-(1-methylpiperidin-4-yl)-4-nitrothiophene-2-carboxamide: Prepared according to the procedure described for example 70 from 5-((3,5-dichloropyridin-4-yl)thio)-4-nitrothiophene-2-carboxylic acid (150 mg, 0.43 mmol) and 1-methylpiperidin-4-amine (58 mg, 0.52 mmol). The title compound was obtained as a solid (34 mg, 18% yield). $^1$H NMR (400 MHz, d$_6$-DMSO) δ: 8.59 (1H, d), 8.45 (1H, s), 8.05 (1H, d), 7.98 (1H, d), 7.68 (1H, m), 3.59 (1H, m), 2.73 (2H, m), 2.15 (3H, s), 1.94 (2H, m), 1.73 (2H, m), 1.51 (2H, m). MS m/z: 446.29, 448.32 [M+H]$^+$.

Example 82

5-((2,4-dichlorophenyl)thio)-4-nitro-N-(3-(2-oxopyrrolidin-1-yl)propyl)thiophene-2-carboxamide: Prepared according to the procedure described for example 70 from 5-((3,5-dichloropyridin-4-yl)thio)-4-nitrothiophene-2-carboxylic acid from step B of example 81 (150 mg, 0.43 mmol) and 1-(3-amino-propyl)-2-pyrrolidinone (73 mg, 0.52 mmol). The title compound was obtained as a solid (45 mg, 22% yield). $^1$H NMR (400 MHz, d$_6$-DMSO) δ: 8.77 (1H, m), 8.36 (1H, s), 8.05 (1H, d), 7.98 (1H, d), 7.68 (1H, m), 3.31 (2H, m), 3.17 (4H, m), 2.18 (2H, m), 1.89 (2H, m), 1.67 (2H, m). MS m/z: 474.03, 476.04 [M+H]$^+$.

Example 83

(5-((3,5-dichloropyridin-4-yl)thio)-4-nitrothiophen-2-yl)(3-hydroxypiperidin-1-yl)methanone: Prepared according to the procedure described for example 70 from 5-[(3,5-dichloro-4-pyridyl)sulfanyl]-4-nitro-thiophene-2-carboxylic acid (150 mg, 0.43 mmol) and 3-hydroxyl piperidine (52 mg, 0.52 mmol). The title compound was obtained as a solid (22 mg, 12% yield). $^1$H NMR (400 MHz, d$_6$-DMSO) δ: 8.97 (2H, m), 7.99 (1H, m), 4.96 (1H, m), 3.61 (3H, m), 1.72 (2H, m), 1.49 (2H, m). MS m/z: 434.08, 436.03 [M+H]$^+$.

Example 84

N-(2-(1-benzylpyrrolidin-3-yl)ethyl)-5-((3,5-dichloropyridin-4-yl)thio)-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 4-(aminomethyl)-1-methylpiperidin-4-ol (25 mg, 0.1 mmol). The title compound was obtained as a solid (12.0 mg, 22% yield). MS m/z: 537.06, 539.06 [M+H]$^+$.

Example 85 tert-butyl 4-(5-((3,5-dichloropyridin-4-yl)thio)-4-nitrothiophene-2-carboxamido)piperidine-1-carboxylate: Prepared according to the procedure described for example 50 from 5-[(3,5-dichloro-4-pyridyl)sulfanyl]-4-nitrothiophene-2-carboxylic acid (3.0 g, 8.5 mmol) and tert-butyl 4-aminopiperidine-1-carboxylate (2.2 g, 10.0 mmol). The title compound was obtained as a solid (3.3 g, 73% yield). $^1$H NMR (400 MHz, d$_6$-DMSO) δ: 8.98 (2H, s), 8.66 (1H, m), 8.47 (1H, m), 3.87 (3H, m), 2.82 (2H, m), 1.73 (2H, m), 1.37 (9H, s), 1.31 (2H, m).

Example 86

5-((3,5-dichloropyridin-4-yl)thio)-N-(4-(dimethylamino)phenyl)-4-nitrothiophene-2-carboxamide: Prepared according to the procedure described for example 50 from 5-[(3,5-dichloro-4-pyridyl)sulfanyl]-4-nitro-thiophene-2-carboxylic acid (200 mg, 0.57 mmol) and N,N'-dimethylbenzen-1,4-diamine (93 mg, 0.68 mmol). The title compound was obtained as a solid (45 mg, 17% yield). $^1$H NMR (400 MHz, d$_6$-DMSO) δ: 10.30 (1H, m), 8.99 (2H, m), 8.64 (1H, s), 7.45 (2H, m), 6.72 (2H, m), 2.86 (6H, s). MS m/z: 467.25, 469.27 [M+H]$^+$.

Example 87

5-((3,5-dichloropyridin-4-yl)thio)-N-(4-methylthiazol-2-yl)-4-nitrothiophene-2-carboxamide: Prepared according to the procedure described for example 70 from 5-[(3,5-dichloro-4-pyridyl)sulfanyl]-4-nitro-thiophene-2-carboxylic acid (200 mg, 0.57 mmol) and 4-methyl-thiazol-2-amine (78 mg, 0.68 mmol). The title compound was obtained as a yellow solid (65 mg, 26% yield). $^1$H NMR (400 MHz, d$_6$-DMSO) δ: 9.01 (2H, m), 7.24 (1H, m), 6.88 (1H, m), 2.23 (3H, m). MS m/z: 446.92, 448.97 [M+H]$^+$.

Example 88

5-((3,5-dichloropyridin-4-yl)thio)-N-(4,5-dimethylthiazol-2-yl)-4-nitrothiophene-2-carboxamide: Prepared according to the procedure described for example 70 from 5-[(3,5-dichloro-4-pyridyl)sulfanyl]-4-nitro-thiophene-2-carboxylic acid (200 mg, 0.57 mmol) and 4,5-dimethyl-thiazol-2-amine (87 mg, 0.68 mmol). The title compound was obtained as a yellow solid (8 mg, 3% yield). $^1$H NMR (400 MHz, d$_6$-DMSO) δ: 12.85 (1H, m), 9.01 (2H, m), 2.08 (6H, m). MS m/z: 459.03, 461.02 [M+H]$^+$.

Example 89

Prepared according to the procedure described for example 70 from 5-[(3,5-dichloro-4-pyridyl)sulfanyl]-4-nitro-thiophene-2-carboxylic acid (200 mg, 0.57 mmol) and 5-methyl-thiazol-2-amine (78 mg, 0.68 mmol). The title compound was obtained as a yellow solid (65 mg, 26% yield). $^1$H NMR (400 MHz, d$_6$-DMSO) δ: 12.91 (1H, br), 9.01 (2H, m), 7.20 (1H, m), 2.21 (3H, s). MS m/z: 447.08, 448.99 [M+H]$^+$.

Example 90

5-((3,5-dichloropyridin-4-yl)thio)-N-((4-hydroxy-1-methylpiperidin-4-yl)methyl)-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 4-(aminomethyl)-1-methylpiperidin-4-ol (14.4 mg, 0.1 mmol). The title compound was obtained as a solid (15.2 mg, 32% yield). MS m/z: 476.87, 478.86 [M+H]$^+$.

Example 91

5-((3,5-dichloropyridin-4-yl)thio)-N-((1-ethylpyrrolidin-3-yl)methyl)-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and (1-ethylpyrrolidin-3-yl)methanamine (12.8 mg, 0.1 mmol). The title compound was obtained as a solid (10.7 mg, 23% yield). MS ink: 460.87, 462.87 [M+H]$^+$.

Example 92

5-((3,5-dichloropyridin-4-yl)thio)-N-((3S,4S)-1-ethyl-4-methoxypyrrolidin-3-yl)-4-nitrothiophene-2-carboxamide: Prepared according to the procedure described for example 44 from 5-[(3,5-dichloro-4-pyridyl)sulfanyl]-4-nitrothiophene-2-carboxylic acid (35 mg, 0.1 mmol) and (3S,4S)-1-ethyl-4-methoxypyrrolidin-3-amine (14.4 mg, 0.1 mmol). The title compound was obtained as a solid (7.9 mg, 17% yield). MS m/z: 476.86, 478.86 [M+H]$^+$.

Example 93

5-((3,5-dichloropyridin-4-yl)thio)-N-(1-(2-methoxyethyl)-5-oxopyrrolidin-3-yl)-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 1-(2-methoxyethyl)pyrrolidin-3-amine (15.8 mg, 0.1 mmol). The title compound was obtained as a solid (3.4 mg, 7% yield). MS m/z: 490.84, 492.84 [M+H]$^+$.

Example 94

5-((3,5-dichloropyridin-4-yl)thio)-N-(1-methylpyrrolidin-3-yl)-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 1-methylpyrrolidin-3-amine (10.0 mg, 0.1 mmol). The title compound was obtained as a solid (4.3 mg, 10% yield). MS m/z: 432.84, 434.84 [M+H]$^+$.

Example 95

5-((3,5-dichloropyridin-4-yl)thio)-4-nitro-N-(2-oxopiperidin-3-yl)thiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 3-aminopiperidin-2-one (11.4 mg, 0.1 mmol). The title compound was obtained as a solid (10.4 mg, 23% yield). MS m/z: 446 [M+H]$^+$.

Example 96

5-((3,5-dichloropyridin-4-yl)thio)-4-nitro-N-phenethylthiophene-2-carboxamide: Prepared according to the procedure described for example 50 from 5-[(3,5-dichloro-4-pyridyl)sulfanyl]-4-nitro-thiophene-2-carboxylic acid (60 mg, 0.17 mmol) and phenethyl amine (78 mg, 0.68 mmol). The title compound was obtained as a yellow solid (70 mg, 91% yield). $^1$H NMR (400 MHz, d$_6$-DMSO) δ: 8.98 (3H, m), 8.39 (1H, s), 7.27 (2H, m), 7.19 (3H, m), 3.42 (2H, m), 2.80 (2H, m). MS m/z: 452.24, 454.26 [M+H]$^+$.

Example 97

5-((3,5-dichloropyridin-4-yl)thio)-N-(2,3-dimethoxybenzyl)-4-nitrothiophene-2-carboxamide: Prepared according to the procedure described for example 50 from 5-[(3,5-dichloro-4-pyridyl)sulfanyl]-4-nitro-thiophene-2-carboxylic acid (160 mg, 0.43 mmol) and 2,3-dimethoxy benzylamine (87 mg, 0.52 mmol). The title compound was obtained as a solid (80 mg, 37% yield). $^1$H NMR (400 MHz, d$_6$-DMSO) δ: 9.25 (1H, m), 8.98 (2H, m), 8.51 (1H, s), 6.99 (2H, m), 6.82 (1H, m), 4.38 (2H, m), 3.78 (3H, s), 3.71 (3H, s). MS m/z: 498.29, 500.27 [M+H]$^+$.

Example 98

5-((3,5-dichloropyridin-4-yl)thio)-N-(3,4-dimethoxybenzyl)-4-nitrothiophene-2-carboxamide: Prepared according to the procedure described for example 50 from 5-[(3,5-dichloro-4-pyridyl)sulfanyl]-4-nitro-thiophene-2-carboxylic acid (160 mg, 0.43 mmol) and 3,4-dimethoxy benzylamine (87 mg, 0.52 mmol). The title compound was obtained as a yellow solid (110 mg, 51% yield). $^1$H NMR (400 MHz, d$_6$-DMSO) δ: 9.30 (1H, m), 8.98 (2H, m), 8.47 (1H, s), 6.87 (3H, m), 4.32 (2H, m), 3.71 (6H, m). MS m/z: 498.26, 500.25 [M+H]$^+$.

Example 99

5-((3,5-dichloropyridin-4-yl)thio)-N-(3-methoxybenzyl)-4-nitrothiophene-2-carboxamide: Prepared according to the procedure described for example 70 from 5-[(3,5-dichloro-4-pyridyl)sulfanyl]-4-nitro-thiophene-2-carboxylic acid (200 mg, 0.57 mmol) and 3-methoxy benzylamine (104 mg, 0.68 mmol). The title compound was obtained as a yellow solid (35 mg, 14% yield). $^1$H NMR (400 MHz, d$_6$-DMSO) δ: 9.37 (1H, m), 8.98 (2H, m), 8.47 (1H, s), 7.23 (1H, m), 6.83 (3H, m) 4.37 (2H, m), 3.72 (3H, s). MS m/z: 468.26, 470.28 [M+H]$^+$.

Example 100

5-((3,5-dichloropyridin-4-yl)thio)-4-nitro-N-(3-(piperidin-1-yl)propyl)thiophene-2-carboxamide: Prepared according to the procedure described for example 50 from 5-[(3,5-dichloro-4-pyridyl)sulfanyl]-4-nitro-thiophene-2-carbonyl chloride (100 mg, 0.27 mmol) and 3-(piperidine-1-yl)propylamine (46 mg, 0.32 mmol). The title compound was obtained as a solid (50 mg, 39% yield). $^1$H NMR (400 MHz, d$_6$-DMSO) δ: 9.37 (1H, m), 9.03 (2H, s), 8.46 (1H, s), 7.32 (2H, dd), 7.20 (2H, dd), 4.43 (2H, m). MS m/z: 475.09, 477.08 [M+H]$^+$.

Example 101

5-((3,5-dichloropyridin-4-yl)thio)-4-nitro-N-(pyridin-3-ylmethyl)thiophene-2-carboxamide: Prepared according to the procedure described for example 50 from 5-[(3,5-dichloro-4-pyridyl)sulfanyl]-4-nitro-thiophene-2-carbonyl chloride (100 mg, 0.27 mmol) and 3-picolylamine (35 mg, 0.32 mmol). The title compound was obtained as a yellow solid (21 mg, 17% yield). $^1$H NMR (400 MHz, d$_6$-DMSO) δ: 9.42 (1H, m), 8.99 (2H, s), 8.51 (1H, s), 8.47 (1H, s), 7.69 (1H, m), 7.36 (1H, m), 4.43 (2H, m). MS m/z: 441.17, 443.16 [M+H]$^+$.

Example 102

5-((3,5-dichloropyridin-4-yl)thio)-N-(4-(methylsulfonyl)benzyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (100 mg, 0.27 mmol) and 4-methylsulfonyl-benzylamine hydrogen chloric acid salt (59 mg, 0.32 mmol). The title compound was obtained as a yellow solid (54 mg, 39% yield). $^1$H NMR (400 MHz, d$_6$-DMSO) δ: 9.51 (1H, m), 8.99 (2H, s), 8.48 (1H, s), 7.89 (2H, dd), 7.55 (2H, dd), 4.51 (2H, m), 3.18 (3H, s). MS m/z: 515.97, 517.99 [M+H]$^+$.

Example 103

5-((3,5-dichloropyridin-4-yl)thio)-N-((5-methylpyrazin-2-yl)methyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (150 mg, 0.41 mmol) and 2-(aminomethyl)-5-methyl-pyrazine (60 mg, 0.49 mmol). The title compound was obtained as a solid (40 mg, 23% yield). $^1$H NMR (400 MHz, d$_6$-DMSO) δ: 9.48 (1H, m), 8.98 (2H, s), 8.48 (1H, s), 8.47 (2H, m), 4.50 (2H, m), 2.50 (3H, s). MS m/z: 454.00, 456.04 [M+H]$^+$.

Example 104

5-((3,5-dichloropyridin-4-yl)thio)-4-nitro-N-(3-(2-oxopyrrolidin-1-yl)propyl)thiophene-2-carboxamide: Prepared according to the procedure described for example 50 from 5-[(3,5-dichloro-4-pyridyl)sulfanyl]-4-nitro-thiophene-2-carbonyl chloride (150 mg, 0.41 mmol) and 1-(3-amino-propyl)-2-pyrrolidinone (69 mg, 0.49 mmol). The title compound was obtained as a yellow solid (130 mg, 66% yield). $^1$H NMR (400 MHz, d$_6$-DMSO) δ: 8.98 (2H, s), 8.32(1H, m), 8.40 (1H, s), 3.33 (1H, m), 3.20 (4H, m), 2.21 (2H, m), 1.90 (2H, m), 1.66 (2H, m). MS m/z: 475.03, 477.05 [M+H]$^+$.

Example 105

N-(4-bromophenethyl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carbonyl chloride (100 mg, 0.27 mmol) and 4-bromophenethylamine (65 mg, 0.32 mmol). The title compound was obtained as a solid (30 mg, 21% yield). $^1$H NMR (400 MHz, d$_6$-DMSO) δ: 8.98 (2H, s), 8.88 (1H, m), 8.38 (1H, m), 7.47(2H, dd), 7.18 (2H, dd), 3.43 (2H, m), 2.78 (2H, m). MS m/z: 529.92, 531.95, 533.95 [M+H]$^+$.

Example 106

N-(4-chlorobenzyl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carbonyl chloride (100 mg, 0.27 mmol) and 4-chlorobenzylamine (45 mg, 0.32 mmol). The title compound was obtained as a yellow solid (18 mg, 14% yield). $^1$H NMR (400 MHz, d$_6$-DMSO) δ: 9.40 (1H, m), 8.99 (2H, s), 8.46 (1H, s), 7.43 (2H, dd), 7.31 (2H, dd), 4.39 (2H, m). MS m/z: 471.97, 473.95 [M+H]$^+$.

Example 107

5-((3,5-dichloropyridin-4-yl)thio)-N-(4-fluorobenzyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (100 mg, 0.27 mmol) and 4-fluorobenzylamine (40 mg, 0.32 mmol). The title compound was obtained as a solid (60 mg, 48% yield). $^1$H NMR (400 MHz, d$_6$-DMSO) δ: 9.37 (1H, m), 9.03 (2H, s), 8.46 (1H, s), 7.32 (2H, dd), 7.20 (2H, dd), 4.43 (2H, m). MS m/z: 456.04, 458.00 [M+H]$^+$.

Example 108

5-((3,5-dichloropyridin-4-yl)thio)-4-nitro-N-(2-(pyridin-3-yl)ethyl)thiophene-2-carboxamide: Prepared according to the procedure described for example 50 from 5-[(3,5-dichloro-4-pyridyl)sulfanyl]-4-nitro-thiophene-2-carbonyl chloride (100 mg, 0.27 mmol) and 3-(2-aminoethyl)pyridine (39 mg, 0.32 mmol). The title compound was obtained as a solid (75 mg, 49% yield). $^1$H NMR (400 MHz, d$_6$-DMSO) δ: 8.98 (2H, s), 8.91 (1H, m), 8.40 (2H, m), 8.38 (1H, s), 7.62 (1H, m), 7.30 (1H, m), 3.48 (2H, m), 2.81 (2H, m). MS m/z: 455.01, 457.00 [M+H]$^+$.

Example 109

5-((3,5-dichloropyridin-4-yl)thio)-4-nitro-N-(2-(pyridin-2-yl)ethyl)thiophene-2-carboxamide: Prepared according to the procedure described for example 50 from 5-[(3,5-dichloro-4-pyridyl)sulfanyl]-4-nitro-thiophene-2-carbonyl chloride (150 mg, 0.41 mmol) and 2-(2-aminoethyl)pyridine (65 mg, 0.49 mmol). The title compound was obtained as a solid (55 mg, 30% yield). $^1$H NMR (400 MHz, d$_6$-DMSO) δ: 8.98 (2H, s), 8.94 (1H, m), 8.49 (2H, m), 8.38 (1H, s), 7.69 (1H, m), 7.23 (1H, m), 3.56 (2H, m), 2.96 (2H, m). MS m/z: 453.02, 455.01 [M+H]$^+$.

Example 110

5-((3,5-dichloropyridin-4-yl)thio)-N-isopentyl-4-nitrothiophene-2-carboxamide: Prepared according to the procedure described for example 50 from 5-[(3,5-dichloro-4-pyridyl)sulfanyl]-4-nitro-thiophene-2-carbonyl chloride (150 mg, 0.41 mmol) and 3-methylbutylamine (43 mg, 0.49 mmol). The title compound was obtained as a solid (40 mg, 23% yield). $^1$H NMR (400 MHz, d$_6$-DMSO) δ: 8.98 (2H, s), 8.76 (1H, m), 8.42 (1H, s), 3.21 (2H, t), 1.58 (1H, m), 1.37 (2H, m), 0.93 (6H, m). MS m/z: 418.06, 420.08 [M+H]$^+$.

Example 111

5-((3,5-dichloropyridin-4-yl)thio)-N-(2-fluorophenethyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (150 mg, 0.41 mmol) and 2-fluoro-phenethylamine (67.9 mg, 0.49 mmol). The title compound was obtained as a solid (35 mg, 18% yield). $^1$H NMR (400 MHz, d$_6$-DMSO) δ: 8.98 (2H, m), 8.97 (1H, m), 8.37 (1H, s), 7.27 (2H, m), 7.16 (2H, m), 3.44 (2H, m), 2.82 (2H, m). MS m/z: 470.00, 472.01 [M+H]$^+$.

Example 112

5-((3,5-dichloropyridin-4-yl)thio)-N-(2,3-dihydro-1H-inden-4-yl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (150 mg, 0.41 mmol) and 5-aminoindane (65 mg, 0.49 mmol). The title compound was obtained as a yellow solid (65 mg, 34% yield). $^1$H NMR (400 MHz, d$_6$-DMSO) δ: 10.42 (1H, s), 9.00 (2H, s), 8.75 (1H, s), 7.52 (1H, m), 7.38 (1H, m), 7.19 (1H, m), 2.83 (4H, m), 2.00 (2H, m). MS m/z: 464.04, 466.06 [M+H]$^+$.

Example 113

5-((3,5-dichloropyridin-4-yl)thio)-N-(2-methoxyphenethyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (150 mg, 0.41 mmol) and 2-methoxy-phenthylamine (74 mg, 0.49 mmol). The title compound was obtained as a solid (60 mg, 30% yield). $^1$H NMR (400 MHz, d$_6$-DMSO) δ: 8.98 (2H, m), 8.90 (1H, m), 8.39 (1H, s), 7.21 (1H, m), 7.11 (1H, m), 6.94 (1H, m), 6.85 (1H, m), 3.75 (3H, s), 3.38 (2H, m), 2.76 (2H, m). MS m/z: 482.04, 484.03 [M+H]$^+$.

Example 114

5-((3,5-dichloropyridin-4-yl)thio)-4-nitro-N-(4-(trifluoromethoxy)benzyl)thiophene-2-carboxamide: Prepared according to the procedure described for example 50 from 5-[(3,5-dichloro-4-pyridyl)sulfanyl]-4-nitro-thiophene-2-carbonyl chloride (150 mg, 0.41 mmol) and 4-(trifluoromethoxy)-benzylamine (93 mg, 0.49 mmol). The title compound was obtained as a solid (50 mg, 30% yield). $^1$H NMR (400 MHz, $d_6$-DMSO) δ: 9.42 (1H, m), 8.98 (2H, s), 8.47 (1H, s), 7.42 (2H, dd), 7.33 (2H, dd), 4.43 (2H, m). MS m/z: 521.98, 523.99 [M+H]$^+$.

Example 115

5-((3,5-dichloropyridin-4-yl)thio)-4-nitro-N-(3-(pyridin-2-yl)propyl)thiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 3-(2-pyridyl)propan-1-amine (20.0 mg, 0.12 mmol). The title compound was obtained as a solid (14.5 mg, 26% yield). MS m/z: 469.01, 471.01 [M+H]$^+$.

Example 116

5-((3,5-dichloropyridin-4-yl)thio)-4-nitro-N-phenylthiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and aniline (11.0 mg, 0.12 mmol). The title compound was obtained as a yellow solid (5.0 mg, 11% yield). MS m/z: 425.96, 427.95 [M+H]$^+$.

Example 117

N-(2-(4-benzylpiperazin-1-yl)ethyl)-5-((3,5-dichloropyridin-4-yl)thio)-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 2-(4-benzylpiperazin-1-yl)ethanamine (25.0 mg, 0.12 mmol). The title compound was obtained as a solid (12.0 mg, 22% yield). MS m/z: 552.08, 554.08 [M+H]$^+$.

Example 118

N-(4-bromobenzyl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carbonyl chloride (150 mg, 0.41 mmol) and 4-bromo-benzylamine (91 mg, 0.49 mmol). The title compound was obtained as a yellow solid (19 mg, 35% yield). $^1$H NMR (400 MHz, $d_6$-DMSO) δ: 9.41 (1H, m), 8.99 (2H, s), 8.46 (1H, s), 7.53 (2H, dd), 7.24 (2H, dd), 4.43 (2H, m). MS m/z: 515.93, 517.96, 519.92 [M+H]$^+$.

Example 119

5-((3,5-dichloropyridin-4-yl)thio)-N-(3-methoxypropyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (150 mg, 0.41 mmol) and 3-methoxypropylamine (44 mg, 0.49 mmol). The title compound was obtained as a solid (80 mg, 46% yield). $^1$H NMR (400MHz, $d_6$-DMSO) δ: 8.99 (2H, s), 8.84 (1H, m), 8.42 (1H, s), 3.34 (1H, m), 3.33 (1H, m), 3.23 (5H, m), 1.69 (2H, m). MS m/z: 422.03, 424.03 [M+H]$^+$.

Example 120

5-((3,5-dichloropyridin-4-yl)thio)-N-(4-fluorophenethyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (150 mg, 0.41 mmol) and 4-fluorophenethylamine (68 mg, 0.49 mmol). The title compound was obtained as a solid (50 mg, 26% yield). $^1$H NMR (400 MHz, $d_6$-DMSO) δ: 8.99 (2H, s), 8.93 (1H, m), 8.39 (1H, s), 37.23 (2H, dd), 7.10 (2H, dd), 3.41 (2H, m), 2.77 (2H, m). MS m/z: 470.04, 472.03 [M+H]$^+$.

Example 121

5-((3,5-dichloropyridin-4-yl)thio)-N-(4-(dimethylamino)benzyl)-4-nitrothiophene-2-carboxamide: Prepared according to the procedure described for example 50 from 5-[(3,5-dichloro-4-pyridyl)sulfanyl]-4-nitro-thiophene-2-carboxylic acid (150 mg, 0.41 mmol) and 4-(dimethylamino)benzylamine hydrogen chloride salt (60.9 mg, 0.49 mmol). The title compound was obtained as a solid (70 mg, 37% yield). $^1$H NMR (400 MHz, $d_6$-DMSO) δ: 9.23 (1H, m), 8.99 (2H, s), 8.46 (1H, s), 7.1 (2H, dd), 6.7 (2H, dd), 4.26 (2H, m), 2.91 (6H, s). MS m/z: 483.05, 485.03 [M+H]$^+$.

Example 122

N-(3-acetamidobenzyl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carboxylic acid (150 mg, 0.41 mmol) and 4-(dimethylamino)benzylamine hydrogen chloride salt (66.5 mg, 0.49 mmol). The title compound was obtained as a solid (30 mg, 15% yield). $^1$H NMR (400 MHz, $d_6$-DMSO) δ: 9.91 (1H, m), 9.04 (1H, m), 8.99 (2H, s), 8.58 (1H, s), 7.51 (1H, m), 7.49 (1H, m), 7.22 (1H, m), 6.94 (1H, m), 4.36 (2H, m), 2.01 (3H, m). MS m/z: 497.05, 499.03 [M+H]$^+$.

Example 123

N-(3-cyclopropyl-1H-pyrazol-5-yl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carbonyl chloride (150 mg, 0.41 mmol) and 3-cyclopropyl-1H-pyrazole-5-amine (60 mg, 0.49 mmol). The title compound was obtained as a solid (80 mg, 35% yield). $^1$H NMR (400 MHz, $d_6$-DMSO) δ: 12.58 (1H, m), 11.26 (1H, s), 9.00 (2H, s), 8.81 (1H, m), 6.24 (1H, m), 1.84 (1H, m), 0.97 (2H, m), 0.69 (2H, m). MS m/z: 454.03, 456.04 [M+H]$^+$.

Example 124

N-cyclopropyl-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carbonyl chloride (100 mg, 0.27 mmol) and cyclopropylamine (19 mg, 0.32 mmol). The title compound was obtained as a solid (39 mg, 37% yield). $^1$H NMR (400 MHz, $d_6$-DMSO) δ: 8.98 (2H, m), 8.82 (1H, m), 8.37 (1H, s), 2.74 (1H, m), 0.69 (2H, m), 0.52 (2H, m). MS m/z: 388.02, 390.02 [M+H]$^+$.

Example 125

5-((3,5-dichloropyridin-4-yl)thio)-N-(3-(methylsulfonyl)benzyl)-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and (3-methylsulfonylphenyl)methanamine (22.0 mg, 0.12 mmol). The title compound was obtained as a solid (22.8 mg, 44% yield). MS m/z: 517.95, 519.95 [M+H]⁺.

Example 126

5-[(3,5-dichloro-4-pyridyl)sulfanyl]-N-[[3-(3-dimethylaminopropoxy)phenyl]methyl]-4-nitro-thiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 3-[3-(aminomethyl)phenoxy]-N,N-dimethyl-propan-1-amine (25.0 mg, 0.12 mmol). The title compound was obtained as a solid (35.4 mg, 65% yield). MS m/z: 541.06, 543.05 [M+H]⁺.

Example 127

5-((3,5-dichloropyridin-4-yl)thio)-N-methyl-N-(3-(methylthio)benzyl)-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and N-methyl-1-(3-methylsulfanylphenyl)methanamine (17.0 mg, 0.12 mmol). The title compound was obtained as a solid (33.5 mg, 67% yield). MS m/z: 500.01, 502.00 [M+H]⁺.

Example 128

5-((3,5-dichloropyridin-4-yl)thio)-N-(3-fluorobenzyl)-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 3-fluorobenzylamine (14.0 mg, 0.12 mmol). The title compound was obtained as a solid (22.5 mg, 49% yield). MS m/z: 457.96, 459.96 [M+H]⁺.

Example 129

5-((3,5-dichloropyridin-4-yl)thio)-N-(4-(methylsulfonyl)phenyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 4-methylsulfonylaniline (66 mg, 0.39 mmol). The title compound was obtained as a yellow solid (60 mg, 37% yield). $^1$H NMR (400 MHz, d$_6$-DMSO) δ: 10.88 (1H, m), 9.01 (2H, s), 8.87 (1H, s), 7.96 (4H, s), 3.20 (3H, s). MS m/z: 502.04, 503.99 [M+H]⁺.

Example 130

N-(5-chloro-2-methoxyphenyl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 2-methoxy-5-chloroaniline (61 mg, 0.39 mmol). The title compound was obtained as a yellow solid (110 mg, 69% yield). $^1$H NMR (400 MHz, d$_6$-DMSO) δ: 10.17 (1H, s), 9.00 (2H, s), 8.76 (1H, s), 7.57 (1H, m), 7.27 (1H, m), 7.13 (1H, m), 3.83 (3H, s). MS m/z: 488.02, 490.07 [M+H]⁺.

Example 131

5-((3,5-dichloropyridin-4-yl)thio)-N-(4-(1-hydroxyethyl)phenyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 4-(1-hydroxyethyl)aniline (53 mg, 0.39 mmol). The title compound was obtained as a solid (50 mg, 33% yield). $^1$H NMR (400 MHz, d$_6$-DMSO) δ: 10.50 (1H, s), 9.00 (2H, s), 8.72 (1H, m), 7.56 (2H, dd), 7.32 (2H, dd), 5.10 (1H, m), 4.68 (1H, m), 1.31 (3H, s). MS m/z: 468.10, 470.10 [M+H]⁺.

Example 132

5-((3,5-dichloropyridin-4-yl)thio)-N-(4-methoxy-2-methylphenyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 4-methoxy-2-methylaniline (53 mg, 0.39 mmol). The title compound was obtained as a solid (75 mg, 49% yield). $^1$H NMR (400 MHz, d$_6$-DMSO) δ: 10.12(1H, s), 9.00 (2H, s), 8.63 (1H, m), 7.12 (1H, dd), 6.83 (1H, m), 6.76 (1H, m), 3.73 (3H, s), 2.14 (3H, s). MS m/z: 468.15, 470.12 [M+H]⁺.

Example 133

N-(3-bromophenyl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 4-bromo-aniline (67 mg, 0.39 mmol). The title compound was obtained as a solid (55 mg, 33% yield). $^1$H NMR (400 MHz, d$_6$-DMSO) δ: 10.63 (1H, s), 9.01 (2H, s), 8.71 (1H, s), 7.94 (1H, m), 7.64 (1H, m), 7.34 (2H, m). MS m/z: 501.96, 503.97, 505.94 [M+H]⁺.

Example 134

N-(2-chlorophenyl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 2-chloro-aniline (49 mg, 0.39 mmol). The title compound was obtained as a solid (42 mg, 28% yield). $^1$H NMR (400 MHz, d$_6$-DMSO) δ: 10.53 (1H, s), 8.99 (2H, s), 8.61 (1H, s), 7.55 (1H, m), 7.47 (1H, m), 7.38 (2H, m), 7.32 (1H, m). MS m/z: 458.07, 460.05 [M+H]⁺.

Example 135

N-(2,6-dichlorophenyl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 2,6-dichloro-aniline (63 mg, 0.39 mmol). The title compound was obtained as a solid (70 mg, 43% yield). $^1$H NMR (400 MHz, d$_6$-DMSO) δ: 10.76 (1H, s), 8.99 (2H, s), 8.68 (1H, s), 7.60 (2H, m), 7.41 (1H, m). MS m/z: 492.00, 493.99, 495.96 [M+H]⁺.

Example 136

5-((3,5-dichloropyridin-4-yl)thio)-N-(4-fluorophenyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 4-fluoro-aniline (43 mg, 0.39 mmol). The title compound was obtained as a solid (60 mg, 41% yield). $^1$H NMR (400 MHz, d$_6$-DMSO) δ: 10.58 (1H, s), 9.00 (2H, s), 8.69 (1H, s), 7.67 (2H, m), 7.21 (2H, m). MS m/z: 442.06, 444.06 [M+H]⁺.

Example 137

N-(3-chloro-4-fluorophenyl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 3-dichloro-4-fluoroaniline (56 mg, 0.39 mmol). The title compound was obtained as a solid (45 mg, 29% yield). $^1$H NMR (400 MHz, $d_6$-DMSO) δ: 10.68 (1H, s), 9.01 (2H, s), 8.67 (1H, s), 7.92 (1H, m), 7.60 (1H, m), 7.44(1H, m). MS m/z: 475.99, 478.02, 479.97 [M+H]$^+$.

Example 138

5-((3,5-dichloropyridin-4-yl)thio)-N-(3-fluorophenyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 3-fluoro-aniline (43 mg, 0.39 mmol). The title compound was obtained as a solid (75 mg, 52% yield). $^1$H NMR (400 MHz, $d_6$-DMSO) δ: 10.68 (1H, s), 9.01 (2H, s), 8.71 (1H, s), 7.61 (1H, m), 7.42 (1H, m), 6.97 (1H, m). MS m/z: 442.07, 444.05 [M+H]$^+$.

Example 139

5-((3,5-dichloropyridin-4-yl)thio)-N-(4-fluoro-2-(trifluoromethyl)phenyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 4-fluoro-2-trifluoromethyl-aniline (69 mg, 0.39 mmol). The title compound was obtained as a solid (60 mg, 36% yield). $^1$H NMR (400 MHz, $d_6$-DMSO) δ: 10.55 (1H, s), 8.99 (2H, m), 8.64 (1H, s), 7.73 (1H, m), 7.64 (1H, m), 7.58 (1H, m). MS m/z: 510.02, 512.00 [M+H]$^+$.

Example 140

5-((3,5-dichloropyridin-4-yl)thio)-N-(4-fluoro-3-(trifluoromethyl)phenyl)-4-nitrothiophene-2-carboxamid: Prepared according to the procedure described for example 50 from 5-[(3,5-dichloro-4-pyridyl)sulfanyl]-4-nitro-thiophene-2-carbonyl chloride (120 mg, 0.33 mmol) and 4-fluoro-3-trifluoromethyl-aniline (69 mg, 0.39 mmol). The title compound was obtained as a solid (95 mg, 57% yield). $^1$H NMR (400 MHz, $d_6$-DMSO) δ: 10.82 (1H, s), 9.01 (2H, s), 8.68 (1H, s), 8.09 (1H, m), 7.97 (1H, m), 7.54 (1H, m). MS m/z: 510.03, 512.02 [M+H]$^+$.

Example 141

N-(2,4-dichlorophenyl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 2,4-dichloroaniline (62 mg, 0.39 mmol). The title compound was obtained as a solid (85 mg, 52% yield). $^1$H NMR (400 MHz, $d_6$-DMSO) δ: 10.58 (1H, s), 8.99 (2H, m), 8.69 (1H, s), 7.74 (1H, m), 7.48 (2H, m). MS m/z: 491.96, 493.96, 495.97 [M+H]$^+$.

Example 142

N-(3-chlorophenyl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 3-chloroaniline (49 mg, 0.39 mmol). The title compound was obtained as a solid (70 mg, 47% yield). $^1$H NMR (400 MHz, $d_6$-DMSO) δ: 10.79 (1H, s), 9.01 (2H, s), 8.75 (1H, s), 7.86 (1H, s), 7.67 (1H, m), 7.39 (1H, m), 7.20 (1H, m). MS m/z: 458.11, 460.09, 462.03 [M+H]$^+$.

Example 143

5-((3,5-dichloropyridin-4-yl)thio)-N-(2,4-difluorophenyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 2,4-difluoroaniline (50 mg, 0.39 mmol). The title compound was obtained as a solid (70 mg, 47% yield). $^1$H NMR (400 MHz, $d_6$-DMSO) δ: 10.53 (1H, s), 8.99 (2H, s), 8.68 (1H, m), 7.54 (1H, m), 7.40 (1H, m), 7.12 (1H, m). MS m/z: 460.05, 462.03 [M+H]$^+$.

Example 144

5-((3,5-dichloropyridin-4-yl)thio)-N-(3-fluoro-2-methylphenyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 2,4-difluoroaniline (48 mg, 0.39 mmol). The title compound was obtained as a solid (65 mg, 44% yield). $^1$H NMR (400 MHz, $d_6$-DMSO) δ: 10.41 (1H, s), 9.00 (2H, s), 8.67 (1H, s), 7.25 (1H, m), 7.10 (2H, m). MS m/z: 456.08, 458.07 [M+H]$^+$.

Example 145

5-((3,5-dichloropyridin-4-yl)thio)-N-(3-(difluoromethoxy)benzyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 3-difluoromethoxy-benzylamine (46.6 mg, 0.39 mmol). The title compound was obtained as a solid (100 mg, 42% yield). $^1$H NMR (400 MHz, $d_6$-DMSO) δ: 9.43 (1H, m), 8.98 (2H, s), 8.47 (1H, s), 7.39 (1H, m), 7.11 (1H, m), 7.06 (2H, m), 4.42 (2H, m), 3.32 (1H, m). MS m/z: 504.06, 506.07 [M+H]$^+$.

Example 146

5-((3,5-dichloropyridin-4-yl)thio)-N-(3-(dimethylamino)benzyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 3-dimethylamino-benzylamine (58.3 mg, 0.39 mmol). The title compound was obtained as a solid (98.2 mg, 51% yield). $^1$H NMR (400 MHz; $d_6$-DMSO) δ: 9.31 (1H, m), 8.98 (2H, s), 8.49 (1H, s), 7.11 (1H, m), 6.63 (2H, m), 6.55 (1H, m), 4.33 (2H, m), 2.86 (6H, s). MS m/z: 483.10, 485.11 [M+H]$^+$.

Example 147

5-((3,5-dichloropyridin-4-yl)thio)-N-((2,3-dihydrobenzo[b][1,4]dioxin-6-yl)methyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 2,3-dihydrobenzo[b][1,4]dioxin-6-ylamine (58 mg, 0.39 mmol). The title compound was obtained as a solid (98 mg, 60% yield). ¹H NMR (400 MHz, d₆-DMSO) δ: 9.31 (1H, m), 8.98 (2H, s), 6.77 (2H, m), 6.71 (1H, m), 4.26 (2H, m), 4.20 (4H, s). MS m/z: 495.15, 498.13 [M+H]⁺.

Example 148

5-((3,5-dichloropyridin-4-yl)thio)-4-nitro-N-(3-(trifluoromethyl)benzyl)thiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 3-(trifluoromethyl)benzylamine (47 mg, 0.39 mmol). The title compound was obtained as a solid (87 mg, 52% yield). ¹H NMR (400 MHz, d₆-DMSO) δ: 9.48 (1H, m), 8.99 (2H, s), 8.47 (1H, s), 7.64 (2H, m), 7.57 (1H, m), 4.56 (2H, m). MS m/z: 506.07, 508.07 [M+H]⁺.

Example 149

5-((3,5-dichloropyridin-4-yl)thio)-N-(3-ethoxybenzyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 3-ethoxybenzylamine (58.3 mg, 0.39 mmol). The title compound was obtained as a solid (71 mg, 45% yield). ¹H NMR (400 MHz, d₆-DMSO) δ: 9.36 (1H, m), 8.99 (2H, s), 8.48 (1H, s), 7.22 (1H, m), 6.81 (3H, m), 4.36 (2H, m), 3.99 (2H, q), 1.30 (3H, t). MS m/z: 482.13, 484.10 [M+H]⁺.

Example 150

5-((3,5-dichloropyridin-4-yl)thio)-N-(3-methylbenzyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 3-methylbenzylamine (47.0 mg, 0.39 mmol). The title compound was obtained as a solid (35 mg, 24% yield). ¹H NMR (400 MHz, d₆-DMSO) δ: 9.36 (1H, m), 8.99 (2H, s), 8.48 (1H, s), 7.20 (1H, m), 7.09 (3H, m), 4.35 (2H, m), 2.27 (3H, s). MS m/z: 452.12, 454.14 [M+H]⁺.

Example 151

N-(benzo[d][1,3]dioxol-5-ylmethyl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and benzo[d][1,3]dioxol-5-ylmethylamine (58.0 mg, 0.39 mmol). The title compound was obtained as a solid (98 mg, 60% yield). ¹H NMR (400 MHz, d₆-DMSO) δ: 9.31 (1H, m), 8.99 (2H, s), 8.46 (1H, s), 6.84 (2H, m), 6.76 (1H, m), 5.97 (2H, s), 4.30 (2H, m). MS m/z: 482.11, 484.08 [M+H]⁺.

Example 152

N-(4-bromophenyl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 4-bromoaniline (67 mg, 0.39 mmol). The title compound was obtained as a solid (55 mg, 33% yield). ¹H NMR (400 MHz, d₆-DMSO) δ: 10.63 (1H, s), 9.01 (2H, s), 8.71 (1H, s), 7.63 (2H, m), 7.56 (2H, m). MS m/z: 502.01, 503.94, 505.92 [M+H]⁺.

Example 153

N-(tert-butyl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and t-butylamine (36 mg, 0.39 mmol). The title compound was obtained as a solid (25 mg, 15% yield). ¹H NMR (400 MHz, d₆-DMSO) δ: 8.98 (2H, s), 8.57 (1H, s), 8.23 (1H, s), 1.31 (9H, s). MS m/z: 404.09, 406.07 [M+H]⁺.

Example 154

N-cyclohexyl-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and cyclohexylamine (49 mg, 0.39 mmol). The title compound was obtained as a solid (60 mg, 34% yield). ¹H NMR (400 MHz, d₆-DMSO) δ: 8.98 (2H, s), 8.62 (1H, m), 8.50 (1H, s), 3.63 (1H, m), 1.71 (4H, m), 1.59 (1H, m), 1.24 (4H, m), 1.09 (1H, m). MS m/z: 430.13, 432.07 [M+H]⁺.

Example 155

5-((3,5-dichloropyridin-4-yl)thio)-N-(4-methoxyphenyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and p-anisidine (60 mg, 0.39 mmol). The title compound was obtained as a solid (42 mg, 23% yield). ¹H NMR (400 MHz, d₆-DMSO) δ: 10.43 (1H, s), 9.00 (2H, s), 8.67 (1H, s), 7.56 (2H, m), 6.94 (2H, m), 3.73 (3H, s). MS m/z: 454.08, 456.02 [M+H]⁺.

Example 156

5-((3,5-dichloropyridin-4-yl)thio)-N-(3-methoxyphenyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and m-anisidine (60 mg, 0.39 mmol). The title compound was obtained as a solid (27 mg, 15% yield). ¹H NMR (400 MHz, d₆-DMSO) δ: 10.49 (1H, s), 9.01 (2H, s), 8.73 (1H, m), 7.31 (1H, m), 7.26 (2H, m), 6.70 (1H, m), 3.80 (3H, s). MS m/z: 454.09, 456.04 [M+H]⁺.

Example 157

5-((3,5-dichloropyridin-4-yl)thio)-N-(4-morpholinophenyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 4-morpholinoaniline (69 mg, 0.39 mmol). The title compound was obtained as a solid (70 mg, 44% yield). ¹H NMR (400 MHz, d₆-DMSO) δ: 10.41 (1H, m), 9.00 (2H, s), 8.67 (1H, s), 7.51 (2H, m), 6.94 (2H, m), 3.72 (4H, m), 3.06 (4H, m). MS m/z: 509.15, 511.13 [M+H]⁺.

Example 158

N-(benzo[d][1,3]dioxol-5-yl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and benzo[d][1,3]dioxol-5-ylamine (53 mg, 0.39 mmol). The title compound was obtained as a solid (28 mg, 44% yield). $^1$H NMR (400 MHz, d$_6$-DMSO) δ: 10.43 (1H, m), 9.00 (2H, s), 8.67 (1H, s), 7.29 (1H, m), 7.06 (1H, m), 6.91 (1H, m), 6.04 (2H, s). MS m/z: 468.04, 470.04 [M+H]$^+$.

Example 159

5-((3,5-dichloropyridin-4-yl)thio)-N-(2,5-difluorophenyl)-4-nitrothiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and 2,5-difluoroaniline (50 mg, 0.39 mmol). The title compound was obtained as a solid (45 mg, 44% yield). $^1$H NMR (400 MHz, d$_6$-DMSO) δ: 10.62 (1H, m), 9.00 (2H, s), 8.75 (1H, s), 7.50 (1H, m), 7.48 (1H, m), 7.40 (1H, m). MS m/z: 460.05, 462.04 [M+H]$^+$.

Example 160

5-((3,5-dichloropyridin-4-yl)thio)-4-nitro-N-(4-sulfamoylphenyl)thiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and sulfanilide (84 mg, 0.39 mmol). The title compound was obtained as a solid (90 mg, 44% yield). $^1$H NMR (400 MHz, d$_6$-DMSO) δ: 10.79 (1H, m), 9.01 (2H, s), 8.76 (1H, s), 7.81 (4H, s), 7.23 (2H, s), 7.40 (1H, m). MS m/z: 503.02, 505.04 [M+H]$^+$.

Example 161

5-((3,5-dichloropyridin-4-yl)thio)-4-nitro-N-(2-(piperidin-1-yl)ethyl)thiophene-2-carboxamide: Prepared according to the procedure described for example 50 from 5-[(3,5-dichloro-4-pyridyl)sulfanyl]-4-nitro-thiophene-2-carbonyl chloride (120 mg, 0.33 mmol) and N-(2-aminoethyl)piperidine (63 mg, 0.39 mmol). The title compound was obtained as a solid (20 mg, 11% yield). $^1$H NMR (400 MHz, d$_6$-DMSO) δ: 8.99 (2H, s), 8.83 (1H, m), 8.42 (1H, s), 3.32 (2H, m), 2.42 (3H, m), 2.35 (1H, m), 1.48 (4H, m), 1.37 (2H, m). MS m/z: 459.16, 461.15 [M+H]$^+$.

Example 162

N-((6-chloropyridin-3-yl)methyl)-5-((3,5-dichloropyridin-4-yl)thio)-4-nitrothiophene-2-carboxamide: Prepared according to the procedure described for example 50 from 5-[(3,5-dichloro-4-pyridyl)sulfanyl]-4-nitro-thiophene-2-carboxylic acid (1.0 g, 2.85 mmol) and (6-chloropyridin-3-yl)methylamine (488 mg, 3.42 mmol). The title compound was obtained as a solid (500 mg, 37% yield). $^1$H NMR (400 MHz, d$_6$-DMSO) δ: 9.43 (1H, m), 9.00 (2H, s), 8.44 (1H, s), 8.34 (1H, s), 7.77 (1H, dd), 7.49 (1H, dd), 4.23 (2H, m). MS m/z: 473.05, 475.03 [M+H]$^+$.

Example 163 methyl 4-((5-((3,5-dichloropyridin-4-yl)thio)-4-nitrothiophene-2-carboxamido)methyl)benzoate: Prepared according to the procedure described for example 50 from 5-[(3,5-dichloro-4-pyridyl)sulfanyl]-4-nitro-thiophene-2-carbonyl chloride (120 mg, 0.33 mmol) and methyl 4-(aminomethyl)benzoate hydrogen chloride (81 mg, 0.39 mmol). The title compound was obtained as a solid (70 mg, 35% yield). $^1$H NMR (400 MHz, d$_6$-DMSO) δ: 9.46 (1H, m), 8.98 (2H, s), 8.48 (1H, s), 7.91 (2H, m), 7.43 (2H, m), 4.49 (2H, m), 3.84 (3H, s). MS m/z: 496.31, 498.15 [M+H]$^+$.

Example 164

5-((3,5-dichloropyridin-4-yl)thio)-4-nitro-N-(3-(trifluoromethyl)-1H-pyrazol-5-yl)thiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 3-(trifluoromethyl)-1H-pyrazol-5-amine (18.0 mg, 0.12 mmol). The title compound was obtained as a solid (13.0 mg, 27% yield). MS m/z: 483.93, 485.93 [M+H]$^+$.

Example 165

5-((3,5-dichloropyridin-4-yl)thio)-N-(4-hydroxybenzyl)-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 4-hydroxylbenzylamine (14.5 mg, 0.12 mmol). The title compound was obtained as a solid (23.1 mg, 51% yield). MS m/z: 455.96, 457.96 [M+H]$^+$.

Example 166

5-[(3,5-dichloro-4-pyridyl)sulfanyl]-N-(1-ethyltriazol-4-yl)-4-nitro-thiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 1-ethyltriazol-4-amine (11.0 mg, 0.12 mmol). The title compound was obtained as a solid (7.1 mg, 16% yield). MS m/z: 458.00, 460.00 [M+H]$^+$.

Example 167

5-((3,5-dichloropyridin-4-yl)thio)-N-(1-methyl-1H-pyrazol-5-yl)-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 2-methylpyrazol-3-amine (9.7 mg, 0.12 mmol). The title compound was obtained as a solid (10.0 mg, 23% yield). MS m/z: 429.96, 431.96 [M+H]$^+$.

Example 168

5-((3,5-dichloropyridin-4-yl)thio)-N-(1-methylpiperidin-4-yl)-4-nitrothiophene-2-carboxamide: Prepared according to the procedure described for example 70 from 5-[(3,5-dichloro-4-pyridyl)sulfanyl]-4-nitro-thiophene-2-carboxylic acid (150 mg, 0.43 mmol) and 1-methylpiperidin-4-amine (58 mg, 0.51 mmol). The title compound was obtained as a solid (95.0 mg, 50% yield). $^1$H NMR (400 MHz, d$_6$-DMSO) δ: 8.98 (1H, m), 8.65 (1H, m), 8.49 (1H, m), 3.60 91H, m), 2.78 (2H, m), 2.18 (3H, s), 1.98 (2H, m), 1.75 (2H, m), 1.53 (2H, m). MS m/z: 447.31, 449.29 [M+H]$^+$.

Example 169

5-((3,5-dichloropyridin-4-yl)thio)-4-nitro-N-(3,4,5-trimethoxyphenyl)thiophene-2-carboxamide: Prepared according to the procedure described for example 70 from 5-[(3,5-dichloro-4-pyridyl)sulfanyl]-4-nitro-thiophene-2-carboxylic acid (150 mg, 0.43 mmol) and 3,4,5-trimethoxyaniline (93.7 mg, 0.51 mmol). The title compound was obtained as a yellow solid (71.0 mg, 32% yield). $^1$H NMR (400 MHz, d$_6$-DMSO)

δ: 10.45 (1H, m), 9.01 (2H, m), 8.68 (1H, m), 7.06 (2H, m), 3.32 (9H, s). MS m/z: 514.19, 516.12 [M+H]$^+$.

Example 170

5-((3,5-dichloropyridin-4-yl)thio)-4-nitro-N-(3,4-dimethoxyphenyl)thiophene-2-carboxamide: Prepared according to the procedure described for example 70 from 5-[(3,5-dichloro-4-pyridyl)sulfanyl]-4-nitro-thiophene-2-carboxylic acid (150 mg, 0.43 mmol) and 3,4-dimethoxyaniline (78.3 mg, 0.51 mmol). The title compound was obtained as a yellow solid (25.0 mg, 12% yield). $^1$H NMR (400 MHz, d$_6$-DMSO) δ: 10.54 (1H, m), 9.00 (2H, m), 8.67 (1H, m), 7.30 (1H, m), 7.22 (1H, m), 6.94 (1H, m), 3.72 (6H, s). MS m/z: 484.24, 486.25 [M+H]$^+$.

Example 171

5-((3,5-dichloropyridin-4-yl)thio)-N-(isoxazol-3-yl)-4-nitrothiophene-2-carboxamide: Prepared according to the procedure described for example 70 from 5-[(3,5-dichloro-4-pyridyl)sulfanyl]-4-nitro-thiophene-2-carboxylic acid (150 mg, 0.43 mmol) and isoxazol-3-amine (43 mg, 0.51 mmol). The title compound was obtained as a brown solid (20.0 mg, 11% yield). $^1$H NMR (400 MHz, d$_6$-DMSO) δ: 11.90 (1H, s), 9.03 (2H, s), 8.86 (1H, m), 6.89 (1H, s). MS m/z: 415.18, 417.16 [M+H]$^+$.

Example 172

5-((3,5-dichloropyridin-4-yl)thio)-4-nitro-N-(thiazol-2-yl)thiophene-2-carboxamide: Prepared according to the procedure described for example 70 from 5-[(3,5-dichloro-4-pyridyl)sulfanyl]-4-nitro-thiophene-2-carboxylic acid (150 mg, 0.43 mmol) and aminothiazole (51.2 mg, 0.51 mmol). The title compound was obtained as a brown solid (77.0 mg, 42% yield). $^1$H NMR (400 MHz, d$_6$-DMSO) δ: 13.12 (1H, br), 9.02 (2H, s), 7.73 (1H, m), 7.24 (1H, m). MS m/z: 431.20, 433.13 [M+H]$^+$.

Example 173

5-((3,5-dichloropyridin-4-yl)thio)-4-nitro-N-(quinolin-3-yl)thiophene-2-carboxamide: Prepared according to the procedure described for example 70 from 5-[(3,5-dichloro-4-pyridyl)sulfanyl]-4-nitro-thiophene-2-carboxylic acid (150 mg, 0.43 mmol) and 3-aminoquinoline (73.7 mg, 0.51 mmol). The title compound was obtained as a yellow solid (40 mg, 20% yield). $^1$H NMR (400 MHz, d$_6$-DMSO) δ: 10.97 (1H, br), 9.066 (1H, m), 9.02 (2H, m), 8.77 (1H, m), 8.65 (1H, m), 7.95 (2H, m), 7.69 (1H, m), 7.59 (1H, m). MS m/z: 475.23, 477.28 [M+H]$^+$.

Example 174

5-((3,5-dichloropyridin-4-yl)thio)-N-(4-(methylthio)phenyl)-4-nitrothiophene-2-carboxamide: Prepared according to the procedure described for example 70 from 5-[(3,5-dichloro-4-pyridyl)sulfanyl]-4-nitro-thiophene-2-carboxylic acid (150 mg, 0.43 mmol) and 4-(methylthio)aniline (72.0 mg, 0.51 mmol). The title compound was obtained as a solid (28.0 mg, 15% yield). $^1$H NMR (400 MHz, d$_6$-DMSO) δ: 10.53 br), 9.00 (2H, s), 8.74 (1H, m), 7.62 (2H, m), 7.28 (2H, m). MS m/z: 470.13, 472.11 [M+H]$^+$.

Example 175

5-((3,5-dichloropyridin-4-yl)thio)-N-(6-methoxypyridin-3-yl)-4-nitrothiophene-2-carboxamide: Prepared according to the procedure described for example 70 from 5-[(3,5-dichloro-4-pyridyl)sulfanyl]-4-nitro-thiophene-2-carboxylic acid (150 mg, 0.43 mmol) and 5-aminoisoquinoline (64.0 mg, 0.51 mmol). The title compound was obtained as a solid (14.0 mg, 10% yield). $^1$H NMR (400 MHz, d$_6$-DMSO) δ: 10.59 (1H, m), 9.03 (2H, s), 8.65 (1H, m), 8.49 (1H, m), 7.92 (1H, m), 6.86 (1H, m), 3.85 (3H, s). MS m/z: 457.21, 459.24 [M+H]$^+$.

Example 176

5-((3,5-dichloropyridin-4-yl)thio)-N-((1r,3s,5R,7S)-3-hydroxyadamantan-1-yl)-4-nitrothiophene-2-carboxamide: Prepared according to the procedure described for example 70 from 5-[(3,5-dichloro-4-pyridyl)sulfanyl]-4-nitro-thiophene-2-carboxylic acid (150 mg, 0.43 mmol) and (1s,3r,5R,7S)-3-aminoadamantan-1-ol (86.0 mg, 0.51 mmol). The title compound was obtained as a solid (85.0 mg, 40% yield). $^1$H NMR (400 MHz, d$_6$-DMSO) δ: 8.98 (2H, s), 8.59 (1H, s), 8.17 (1H, m), 4.53 (1H, m), 2.16 (2H, m), 1.85 (6H, m), 1.52 (4H, m), 1.44 (2H, m). MS m/z: 498.20, 500.23 [M+H]$^+$.

Example 177

N-(bicyclo[2.2.1]heptan-2-yl)-5-((3,5-dichloropyridin-4-yl)thio)-4-nitrothiophene-2-carboxamide: Prepared according to the procedure described for example 70 from 5-[(3,5-dichloro-4-pyridyl)sulfanyl]-4-nitro-thiophene-2-carboxylic acid (150 mg, 0.43 mmol) and endo-2-amino-norbornane (57.0 mg, 0.51 mmol). The title compound was obtained as a solid (60.0 mg, 32% yield). $^1$H NMR (400 MHz, d$_6$-DMSO) δ: 8.98 (2H, m), 8.61 (1H, s), 8.59 (1H, m), 3.99 (1H, m), 2.31 (1H, m), 2.16 (1H, m), 1.87 (1H, m), 1.50 (1H, m), 1.47 (1H, M), 1.40 (1H, M), 1.31 (2H, M), 1.27 (2H, M), 1.01 (1H, M). MS m/z: 442.20, 444.21 [M+H]$^+$.

Example 178

5-((3,5-dichloropyridin-4-yl)thio)-4-nitro-N-(2,2,6,6-tetramethylpiperidin-4-yl)thiophene-2-carboxamide: Prepared according to the procedure described for example 70 from 5-[(3,5-dichloro-4-pyridyl)sulfanyl]-4-nitro-thiophene-2-carboxylic acid (150 mg, 0.43 mmol) and 2,2,6,6-tetramethylpiperidin-4-amine (81.0 mg, 0.51 mmol). The title compound was obtained as a solid (35.0 mg, 17% yield). $^1$H NMR (400 MHz, d$_6$-DMSO) δ: 8.99 (2H, m), 8.81 (1H, m), 8.47 (1H, s), 7.81 (1H, m), 4.18 (1H, m), 1.96 (2H, m), 1.51 (2H, m), 1.39 (12H, m). MS m/z: 487.25, 489.27 [M+H]$^+$.

Example 179

5-((3,5-dichloropyridin-4-yl)thio)-N-(isoquinolin-5-yl)-4-nitrothiophene-2-carboxamide: Prepared according to the procedure described for example 70 from 5-[(3,5-dichloro-4-pyridyl)sulfanyl]-4-nitro-thiophene-2-carboxylic acid (150 mg, 0.43 mmol) and 5-aminoisoquinoline (73.7 mg, 0.51 mmol). The title compound was obtained as a yellow solid (23.0 mg, 12% yield). $^1$H NMR (400 MHz, d$_6$-DMSO) δ: 10.85 (1H, br), 9.36 (1H, s), 9.00 (2H, s), 8.83 (1H, m), 8.54 (1H, m), 8.08 (1H, m), 7.84 (2H, m), 7.71 (1H, m). MS m/z: 475.17, 477.12 [M+H]$^+$.

Example 180

5-((3,5-dichloropyridin-4-yl)thio)-4-nitro-N-(quinolin-6-yl)thiophene-2-carboxamide: Prepared according to the procedure described for example 70 from 5-[(3,5-dichloro-4- pyridyl)sulfanyl]-4-nitro-thiophene-2-carboxylic acid (150 mg, 0.43 mmol) and 6-aminoquinoline (73.7 mg, 0.51 mmol). The title compound was obtained as a yellow solid (52 mg, 25% yield). $^1$H NMR (400 MHz, d$_6$-DMSO) δ: 10.84 (1H, br), 9.02 (2H, m), 8.825 (1H, m), 8.81 (1H, m), 8.34 (1H, m), 8.32 (1H, m), 8.04 (1H, m), 7.97 (1H, m), 7.51 (1H, m). MS m/z: 475.18, 477.09 [M+H]$^+$.

Example 181

5-((3,5-dichloropyridin-4-yl)thio)-N-(4-hydroxyphenyl)-4-nitrothiophene-2-carboxamide: Prepared according to the procedure described for example 70 from 5-[(3,5-dichloro-4-pyridyl)sulfanyl]-4-nitro-thiophene-2-carboxylic acid (150 mg, 0.43 mmol) and 4-aminophenol (56.0 mg, 0.51 mmol). The title compound was obtained as a solid (10 mg, 5% yield). $^1$H NMR (400 MHz, d$_6$-DMSO) δ: 10.34 (1H, s), 9.36 (1H, m), 9.00 (2H, s), 8.66 (1H, m), 7.42 (2H, m), 6.74 (2H, m). MS m/z: 440.14, 442.17 [M+H]$^+$.

Example 182

5-((3,5-dichloropyridin-4-yl)thio)-N-(1-(2-(dimethylamino)ethyl)-3-methyl-1H-pyrazol-5-yl)-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 1-(2-(dimethylamino)ethyl)-3-methyl-1H-pyrazol-5-amine (17.0 mg, 0.10 mmol). The title compound was obtained as a solid (20.8 mg, 23% yield). MS m/z: 501.02, 503.02 [M+H]$^+$.

Example 183

N-(4-acetylphenyl)-5-((3,5-dichloropyridin-4-yl)thio)-4-nitrothiophene-2-carboxamide: Prepared according to the procedure described for example 50 from 5-((3,5-dichloropyridin-4-yl)thio)-4-nitrothiophene-2-carbonyl chloride (0.25 mg, 0.59 mmol) and 1-(4-aminophenyl)ethanone (88 mg, 0.65 mmol). The title compound was obtained as a solid (27.0 mg, 10% yield). $^1$H NMR (400 MHz, d$_6$-DMSO) δ: 10.78 (1H, s), 9.01 (2H, s), 8.75 (1H, m), 8.01 (2H, m), 7.82 (2H, m), 2.51 (3H, s). MS m/z: 466.03, 468.03 [M+H]$^+$.

Example 184

5-((3,5-dichloropyridin-4-yl)thio)-N-(8-methyl-8-azabicyclo[3.2.1]octan-3-yl)-4-nitrothiophene-2-carboxamide: Prepared according to the procedure described for example 70 from 5-[(3,5-dichloro-4-pyridyl)sulfanyl]-4-nitro-thiophene-2-carboxylic acid (150 mg, 0.43 mmol) and 8-methyl-8-azabicyclo[3.2.1]octan-3-amine (71.0 mg, 0.52 mmol). The title compound was obtained as a solid (40 mg, 20% yield). $^1$H NMR (400 MHz, d$_6$-DMSO) δ: 8.97 (2H, m), 8.52 (1H, s), 8.44 (1H, s), 3.85 (1H, m), 3.79 (2H, m), 2.64 (3H, m), 2.25 (2H, m), 2.22 (4H, m), 2.16 (2H, m). MS m/z: 475.35, 477.33 [M+H]$^+$.

Example 185

5-((3,5-dichloropyridin-4-yl)thio)-N-(2-(1-ethylpiperidin-4-yl)ethyl)-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 2-(1-ethylpiperidin-4-yl)ethanamine (15.6 mg, 0.12 mmol). The title compound was obtained as a solid (26.1 mg, 53% yield). MS m/z: 489.06, 491.06 [M+H]$^+$.

Example 186

5-((3,5-dichloropyridin-4-yl)thio)-N-(1-ethyl-1H-1,2,4-triazol-3-yl)-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 1-ethyl-1H-1,2,4-triazol-3-amine (11.2 mg, 0.12 mmol). The title compound was obtained as a solid (8.9 mg, 20% yield). MS m/z: 466.95, 468.95 [M+H]$^+$.

Example 187

5-((3,5-dichloropyridin-4-yl)thio)-N-(1-isopropylpiperidin-4-yl)-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 1-isopropylpiperidin-4-amine (21.5 mg, 0.12 mmol). The title compound was obtained as a solid (10.7 mg, 23% yield). $^1$H NMR (400 MHz, d$_6$-DMSO) δ: 8.98 (2H, m), 8.63 (1H, d), 8.50 (1H, s), 3.56 (1H, m), 2.77 (2H, m), 2.67 (1H, m), 2.13 (2H, m), 1.76 (2H, m), 1.43 (2H, m), 0.95 (6H, d). MS m/z: 475.15, 477.13 [M+H]$^+$.

Example 188

5-((3,5-dichloropyridin-4-yl)thio)-4-nitro-N-(1,2,2,6,6-pentamethylpiperidin-4-yl)thiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 1,2,2,6,6-pentamethylpiperidin-4-amine (20.4 mg, 0.12 mmol). The title compound was obtained as a solid (16.9 mg, 34% yield). MS m/z: 503.09, 505.08 [M+H]$^+$.

Example 189

5-((3,5-dichloropyridin-4-yl)thio)-N-(1-methylpiperidin-3-yl)-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 1-methylpiperidin-3-amine (13.7 mg, 0.12 mmol). The title compound was obtained as a solid (23.0 mg, 51% yield). MS m/z: 447.02, 449.02 [M+H]$^+$.

Example 190

5-((3,5-dichloropyridin-4-yl)thio)-N-((1-methylpiperidin-4-yl)methyl)-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 2-(1-ethylpiperidin-4-yl)ethanamine (15.6 mg, 0.12 mmol). The title compound was obtained as a solid (28.1 mg, 61% yield). MS m/z: 461.02, 463.02 [M+H]$^+$.

Example 191

5-((3,5-dichloropyridin-4-yl)thio)-4-nitro-N-(3-(pyrrolidin-1-yl)propyl)thiophene-2-carboxamide: Prepared according to the procedure described for example 70 from 5-[(3,5-dichloro-4-pyridyl)sulfanyl]-4-cyano-thiophene-2- carboxylic acid (150 mg, 0.43 mmol), 2-(7-Aza-1H-benzotriazole-1-yl)-1,1,3,3-tetramethyluronium hexafluorophosphate (HATU) (180.0 mg, 0.47 mmol) and 3-(pyrrolidin-1-yl)propan-1-amine (65.0 mg, 0.51 mmol). The title compound was obtained as a solid (70.0 mg, 35% yield). $^1$H NMR (400 MHz, d$_6$-DMSO) δ: 9.00 (2H, m), 8.93 (1H, t), 8.39 (1H, s), 3.48 (2H, m), 3.25 (2H, m), 3.09 (2H, m), 3.03 (2H, m), 2.03 (3H, m), 1.81 (3H, m). MS m/z: 460.98, 462.98 [M+H]$^+$.

Example 192

5-((3,5-dichloropyridin-4-yl)thio)-N-(4-(2-(dimethylamino)ethoxy)phenyl)-4-nitrothiophene-2-carboxamide: Prepared according to the procedure described for example 44 from 5-[(3,5-dichloro-4-pyridyl)sulfanyl]-4-nitrothiophene-2-carboxylic acid (35 mg, 0.1 mmol) and 4-(2-(dimethylamino)ethoxy)aniline (17.0 mg, 0.12 mmol). The title compound was obtained as a solid (17.5 mg, 34% yield). MS m/z: 513.02, 515.02 [M+H]$^+$.

Example 193

5-[(3,5-dichloro-4-pyridyl)sulfanyl]-N-[4-(3-dimethylaminopropoxy)phenyl]-4-nitro-thiophene-2-carboxamide: Prepared according to the procedure described for example 44 from 5-[(3,5-dichloro-4-pyridyl)sulfanyl]-4-nitrothiophene-2-carboxylic acid (35 mg, 0.1 mmol) and 4-(3-(dimethylamino)propoxy)aniline (21.6 mg, 0.12 mmol). The title compound was obtained as a solid (17.5 mg, 33% yield). MS m/z: 527.16, 525.16 [M+H]$^+$.

Example 194

5-((3,5-dichloropyridin-4-yl)thio)-N-(3-(methylthio)propyl)-4-nitrothiophene-2-carboxamide: Prepared according to the procedure described for example 70 from 5-[(3,5-dichloro-4-pyridyl)sulfanyl]-4-nitro-thiophene-2-carboxylic acid (500 mg, 1.43 mmol), 2-(7-Aza-1H-benzotriazole-1-yl)-1,1,3,3-tetramethyluronium hexafluorophosphate (HATU) (594 mg, 1.56 mmol) and 4-(3-dimethylaminopropoxy)-3-methoxy-aniline (180 mg, 1.7 mmol). The title compound was obtained as a solid (275 mg, 44% yield) MS m/z: 436.25, 438.26 [M+H]$^+$.

Example 195

Step A:
tert-butyl 3-(5-((3,5-dichloropyridin-4-yl)thio)-4-nitrothiophene-2-carboxamido)pyrrolidine-1-carboxylate: Prepared according to the procedure described for example 70 from 5-[(3,5-dichloro-4-pyridyl)sulfanyl]-4-nitrothiophene-2-carboxylic acid (3.0 g, 8.5 mmol) 2-(7-Aza-1H-benzotriazole-1-yl)-1,1,3,3-tetramethyluronium hexafluorophosphate (HATU) (3.5 g, 9.3 mmol) and tert-butyl 3-aminopyrrolidine-1-carboxylate (1.86 g, 0.52 mmol). The title compound was obtained as a solid (3.1 g, 70% yield). $^1$H NMR (400 MHz, d$_6$-DMSO) δ: 8.98 (2H, s), 8.91 (1H, m), 8.52 (1H, s), 4.29 (1H, m), 3.49 (1H, m), 3.30 (1H, m), 3.15 (1H, m), 2.06 (1H, m), 2.03 (1H, m), 1.83 (1H, m), 1.40 (9H, s).
Step B:
5-((3,5-dichloropyridin-4-yl)thio)-4-nitro-N-(pyrrolidin-3-yl)thiophene-2-carboxamide: tert-butyl 3-(5-((3,5-dichloropyridin-4-yl)thio)-4-nitrothiophene-2-carboxamido)pyrrolidine-1-carboxylate (3.0 g, 5.63 mmol) from the above was added to a solution of hydrogen chloride in ethanol (2.0 M, 20 mL) and ethanol (30 mL), and the resulting mixture was stirred at ambient temperature for 4 hours. After this time, the mixture was concentrated, washed with dry ether and dried in vacuo overnight to afford the title product as a white solid (2.2 g, 91% yield). $^1$H NMR (400 MHz, d$_6$-DMSO) δ: 8.98 (2H, m), 8.86 (1H, d), 8.78 (1H, m), 8.50 (1H, s), 4.20 (1H, m), 2.94 (2H, m), 2.79 (1H, m), 2.67 (1H, m), 1.93 (1H, m), 1.67 (1H, m). MS m/z: 419.20, 421.20 [M+H]$^+$.

Example 196

5-((3,5-dichloropyridin-4-yl)thio)-4-nitro-N-(piperidin-4-yl)thiophene-2-carboxamide: Prepared according to the procedure described for step B of example 195 from 5-((3,5-dichloropyridin-4-yl)thio)-N-(4-(dimethylamino)phenyl)-4-nitrothiophene-2-carboxamide from example 85 (3.0 g, 5.63 mmol) the title product was afforded as a white solid (2.3 g, 94% yield). $^1$H NMR (400 MHz, d$_6$-DMSO) δ: 8.98 (2H, m), 8.91 (1H, d), 8.56 (1H, s), 3.95 (1H, m), 3.28 (2H, m), 2.97 (2H, m), 1.93 (2H, m), 1.77 (2H, m). MS m/z: 433.07, 435.08 [M+H]$^+$.

Example 197

5-((3,5-dichloropyridin-4-yl)thio)-N-(1-ethylpyrrolidin-3-yl)-4-nitrothiophene-2-carboxamide: To a solution of 5-((3,5-dichloropyridin-4-yl)thio)-4-nitro-N-(pyrrolidin-3-yl)thiophene-2-carboxamide (0.1 g, 0.24 mmol) and acetaldehyde (31.9 mg, 0.72 mmol) in tetrahydrofuran (3.0 mL) under nitrogen, was added 2 drops of acetic acid. The resulting mixture was stirred at ambient temperature for 30 minutes. Then sodium triacetoxyboronhidride was added and the reaction mixture was stirred at ambient temperature for additional 12 hours. After this time, the reaction mixture was diluted with ethylacetate and washed with brine and water. The organic layer was separated, dried (Na$_2$SO$_4$) and concentrated. The crude residue was purified by silica gel chromatography using a 90:10 mixture of dichloromethane and methanol as eluent to afford the title product as a solid (40 mg, 37% yield). $^1$H NMR (400 MHz, d$_6$-DMSO) δ: 7.57 (1H, m), 7.44 (1H, m), 7.06 (1H, m), 4.07 (2H, m), 3.81 (3H, s), 3.812 (3H, s), 3.807 (2H, s), 2.33 (2H, m), 2.13 (6H, s), 1.86 (2H, m). MS m/z: 268.26 [M+H]$^+$.

Example 198

N-(1-cyclopropylpyrrolidin-3-yl)-5-((3,5-dichloropyridin-4-yl)thio)-4-nitrothiophene-2-carboxamide: To a solution of 5-((3,5-dichloropyridin-4-yl)thio)-4-nitro-N-(pyrrolidin-3-yl)thiophene-2-carboxamide (0.20 g, 0.48 mmol), (2-cyclopropoxyethoxy)trimethylsilane (498 mg, 2.86 mmol) and acetic acid (286 mg, 4.77 mmol) in methanol (10 mL) under nitrogen, was added sodium borohydride cyanide powder (150 mg, 2.38 mmol) by small portion. The resulting reaction mixture was heated under reflux for 4 hours. After this time, the reaction mixture was passed through a celite cartridge and the organic solution was concentrated. The resulting residue was dissolved in ethyl acetate and was washed with sodium bicarbonate solution and brine. The organic layer was separated, dried (Na$_2$SO$_4$) and concentrated. The crude was purified by reverse phase HPLC to afford the titled product as a solid (12.0 mg, 5% yield) $^1$H NMR (400 MHz, d$_6$-DMSO) δ: 8.99 (2H, m), 8.87 (1H, d), 8.54 (1H, s), 4.23 (1H, m), 2.83 (2H, m), 2.07 (1H, m), 1.63 (2H, m), 1.23 (2H, m), 0.48 (2H, m), 0.38 (2H, m). MS m/z: 459.08, 461.07 [M+H]$^+$.

Example 199

N-(1-acetylpyrrolidin-3-yl)-5-((3,5-dichloropyridin-4-yl)thio)-4-nitrothiophene-2-carboxamide: To a solution of 5-((3,5-dichloropyridin-4-yl)thio)-4-nitro-N-(pyrrolidin-3-yl)thiophene-2-carboxamide (0.15 g, 0.36 mmol) and acetyl chloride (41.0 mg, 0.54 mmol) in tetrahydrofuran (5.0 mL), was added triethylamine (54.2 mg, 0.54 mmol). The resulting reaction mixture was stirred at ambient temperature for 4 hours. After this time, the reaction mixture was quenched with ice water and stirred at room temperature for 20 minutes and the resulting precipitate was collected by filtration, washed with water (10 mL) and dried in vacuo at 40° C. overnight to afford the title product as an solid (80 mg, 48% yield). $^1$H NMR (400 MHz, $d_6$-DMSO) δ: 8.98 (2H, m), 8.91 (1H, d), 8.51(1H, m), 3.68 (1H, m), 3.50 (2H, m), 3.23 (2H, m), 2.09 (1H, m), 1.94 (3H, m). MS m/z: 461.17, 363.17 [M+H]$^+$.

Example 200

5-((3,5-dichloropyridin-4-yl)thio)-N-(3-(dimethylamino)-1-phenylpropyl)-4-nitrothiophene-2-carboxamide: Prepared according to the procedure described for example 44 from 5-[(3,5-dichloro-4-pyridyl)sulfanyl]-4-nitrothiophene-2-carboxylic acid (35 mg, 0.1 mmol) and N1,N1-dimethyl-3-phenylpropane-1,3-diamine (17.8 mg, 0.1 mmol). The title compound was obtained as a solid (15.8 mg, 31% yield). MS m/z: 510.89, 513.89 [M+H]$^+$.

Example 201

N-(5-(tert-butyl)isoxazol-3-yl)-5-((3,5-dichloropyridin-4-yl)thio)-4-nitrothiophene-2-carboxamide: Prepared according to the procedure described for example 50 from 5-((3,5-dichloropyridin-4-yl)thio)-4-nitrothiophene-2-carboxylic acid (200 mg, 0.57 mmol) and 5-tert-butylisoxazol-3-amine (95 mg, 0.68 mmol). The title compound was obtained as a yellow solid (45 mg, 17% yield). $^1$H NMR (400 MHz, $d_6$-DMSO) δ: 10.78 (1H, s), 9.01 (2H, s), 8.75 (1H, m), 8.01 (2H, m), 7.82 (2H, m), 2.51 (3H, s). MS m/z: 466.03, 468.03 [M+H]$^+$.

Example 202

5-((3,5-dichloropyridin-4-yl)thio)-4-nitro-N-(quinuclidin-3-yl)thiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and quinicidine HCl salt (19.9 mg, 0.1 mmol). The title compound was obtained as a solid (3.7 mg, 8% yield). MS m/z: 459.01, 461.01 [M+H]$^+$.

Example 203

Step A:
Ethyl 4-cyano-5-(methylsulfonyl)thiophene-2-carboxylate: To a solution of ethyl 4-cyano-5-(methylthio)thiophene-2-carboxylate (0.908 g, 4.0 mmol) in dichloromethane (60 mL) cooled at 0° C. in an ice bath, was added m-chloroperoxybenzoic acid (2.76 g, 16 mmol). After the addition, the temperature was warmed up to ambient temperature and stirred at this temperature for 6 hours. After this time, the reaction mixture was diluted with dichloromethane (60 mL) and washed with saturated sodium bicarbonate (25 mL×3) followed by water (30 mL×2) and brine (25 mL×2). The organic layer was separated, dried (Na$_2$SO$_4$) and concentrated under vacuum to afford a white solid as the title product (0.82 g, 87% yield). $^1$H NMR (400 MHz, CDCl$_3$) δ: 8.42 (1H, s), 4.38 (2H, q), 3.57 (3H, s), 1.32 (3H, t). MS m/z: 277.16 [M+H]$^+$.

Step B:
Ethyl 4-cyano-5-((3,5-dichloropyridin-4-yl)thio)thiophene-2-carboxylate: To a 5 mL Biotage microwave reaction vessel was charged with a solution of Ethyl 4-cyano-5-(methylsulfonyl)thiophene-2-carboxylate (0.26 g, 1 mmol) in isopropanol (1.5 mL), 3,5-dichloro-1-oxido-pyridin-1-ium-4-thiol sodium salt (0.2 g, 1 mmol) and N-ethyl-N-isopropylpropan-2-amine (0.645 g, 5.0 mmol). The resulting reaction mixture was sealed and heated at 150° C. for 10 minutes under microwave irradiation (Biotage Initiator 8). After cooling down, a precipitation was formed and the solid was removed by filtration. The organic solution was concentrated under vacuo to give a brown oil residue. The residue was re-dissolved in methanol (3 mL) and extracted with hexane (15 mL×4). The organic layer was separated and concentrated under vacuum to afford a solid as the title product (180 mg, 50% yield). MS m/z: 358.94, 360.94 [M+H]$^+$.

Step C:
4-cyano-5-((3,5-dichloropyridin-4-yl)thio)thiophene-2-carboxylic acid: Prepared according to the procedure described for Step A of example 44 from Ethyl 4-cyano-5-((3,5-dichloropyridin-4-yl)thio)thiophene-2-carboxylate (180 mg, 0.5 mmol). The title compound was obtained as a solid (94 mg, 28% yield). MS m/z: 331.92, 332.91 [M+H]$^+$.

Step D:
4-cyano-5-((3,5-dichloropyridin-4-yl)thio)-N-(1-methylpiperidin-4-yl)thiophene-2-carboxamide: Prepared according to the procedure described for Step B of example 44 from 4-cyano-5-((3,5-dichloropyridin-4-yl)thio)thiophene-2-carboxylic acid (35 mg, 0.15 mmol). The title compound was obtained as a solid (11 mg, 25% yield). MS m/z: 427.02, 429.02 [M+H]$^+$.

Example 204

4-cyano-5-((3,5-dichloropyridin-4-yl)thio)-N-(4-(3-(dimethylamino)propoxy)-thiophene-2-carboxamide: Prepared according to the procedure described for example 203 from 5-[(3,5-dichloro-4-pyridyl)sulfanyl]-4-cyano-thiophene-2-carboxylic acid (35 mg, 0.11 mmol) from step C of example 203 and 4-(3-dimethylaminopropoxy)-aniline (29 mg, 0.15 mmol). The crude material was purified by reverse phase HPLC and the title compound was obtained as a yellow solid (15.0 mg, 27% yield). MS m/z: 507.15, 509.15 [M+H]$^+$.

Example 205

Step A:
3-(2-methoxy-4-nitrophenoxy)-N,N-dimethylpropan-1-amine: To a solution of 2-methoxy-4-nitrophenol (1.0 g, 5.9 mmol) and 3-chloro-N-methylpropan-1-aminium hydrochloride salt (1.03 g, 6.5 mmol) in N,N-dimethylformide (10 mL), was added potassium carbonate (2.03 g, 14.7 mmol). The resulting reaction mixture was heated at 120° C. for 18 hours. After this time, TLC analysis showed no starting material remaining so the mixture was quenched with water and extracted with ethyl acetate. The organic layer was separated, dried (Na$_2$SO$_4$) and concentrated. The crude residue was purified by silica gel chromatography using a 95:5 mixture of dichloromethane and methanol as eluent to afford the title product as yellow oil (0.8 g, 53% yield). $^1$H NMR (400 MHz, $d_6$-DMSO) δ: 7.57 (1H, m), 7.44 (1H, m), 7.06 (1H, m), 4.07

(2H, m), 3.81 (3H, s), 3.812 (3H, s), 3.807 (2H, s), 2.33 (2H, m), 2.13 (6H, s), 1.86 (2H, m). MS m/z: 268.26 [M+H]$^+$.

Step B:

4-(3-(dimethylamino)propoxy)-3-methoxyaniline: To a two necked 25 mL round bottom flask, charged with 3-(2-methoxy-4-nitrophenoxy)-N,N-dimethylpropan-1-amine (0.5 g, 1.96 mmol) from above, 10 mL of methanol followed by sodium borohydride (0.2 g, 4.2 mmol) and 10% Pd/C (0.05 g). The resulting reaction mixture was stirred at ambient temperature for 1 hour. After this time, the reaction mixture was passed through a cellite cartridge to remove Pd/C. The organic solution was concentrated under vacuo to give a brown solid residue. The resulting solid was treated with hydrochloric acid (2 M in ether). After stirring for 10 minutes, the solid which formed was collected by filtration and washed with water (10 mL) and dried under vacuum to afford the corresponding hydrochloride salt of the title product (0.3 g, 60% yield). $^1$H NMR (400 MHz, d$_6$-DMSO with D2O) δ: 7.07 (1H, m), 6.99 (1H, m), 6.85 (1H, m), 4.04 (2H, m), 3.79 (3H, s), 3.17 (2H, m), 2.77 (6H, s), 2.13 (2H, m). MS m/z: 225.22 [M+H]$^+$.

Step C:

4-cyano-5-((3,5-dichloropyridin-4-yl)thio)-N-(4-(3-(dimethylamino)propoxy)-3-methoxyphenyl)thiophene-2-carboxamide: Prepared according to the procedure described for example 70 from 5-[(3,5-dichloro-4-pyridyl)sulfanyl]-4-cyano-thiophene-2-carboxylic acid (100 mg, 0.3 mmol) from step C of example 203, 2-(7-Aza-1H-benzotriazole-1-yl)-1,1,3,3-tetramethyluronium hexafluorophosphate (HATU) (126 mg, 0.33 mmol) and 4-(3-dimethylaminopropoxy)-3-methoxy-aniline (96 mg, 0.36 mmol) from the above. The crude material was purified by reverse phase HPLC and the title compound was obtained as a yellow solid (15.0 mg, 9% yield). $^1$H NMR (400 MHz, d$_6$-DMSO) δ: 10.33 (1H, s), 8.85 (2H, s), 8.24 (1H, s), 7.29 (1H, m), 7.18 (1H, m), 6.94 (1H, m), 3.94 (2H, m), 2.34 (2H, m), 2.14 (6H, s), 1.84 (3H, s), 1.81 (2H, m). MS m/z: 537.17, 539.15 [M+H]$^+$.

Example 206

4-cyano-5-((3,5-dichloropyridin-4-yl)thio)-N-(3-(3-(dimethylamino)propoxy)benzyl)thiophene-2-carboxamide: Prepared according to the procedure described for example 44 from 5-[(3,5-dichloro-4-pyridyl)sulfanyl]-4-cyano-thiophene-2-carboxylic acid (35 mg, 0.11 mmol) from step C of example 203 and 4-(3-dimethylaminopropoxy)-benzylamine (30 mg, 0.15 mmol). The crude material was purified by reverse phase HPLC and the title compound was obtained as a yellow solid (25.7 mg, 45% yield). MS m/z: 520.89, 522.89 [M+H]$^+$.

Example 207

4-cyano-5-((3,5-dichloropyridin-4-yl)thio)-N-(quinolin-3-yl)thiophene-2-carboxamide: Prepared according to the procedure described for example 44 from 5-[(3,5-dichloro-4-pyridyl)sulfanyl]-4-cyano-thiophene-2-carboxylic acid (47 mg, 0.14 mmol) from step C of example 203 and 3-aminoquinoline (40 mg, 0.15 mmol). The crude material was purified by reverse phase HPLC and the title compound was obtained as a yellow solid (14.9 mg, 23% yield). MS m/z: 456.98, 458.97 [M+H]$^+$.

Example 208

4-cyano-5-((3,5-dichloropyridin-4-yl)thio)-N-(4-(methylsulfonyl)phenyl)thiophene-2-carboxamide: Prepared according to the procedure described for example 44 from 5-[(3,5-dichloro-4-pyridyl)sulfanyl]-4-cyano-thiophene-2-carboxylic acid (47 mg, 0.14 mmol) from step C of example 203 and 4-methylsulfonylaniline (26.0 mg, 0.15 mmol). The crude material was purified by reverse phase HPLC and the title compound was obtained as a yellow solid (3.5 mg, 5% yield). MS m/z: 484.94, 485.94 [M+H]$^+$.

Example 209

Ethyl 2-(5-((3,5-dichloropyridin-4-yl)thio)-4-nitrothiophene-2-carboxamido)acetate: Prepared according to the procedure described for example 70 from 5-[(3,5-dichloro-4-pyridyl)sulfanyl]-4-nitro-thiophene-2-carboxylic acid (1.5 g, 4.27 mmol) and ethyl 2-aminoacetate (696 mg, 5.12 mmol). The title compound was obtained as a solid (1.1 g, 59% yield). $^1$H NMR (400 MHz, d$_6$-DMSO) δ: 9.36 (1H, t), 8.98 (2H, s), 8.47 (1H, s), 4.11 (2H, q), 3.97 (2H, s), 1.19 (3H, t). MS m/z: 434.08, 436.06 [M+H]$^+$.

Example 210

2-(5-((3,5-dichloropyridin-4-yl)thio)-4-nitrothiophene-2-carboxamido)acetic acid: Prepared according to the procedure described for step A of example 44 from Ethyl 2-(5-((3,5-dichloropyridin-4-yl)thio)-4-nitrothiophene-2-carboxamido)acetate (1.0 g, 2.29 mmol). The title compound was obtained as a white solid (0.67 g, 71% yield). $^1$H NMR (400 MHz, d$_6$-DMSO) δ: 8.98 (2H, m), 8.82 (1H, m), 8.49 (1H, m), 3.58 (2H, m). MS m/z: 406.10, 408.06 [M+H]$^+$.

Example 211

5-((3,5-dichloropyridin-4-yl)thio)-N-(2-(4-hydroxypiperidin-1-yl)-2-oxoethyl)-4-nitrothiophene-2-carboxamide: Prepared according to the procedure described for example 70 from 2-(5-((3,5-dichloropyridin-4-yl)thio)-4-nitrothiophene-2-carboxamido)acetic acid (200 mg, 0.49 mmol) from example 210 and piperidin-4-ol (59.0 mg, 0.59 mmol). The title compound was obtained as a solid (45.0 mg, 19% yield). $^1$H NMR (400 MHz, d$_6$-DMSO) δ: 9.06 (1H, m), 8.98 (2H, m), 8.51 (1H, s), 4.75 (1H, m), 4.07 (2H, m), 3.87 (1H, m), 3.66 (2H, m), 3.13 (1H, m), 2.98 (1H, m), 1.71 (2H, m), 1.23 (2H, m). MS m/z: 489.31, 491.26 [M+H]$^+$.

Example 212

5-((3,5-dichloropyridin-4-yl)thio)-N-(2-(3-hydroxypiperidin-1-yl)-2-oxoethyl)-4-nitrothiophene-2-carboxamide: Prepared according to the procedure described for example 70 from 2-(5-((3,5-dichloropyridin-4-yl)thio)-4-nitrothiophene-2-carboxamido)acetic acid (200 mg, 0.49 mmol) from example 210 and piperidin-3-ol (59.0 mg, 0.59 mmol). The title compound was obtained as a solid (25.0 mg, 11% yield). $^1$H NMR (400 MHz, d$_6$-DMSO) δ: 9.04 (1H, m), 8.51 (1H, s), 4.87 (1H, m), 4.08 (2H, m), 3.58 (1H, m), 3.48 (1H, m), 3.38 (1H, m), 3.15 (1H, m), 2.60 (1H, m), 1.85 (1H, m), 1.75 (1H, m), 1.47 (1H, m), 1.33 (1H, m). MS m/z: 491.23, 493.26 [M+H]$^+$.

Example 213

5-((3,5-dichloropyridin-4-yl)thio)-N-(2-((3-methoxypropyl)amino)-2-oxoethyl)-4-nitrothiophene-2-carboxamide: Prepared according to the procedure described for example 70 from 2-(5-((3,5-dichloropyridin-4-yl)thio)-4-nitrothiophene-2-carboxamido)acetic acid (120.0 mg, 0.29 mmol) from example 210 and 3-methoxypropylamine (31.4 mg, 0.35 mmol). The title compound was obtained as a solid (20.0 mg, 15% yield). $^1$H NMR (400 MHz, d$_6$-DMSO) δ: 9.19 (1H, m), 8.99 (2H, m), 8.47 (1H, s), 7.94 (1H, m), 3.77 (2H, m), 3.29 (2H, m), 3.19 (3H, s), 3.07 (2H, m), 1.60 (2H, m). MS m/z: 477.11, 479.10 [M+H]$^+$.

Example 214

5-((3,5-dichloropyridin-4-yl)thio)-N-(2-((2-methoxyethyl)amino)-2-oxoethyl)-4-nitrothiophene-2-carboxamide: Prepared according to the procedure described for example 70 from 2-(5-((3,5-dichloropyridin-4-yl)thio)-4-nitrothiophene-2-carboxamido)acetic acid (120.0 mg, 0.29 mmol) from example 210 and 2-methoxyethylamine (26.4 mg, 0.35 mmol). The title compound was obtained as a solid (70.0 mg, 52% yield). $^1$H NMR (400 MHz, d$_6$-DMSO) δ: 9.17 (1H, m), 8.99 (2H, m), 8.47 (1H, s), 8.04 (1H, m), 3.79 (2H, m), 3.33 (2H, m), 3.22 (3H, s), 3.20 (2H, m). MS m/z: 463.09, 465.12 [M+H]$^+$.

Example 215

5-((3,5-dichloropyridin-4-yl)thio)-N-(2-(4-(hydroxymethyl)piperidin-1-yl)-2-oxoethyl)-4-nitrothiophene-2-carboxamide: Prepared according to the procedure described for example 70 from 2-(5-((3,5-dichloropyridin-4-yl)thio)-4-nitrothiophene-2-carboxamido)acetic acid (200 mg, 0.49 mmol) from example 210 and piperidin-4-ylmethanol (89.0 mg, 0.59 mmol). The title compound was obtained as a solid (25.0 mg, 8% yield). $^1$H NMR (400 MHz, d$_6$-DMSO) δ: 9.02 (1H, m), 8.98 (1H, s), 8.50 (1H, s), 4.47 (1H, m), 4.32 (1H, m), 4.06 (2H, m), 3.83 (1H, m), 3.24 (2H, m), 2.96 (1H, m), 2.51 (1H, m), 1.66 (2H, m), 1.60 (1H, m), 1.11 (1H, m), 1.05 (1H, m), 0.92 (1H, m). MS m/z: 505.31, 507.27 [M+H]$^+$.

Example 216

5-((3,5-dichloropyridin-4-yl)thio)-N-(2-(4-fluoropiperidin-1-yl)-2-oxoethyl)-4-nitrothiophene-2-carboxamide: Prepared according to the procedure described for example 70 from 2-(5-((3,5-dichloropyridin-4-yl)thio)-4-nitrothiophene-2-carboxamido)acetic acid (200 mg, 0.49 mmol) from example 210 and 4-fluoro-piperidine (60.0 mg, 0.59 mmol). The title compound was obtained as a solid (50.0 mg, 20% yield). $^1$H NMR (400 MHz, d$_6$-DMSO) δ: 9.07 (1H, m), 8.98 (2H, m), 8.51 (1H, s), 4.93 (1H, m), 4.10 (2H, m), 3.54 (2H, m), 3.44 (2H, m), 1.92 (1H, m), 1.74 (2H, m), 1.61 (1H, m). MS m/z: 491.39, 493.37 [M+H]$^+$.

Example 217

5-((3,5-dichloropyridin-4-yl)thio)-N-(2-((2-(dimethylamino)ethyl)amino)-2-oxoethyl)-4-nitrothiophene-2-carboxamide: Prepared according to the procedure described for example 44 from 2-(5-((3,5-dichloropyridin-4-yl)thio)-4-nitrothiophene-2-carboxamido)acetic acid (41 mg, 0.1 mmol) and 2-dimethylamine (24.0 mg, 0.2 mmol). The title compound was obtained as a solid (2.5 mg, 5% yield). MS m/z: 477.01, 479.01 [M+H]$^+$.

Example 218

5-((3,5-dichloropyridin-4-yl)thio)-N-(2-(4-methylpiperazin-1-yl)-2-oxoethyl)-4-nitrothiophene-2-carboxamide: Prepared according to the procedure described for example 70 from 2-(5-((3,5-dichloropyridin-4-yl)thio)-4-nitrothiophene-2-carboxamido)acetic acid (120.0 mg, 0.29 mmol) from example 210 and N-methyl-piperazine (35.3 mg, 0.35 mmol). The title compound was obtained as a solid (30.0 mg, 21% yield). $^1$H NMR (400 MHz, d$_6$-DMSO) δ: 9.05 (1H, m), 8.99 (2H, m), 8.51 (1H, s), 4.07 (2H, m), 3.42 (2H, m), 3.32 (2H, m), 2.29 (2H, m), 2.24 (2H, m), 2.17 (3H, s). MS m/z: 488.13, 490.15 [M+H]$^+$.

Example 219

5-((3,5-dichloropyridin-4-yl)thio)-N-(2-((2,2-difluoroethyl)amino)-2-oxoethyl)-4-nitrothiophene-2-carboxamide: Prepared according to the procedure described for example 70 from 2-(5-((3,5-dichloropyridin-4-yl)thio)-4-nitrothiophene-2-carboxamido)acetic acid (120.0 mg, 0.29 mmol) from example 210 and 2,2-di-fluoro-ethylamine (28.5 mg, 0.35 mmol). The title compound was obtained as a solid (84.0 mg, 62% yield). $^1$H NMR (400 MHz, d$_6$-DMSO) δ: 9.24 (1H, m), 8.99 (2H, m), 8.47 (1H, s), 8.36 (1H, m), 5.98 (1H, m), 3.85 (2H, m), 3.50 (2H, m). MS m/z: 469.05, 471.06 [M+H]$^+$.

Example 220

N-(2-cyclohexylamino)-2-oxoethyl)-5-((3,5-dichloropyridin-4-yl)thio)-4-nitrothiophene-2-carboxamide: Prepared according to the procedure described for example 70 from 2-(5-((3,5-dichloropyridin-4-yl)thio)-4-nitrothiophene-2-carboxamido)acetic acid (200 mg, 0.49 mmol) from example 210 and cyclohexylamine (58.0 mg, 0.59 mmol). The title compound was obtained as a solid (20.0 mg, 8% yield). $^1$H NMR (400 MHz, d$_6$-DMSO) δ: 9.12 (1H, m), 8.99 (2H, m), 8.48 (1H, s), 7.81 (1H, m), 3.77 (2H, m), 3.51 (1H, m), 1.67 (4H, m), 1.55 (1H, m), 1.25 (2H, m), 1.19 (3H, m). MS m/z: 489.02, 491.06 [M+H]$^+$.

Example 221

5-((3,5-dichloropyridin-4-yl)thio)-4-nitro-N-(2-oxo-2-(piperidin-1-yl)ethyl)thiophene-2-carboxamide: Prepared according to the procedure described for example 70 from 2-(5-((3,5-dichloropyridin-4-yl)thio)-4-nitrothiophene-2-carboxamido)acetic acid (200 mg, 0.49 mmol) from example 210 and piperidine (50.0 mg, 0.59 mmol). The title compound was obtained as a solid (45.0 mg, 22% yield). $^1$H NMR (400 MHz, d$_6$-DMSO) δ: 9.06 (1H, m), 8.98 (2H, m), 8.51 (1H, s), 4.06 (2H, m), 3.38 (4H, m), 1.57 (2H, m), 1.48 (2H, m), 1.24 (2H, m). MS m/z: 475.08, 477.08 [M+H]$^+$.

Example 222

5-((3,5-dichloropyridin-4-yl)thio)-N-(2-((1-methylpiperidin-4-yl)amino)-2-oxoethyl)-4-nitrothiophene-2-carboxamide: Prepared according to the procedure described for example 70 from 2-(5-((3,5-dichloropyridin-4-yl)thio)-4-nitrothiophene-2-carboxamido)acetic acid (120.0 mg, 0.29 mmol) from example 210 and N-methyl-4-amino-piperidine (40.2 mg, 0.35 mmol). The title compound was obtained as a solid (30.0 mg, 21% yield). $^1$H NMR (400 MHz, d$_6$-DMSO) δ: 9.14 (1H, m), 8.99 (2H, m), 8.48 (1H, s), 7.90 (1H, m), 3.77 (2H, m), 3.48 (1H, m), 2.69 (2H, m), 2.15 (3H, s), 1.92 (2H, m), 1.67 (2H, m), 1.44 (2H, m). MS m/z: 502.15, 504.12 [M+H]$^+$.

Example 223

Step A:
N-(3-((tert-butyldimethylsilyl)oxy)propyl)-5-((3,5-dichloropyridin-4-yl)thio)-4-nitrothiophene-2-carboxamide:

Prepared according to the procedure described for example 70 from 5-[(3,5-dichloro-4-pyridyl)sulfanyl]-4-nitrothiophene-2-carboxylic acid (1.5 g, 4.3 mmol) and 3-(tert-butyl(dimethyl)silyl)oxypropan-1-amine (0.98 g, 5.12 mmol). The title compound was obtained as a yellow solid (1.1 g, 49% yield).

Step B:

5-((3,5-dichloropyridin-4-yl)thio)-N-(3-hydroxypropyl)-4-nitrothiophene-2-carboxamide: N-(3-((tert-butyldimethylsilyl)oxy)propyl)-5-((3,5-dichloropyridin-4-yl)thio)-4-nitrothiophene-2-carboxamide (1.0 g, 1.92 mmol) from the above was added to a solution of hydrogen chloride in ether (2.0 M, 15 mL) and dry ether (15 mL), and the resulting mixture was stirred at ambient temperature for 1 hour. After this time, the reaction mixture was diluted with water, extracted with ethyl acetate and washed with brine and water. The organic layer was separated, dried ($Na_2SO_4$) and concentrated. The crude residue was purified by silica gel chromatography using a 97:3 mixture of dichloromethane and methanol as eluent to afford the title product as a solid (550 mg, 37% yield). $^1$H NMR (400 MHz, $d_6$-DMSO) δ: 8.99 (2H, s), 8.81 (1H, m), 8.43 (1H, s), 3.41 (2H, m), 3.24 (2H, m), 1.61 (2H, m).

Step C:

5-((3,5-dichloropyridin-4-yl)thio)-4-nitro-N-(3-oxopropyl)thiophene-2-carboxamide: To a solution of 5-((3,5-dichloropyridin-4-yl)thio)-N-(3-hydroxypropyl)-4-nitrothiophene-2-carboxamide (800 mg, 1.2 mmol) in chloroform (15 mL) was added Dessmartin reagent (611 mg, 1.4 mmol) at 0° C. The resulting reaction mixture was warmed up to ambient temperature and stirred at this temperature for 6 hours. After this time, the reaction mixture was diluted with chloroform and washed with brine and water. The organic layer was separated, dried ($Na_2SO_4$) and concentrated. The crude residue was purified by silica gel chromatography using a 97:3 mixture of dichloromethane and methanol as eluent to afford the title product as a solid (430 mg, 89% yield). $^1$H NMR (400 MHz, $d_6$-DMSO) δ: 9.64 (1H, s), 8.98 (2H, s), 8.91 (1H, m), 8.39 (1H, s), 3.46 (2H, m), 2.66 (2H, m). MS m/z: 404.04, 406.03 [M+H]$^+$.

Step D:

5-((3,5-dichloropyridin-4-yl)thio)-N-(3-(3-hydroxypiperidin-1-yl)propyl)-4-nitrothiophene-2-carboxamide: To a solution of 5-((3,5-dichloropyridin-4-yl)thio)-4-nitro-N-(3-oxopropyl)thiophene-2-carboxamide (0.13 g, 0.32 mmol) and 3-hydroxy-piperidine (89.0 mg, 0.38 mmol) in tetrahydrofuran (3.0 mL) under nitrogen, was added acetic acid (0.2 mL). The resulting mixture was stirred at ambient temperature for 30 minutes. Then sodium triacetoxyboronhydride was added and the reaction mixture was stirred at ambient temperature for additional 4 hours. After this time, the reaction mixture was diluted with water and extracted with ethylacetate. The organic layer was separated, dried ($Na_2SO_4$) and concentrated. The crude residue was purified by silica gel chromatography using a 90:10 mixture of dichloromethane and methanol as eluent to afford the title product as a solid (14.0 mg, 37% yield). $^1$H NMR (400 MHz, $d_6$-DMSO) δ: 8.99 (2H, m), 8.83 (1H, m), 8.41 (1H, s), 4.58 (1H, m), 3.19 (2H, m), 2.80 (1H, m), 2.61 (1H, m), 2.27 (2H, m), 1.76 (2H, m), 1.61 (3H, m), 1.38 (1H, m), 1.23 (1H, m), 1.06 (1H, m). MS m/z: 491.11, 493.13 [M+H]$^+$.

Example 224

5-((3,5-dichloropyridin-4-yl)thio)-N-(3-(4-(dimethylamino)piperidin-1-yl)propyl)-4-nitrothiophene-2-carboxamide: Prepared according to the procedure described for step D of example 223 from 5-((3,5-dichloropyridin-4-yl)thio)-4-nitro-N-(3-oxopropyl)thiophene-2-carboxamide (100 mg, 0.23 mmol) and N,N-dimethylpiperidin-4-amine (6.0 mg, 0.28 mmol). The title compound was afforded as a solid (30.0 mg, 25% yield). $^1$H NMR (400 MHz, $d_6$-DMSO) δ: 9.02 (2H, s), 8.88 (1H, m), 8.46 (1H, s), 3.23 (2H, m), 2.93 (2H, m), 2.31 (9H, m), 1.91 (2H, m), 1.79 (2H, m), 1.66 (2H, m), 1.41 (2H, m). MS m/z: 518.16, 520.15 [M+H]$^+$.

Example 225

5-((3,5-dichloropyridin-4-yl)thio)-N-(3-(4-hydroxypiperidin-1-yl)propyl)-4-nitrothiophene-2-carboxamide: Prepared according to the procedure described for example 44 from 5-[(3,5-dichloro-4-pyridyl)sulfanyl]-4-nitrothiophene-2-carboxylic acid (35 mg, 0.1 mmol) and 4-(3-aminopropyl)cyclohexanol (15.8 mg, 0.12 mmol). The title compound was obtained as a solid (10 mg, 20% yield). MS m/z: 491.04, 493.04 [M+H]$^+$.

Example 226

1-(3-(5-((3,5-dichloropyridin-4-yl)thio)-4-nitrothiophene-2-carboxamido)propyl)piperidine-4-carboxamide: Prepared according to the procedure described for step D of example 223 from 5-((3,5-dichloropyridin-4-yl)thio)-4-nitro-N-(3-oxopropyl)thiophene-2-carboxamide (100 mg, 0.23 mmol) and piperidine-4-carboxamide (36.0 mg, 0.28 mmol). The title compound was afforded as a solid (20.0 mg, 17% yield). $^1$H NMR (400 MHz, $d_6$-DMSO) δ: 8.99 (2H, m), 8.85 (1H, m), 8.42 (1H, s), 7.21 (1H, m), 6.73 (1H, m), 3.19 (2H, m), 2.84 (2H, m), 2.25 (1H, m), 2.0 (1H, m), 1.8 (2H, m), 1.64 (4H, m), 1.53 (2H, m), 1.23 (1H, m). MS m/z: 518.33, 520.35 [M+H]$^+$.

Example 227

5-((3,5-dichloropyridin-4-yl)thio)-N-(3-(4-(hydroxymethyl)piperidin-1-yl)propyl)-4-nitrothiophene-2-carboxamide: Prepared according to the procedure described for step D of example 223 from 5-((3,5-dichloropyridin-4-yl)thio)-4-nitro-N-(3-oxopropyl)thiophene-2-carboxamide (150 mg, 0.37 mmol) and 4-piperidylmethanol (51.0 mg, 0.44 mmol). The title compound was afforded as a solid (30.0 mg, 17% yield). $^1$H NMR (400 MHz, $d_6$-DMSO) δ: 8.98 (2H, m), 8.83 (1H, m), 8.40 (1H, s), 3.38 (1H, m), 3.21 (4H, m), 2.83 (2H, m), 2.28 (2H, m), 1.60 (4H, m), 1.30 (1H, m), 1.00 (2H, m). MS m/z: 503.33, 505.32 [M+H]$^+$.

Example 228

5-((3,5-dichloropyridin-4-yl)thio)-N-(3-(4-fluoropiperidin-1-yl)propyl)-4-nitrothiophene-2-carboxamide: Prepared according to the procedure described for step D of example 223 from 5-((3,5-dichloropyridin-4-yl)thio)-4-nitro-N-(3-oxopropyl)thiophene-2-carboxamide (130 mg, 0.32 mmol) and 4-fluoropiperidine (59.0 mg, 0.38 mmol). The title compound was afforded as a solid (15.0 mg, 10% yield). $^1$H NMR (400 MHz, $d_6$-DMSO) δ: 8.98 (2H, m), 8.13 (1H, m), 8.41 (1H, s), 4.71 (1H, m), 3.32 (2H, m), 3.20 (2H, m), 2.27 (4H, m), 1.83 (2H, m), 1.65 (4H, m). MS m/z: 493.06, 495.05 [M+H]$^+$.

Example 229

5-((3,5-dichloropyridin-4-yl)thio)-N-(3-(4,4-dimethylpiperidin-1-yl)propyl)-4-nitrothiophene-2-carboxamide: Prepared according to the procedure described for step D of example 223 from 5-((3,5-dichloropyridin-4-yl)thio)-4-nitro-N-(3-oxopropyl)thiophene-2-carboxamide (100 mg, 0.23 mmol) and 4,4-dimethyl-piperidine (45.0 mg, 0.28 mmol). The title compound was afforded as a solid (30.0 mg, 26% yield). $^1$H NMR (400 MHz, d$_6$-DMSO) δ: 8.99 (2H, m), 8.43 (1H, s), 3.23 (2H, m), 2.95 (4H, m), 1.82 (2H, m), 1.35 (4H, m), 1.23 (2H, m), 0.94 (6H, s). MS m/z: 503.34, 505.37 [M+H]$^+$.

Example 230

5-((3,5-dichloropyridin-4-yl)thio)-4-nitro-N-(1-propylpiperidin-4-yl)thiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 1-propylpiperidin-4-amine (14.2 mg, 0.12 mmol). The title compound was obtained as a solid (10 mg, 21% yield). MS m/z: 474.98, 476.97 [M+H]$^+$.

Example 231

N-(1-cyclopropylpiperidin-4-yl)-5-((3,5-dichloropyridin-4-yl)thio)-4-nitrothiophene-2-carboxamide: Prepared according to the procedure described for example 198 from 5-((3,5-dichloropyridin-4-yl)thio)-4-nitro-N-(pyrrolidin-3-yl)thiophene-2-carboxamide (0.1 g, 0.24 mmol) and (2-cyclopropoxyethoxy)trimethylsilane (120 mg, 1.2 mmol). The title compound was obtained as a solid (25 mg, 22% yield). $^1$H NMR (400 MHz, d$_6$-DMSO) δ: 8.99 (2H, m), 8.60 (1H, m), 8.49 (1H, s), 3.61 (1H, m), 2.91 (2H, m), 2.22 (2H, m), 1.74 (2H, m), 1.57 (2H, m), 1.40 (2H, m), 1.18 (1H, m), 0.40 (2H, m), 0.39 (2H, m). MS m/z: 473.05, 475.05 [M+H]$^+$.

Example 232

N-(1-acetylpiperidin-4-yl)-5-((3,5-dichloropyridin-4-yl)thio)-4-nitrothiophene-2-carboxamide: Prepared according to the procedure described for example 199 from 5-((3,5-dichloropyridin-4-yl)thio)-4-nitro-N-(piperidin-4-yl)thiophene-2-carboxamide (0.2 g, 0.46 mmol) and acetyl chloride (53.0 mg, 0.69 mmol). The title compound was obtained as a solid (75 mg, 35% yield). $^1$H NMR (400 MHz, d$_6$-DMSO) δ:8.98 (2H, m), 8.67 (1H, m), 8.48 (1H, s), 4.28 (1H, m), 3.89 (1H, m), 3.80 (1H, m), 3.61 (1H, m), 3.13 (1H, m), 2.70 (1H, m), 2.00 (3H, s), 1.83 (1H, m), 1.76 (1H, m), 1.41 (1H, m), 1.28 (1H, m). MS m/z: 473.23, 475.25 [M+H]$^+$.

Example 233

5-((3,5-dichloropyridin-4-yl)thio)-N-(1-(methylsulfonyl)piperidin-4-yl)-4-nitrothiophene-2-carboxamide: Prepared according to the procedure described for example 199 from 5-((3,5-dichloropyridin-4-yl)thio)-4-nitro-N-(piperidin-4-yl)thiophene-2-carboxamide (0.2 g, 0.46 mmol) and methanesulfonyl chloride (79.0 mg, 0.69 mmol). The title compound was obtained as a solid (40 mg, 17% yield). $^1$H NMR (400 MHz, d$_6$-DMSO) δ: 8.98 (2H, s), 8.73 (1H, m), 8.48 (1H, s), 3.80 (1H, m), 3.77 (2H, m), 2.84 (3H, s), 2.81 (2H, m), 1.89 (2H, m), 1.56 (2H, m). MS m/z: 509.25, 511.28 [M+H]$^+$.

Example 234 tert-butyl (4-(5-((3,5-dichloropyridin-4-yl)thio)-4-nitrothiophene-2-carboxamido)phenyl)carbamate: Prepared according to the procedure described for example 70 from 5-[(3,5-dichloro-4-pyridyl)sulfanyl]-4-nitro-thiophene-2-carboxylic acid (0.5 g, 1.42 mmol), 2-(7-Aza-1H-benzotriazole-1-yl)-1,1,3,3-tetramethyluronium hexafluorophosphate (HATU) (0.6 g, 5.67 mmol) and tert-butyl 4-aminoaniline-1-carboxylate (0.36 g, 1.71 mmol). The title compound was obtained as a yellow solid (0.5 g, 65% yield). $^1$H NMR (400 MHz, d$_6$-DMSO) δ: 10.45 (1H, m), 9.34 (1H, m), 9.00 (2H, dd), 8.68 (1H, s), 5.56 (2H, dd), 7.40 (2H, dd), 1.46 (9H, s). MS m/z: 539.25, 541.23 [M+H]$^+$.

Example 235

N-(4-aminophenyl)-5-((3,5-dichloropyridin-4-yl)thio)-4-nitrothiophene-2-carboxamide: Prepared according to the procedure described for example 196 from tert-butyl (4-(5-((3,5-dichloropyridin-4-yl)thio)-4-nitrothiophene-2-carboxamido)phenyl)carbamate (0.50 g, 0.92 mmol). The title compound was obtained as a yellow solid (350 mg, 87% yield). $^1$H NMR (400 MHz, d$_6$-DMSO) δ: 10.63 (1H, br), 9.16 (2H, m), 8.78 (1H, s), 7.65 (2H, m), 7.15 (2H, m). MS m/z: 439.06, 441.08 [M+H]$^+$.

Example 236

Step A:
1H-benzo[d][1,2,3]triazole-1-carboximidamide HCl salt: To a 5 mL CEM microwave reaction vessel, was charged benzotriazole HCl salt (0.5 g, 3.2 mmol) and cyanamide (0.16 g, 3.9 mmol). The vessel was sealed and heated at 80° C. for 1 minute under microwave irradiation (CEM Discovery™). After this time, TLC analysis showed no starting material remaining so the mixture was diluted with ether. The precipitate was collected by filtration and washed with ether and dried under vacuum to afford the titled product as a white solid (0.45 g, 71% yield). $^1$H NMR (400 MHz, d$_6$-DMSO) δ: 10.14 (4H, s), 8.31 (1H, m), 8.05 (1H, m), 7.90 (1H, m), 7.67 ('H, m). MS m/z: 162.13 [M+H]$^+$.

Step B:
5-((3,5-dichloropyridin-4-yl)thio)-N-(4-guanidinophenyl)-4-nitrothiophene-2-carboxamide: To a solution of N-(4-aminophenyl)-5-((3,5-dichloropyridin-4-yl)thio)-4-nitrothiophene-2-carboxamide (0.2 g, 0.45 mmol) and 1H-benzo[d][1,2,3]triazole-1-carboximidamide HCl salt (0.18 g, 0.91 mmol) in acetonitrile (4 mL) was added triethylamine (0.13 mL, 0.91 mmol). After the addition, the resulting reaction mixture was heated at 60° C. for 24 hours. After this time, the reaction mixture was concentrated and purified by reverse phase HPLC to afford the titled product as a solid (20 mg, 9% yield). $^1$H NMR (400 MHz, d$_6$-DMSO) δ: 10.66 (1H, s), 9.68 (1H, m), 9.01 (2H, m), 8.74 (1H, s), 7.73 (2H, m), 7.39 (4H, m), 7.25 (3H, m), 7.12 (2H, dd). MS m/z: 483.06, 485.06 [M+H]$^+$.

Example 237

N-(1-carbamimidoylpiperidin-4-yl)-5-((3,5-dichloropyridin-4-yl)thio)-4-nitrothiophene-2-carboxamide: Prepared according to the procedure described for example 236 from 5-((3,5-dichloropyridin-4-yl)thio)-4-nitro-N-(piperidin-4-yl)thiophene-2-carboxamide (0.2 g, 0.43 mmol) from example 198 and 1H-benzo[d][1,2,3]triazole-1-carboximidamide HCl salt (0.17 g, 0.85 mmol) from example 236 step A. The titled product was afforded as a solid (15 mg, 7% yield). $^1$H NMR (400 MHz, d$_6$-DMSO) δ: 8.99 (2H, m), 8.72 (1H, m), 8.47 (1H, s), 7.37 (4H, m), 3.98 (1H, m), 3.83 (2H, m), 3.17 (2H, m), 1.86 (2H, m), 1.44 (2H, m). MS m/z: 475.11, 477.13 [M+H]$^+$.

Example 238

Step A:

N1,N1-dimethyl-N2-(5-nitropyridin-2-yl)ethane-1,2-diamine: To a round bottom flask, charged with 2-chloro-5-nitropyridine (1.0 g, 6.3 mmol), dimethylethane-1,2-diamine (0.55 g, 6.3 mmol), triethylamine (0.63 g, 6.3 mmol) and acetonitrile (10 mL). The resulting reaction mixture was stirred at ambient temperature for 9 hours. TLC analysis showed no acid remaining so the mixture was diluted with water and extracted with ethylacetate. The organic layer was separated and washed with brine and water, dried ($Na_2SO_4$) and concentrated. The crude material was purified by silica gel chromatography using a 95:5 mixture of dichloromethane and methanol as eluent to afford the title product as a brown solid (0.55 g, 42% yield). $^1$H NMR (400 MHz, $d_6$-DMSO) δ: 8.91 (1H, m), 8.09 (2H, m), 6.62 (1H, m), 4.10 (1H, m), 3.50 (2H, m), 3.17 (2H, m), 2.21 (6H, s). MS m/z: 211.14 [M+H]$^+$.

Step B:

N2-(2-(dimethylamino)ethyl)pyridine-2,5-diamine: To a round bottom flask, charged with N1,N1-dimethyl-N2-(5-nitropyridin-2-yl)ethane-1,2-diamine (0.4 g, 1.90 mmol) from above, 5 mL of ethanol, 5 mL water followed by iron powder (0.416 g, 7.58 mmol) and ammonium chloride (0.402 g, 7.58 mmol). The resulting reaction mixture was heated at 80° C. for 3 hours. TLC analysis showed no acid remaining so the mixture was passed through a cellite cartridge to remove iron. The organic solution was concentrated under vacuo to give a brown oil residue. The resulting crude mixture was treated with hydrochloric acid (1 N) and washed with ethylacetate. The aqueous layer was basified to PH=10 using sodium carbonate and extracted with ethyl acetate and washed with brine and water. The organic layer was separated, dried ($Na_2SO_4$) and concentrated. The title product was obtained as a brown solid (0.23 g, 51% yield). MS m/z: 181.16 [M+H]$^+$.

Step C:

5-((3,5-dichloropyridin-4-yl)thio)-N-(6-((2-(dimethylamino)ethyl)amino)pyridin-3-yl)-4-nitrothiophene-2-carboxamide: Prepared according to the procedure described for example 50 from 5-[(3,5-dichloro-4-pyridyl)sulfanyl]-4-nitro-thiophene-2-carboxylic acid (200 mg, 0.57 mmol) and N2-(2-(dimethylamino)ethyl)pyridine-2,5-diamine (113 mg, 0.63 mmol). The title compound was obtained as a yellow solid (9.0 mg, 3% yield). $^1$H NMR (400 MHz, $d_6$-DMSO) δ: 10.37 (1H, br), 8.99 (2H, m), 8.61 (1H, m), 8.20 (1H, m), 7.60 (1H, m), 6.53 (2H, m), 2.65 (2H, m), 2.50 (6H, m), 2.37 (2H, m). MS m/z: 513.17, 515.17 [M+H]$^+$.

Example 239

5-((3,5-dichloropyridin-4-yl)thio)-N-((5-methoxypyridin-3-yl)methyl)-4-nitrothiophene-2-carboxamide: Prepared according to the procedure described for example 44 from 5-[(3,5-dichloro-4-pyridyl)sulfanyl]-4-nitro-thiophene-2-carboxylic acid (28 mg, 0.08 mmol) and (5-methoxypyridin-3-yl)methanamine (13.8 mg, 0.1 mmol). The title compound was obtained as a solid (20 mg, 43% yield). MS m/z: 470.98, 472.98 [M+H]$^+$.

Example 240

5-((3,5-dichloropyridin-4-yl)thio)-N-(4-(3-(dimethylamino)propoxy)-3-methoxyphenyl)-4-nitrothiophene-2-carboxamide: Prepared according to the procedure described for example 70 from 5-[(3,5-dichloro-4-pyridyl)sulfanyl]-4-nitro-thiophene-2-carboxylic acid (250 mg, 0.71 mmol), 2-(7-Aza-1H-benzotriazole-1-yl)-1,1,3,3-tetramethyluronium hexafluorophosphate (HATU) (126 mg, 0.33 mmol) and 4-(3-dimethylaminopropoxy)-3-methoxy-aniline as in step B of 207 (298 mg, 0.78 mmol). The title compound was obtained as a yellow solid (50.0 mg, 13% yield). $^1$H NMR (400 MHz, $d_6$-DMSO) δ: 10.45 (1H, s), 9.32 (1H, br), 9.01 (2H, m), 8.67 (1H, s), 7.33 (1H, m), 7.20 (1H, m), 4.02 (2H, m), 3.74 (3H, s), 3.21 (2H, m), 2.83 (6H, s), 2.07 (2H, m). MS m/z: 557.30, 559.29 [M+H]$^+$.

Example 241

Step A:

2-(2-hydroxy-3-(piperidin-1-yl)propyl)isoindoline-1,3-dione: To a solution of 2-(oxiran-2-ylmethyl)isoindoline-1,3-dione (1.0 g, 4.9 mmol) in ethanol (25 mL) was added piperidine (0.46 g, 5.4 mmol). The resulting reaction mixture was heated at reflux for 1 hour. After this time, TLC analysis showed no starting material remaining so the mixture was concentrated to afford the title product as oil (1.0 g). The titled product structure was confirmed by LC/MS analysis. MS m/z: 289.21 [M+H]$^+$. The resulting hydroxylamine was dissolved in ethanol (20 mL) and to which was added hydrazine (0.86 g, 7.36 mmol). The resulting reaction mixture was stirred at ambient temperature for over night. After this time, TLC analysis showed no starting material remaining so the mixture was concentrated to afford the title product as oil (0.4 g). MS m/z: 159.2 [M+H]$^+$. The crude was used as such for the next step transformation.

Step B:

5-((3,5-dichloropyridin-4-yl)thio)-N-(2-hydroxy-3-(piperidin-1-yl)propyl)-4-nitrothiophene-2-carboxamide: Prepared according to the procedure described for example 70 from 5-((3,5-dichloropyridin-4-yl)thio)-4-nitrothiophene-2-carboxylic acid (500 mg, 1.4 mmol) and 1-amino-3-(piperidin-1-yl)propan-2-ol (270 mg, 1.7 mmol) from the above. The title compound was obtained as a solid (125.0 mg, 18% yield). $^1$H NMR (400 MHz, $d_6$-DMSO) δ: 9.10 (1H, m), 9.00 (2H, m), 8.47 (1H, s), 5.82 (1H, m), 4.03 (1H, m), 3.23 (2H, m), 3.14 (1H, m), 2.92 (2H, m), 2.85 (1H, m), 1.80 (2H, m), 1.67 (2H, m), 1.35 (1H, m). MS m/z: 491.15, 493.16 [M+H]$^+$.

Example 242

Step A:

3,5-dichloro-4-((5-(methoxycarbonyl)-3-nitrothiophen-2-yl)thio)pyridine 1-oxide: Prepared according to the procedure described for example 18 from methyl 5-chloro-4-nitrothiophene-2-carboxylate (500 mg, 2.26 mmol) and 3,5-dichloro-4-mercaptopyridine 1-oxide (441 mg, 2.26 mmol) from step A of example 18. The titled product was obtained as a solid (250 mg, 29% yield). The crude was used as such for the next step transformation.

Step B:

4-((5-carboxy-3-nitrothiophen-2-yl)thio)-3,5-dichloropyridine N-oxide: Prepared according to the procedures as described in example 50 from 3,5-dichloro-4-((5-(methoxycarbonyl)-3-nitrothiophen-2-yl)thio)pyridine 1-oxide (300 mg, 0.79 mmol) to afford the title product as a solid (250 mg, 69% yield). The crude was used as such for the next step transformation.

Step C:

3,5-dichloro-4-((5-((1-methylpiperidin-4-yl)carbamoyl)-3-nitrothiophen-2-yl)thio)pyridine 1-oxide: Prepared according to the procedure described for example 70 from 4-((5-carboxy-3-nitrothiophen-2-yl)thio)-3,5-dichloropyridine N-oxide (200 mg, 0.54 mmol) from above and 1-methylpiperidin-4-amine (64.0 mg, 0.65 mmol). The title compound was obtained as a solid (70.0 mg, 28% yield). $^1$H NMR (400 MHz, d$_6$-DMSO) δ: 8.98 (2H, m), 8.67 (1H, m), 8.51 (1H, s), 3.65 (1H, m), 2.85 (2H, m), 2.50 (3H, s), 2.24 (2H, m), 1.77 (2H, m), 1.57 (2H, m). MS m/z: 463.08, 465.08 [M+H]$^+$.

Example 243

Step A:
3,5-dichloro-2,6-dimethylpyridine-4-thiolate: Prepared according to the procedure described for example 17 from 3,4,5-trichloro-2,6-dimethylpyridine (350 mg, 1.66 mmol) and Sodium hydrosulfide hydrate (146 mg, 1.99 mmol). The titled product was obtained as a solid (300 mg, 79% yield). The solid was used as such for the next step transformation.
Step B:
Methyl 5-((3,5-dichloro-2,6-dimethylpyridin-4-yl)thio)-4-nitrothiophene-2-carboxylate: Prepared according to the procedure described for example 18 from methyl 5-chloro-4-nitrothiophene-2-carboxylate (300 mg, 1.36 mmol) and sodium 3,5-dichloro-2,6-dimethylpyridine-4-thiolate (282 mg, 1.36 mmol) from above. The titled product was obtained as a solid (380 mg, 77% yield). $^1$H NMR (400 MHz, d$_6$-DMSO) δ: 8.27 (1H, s), 3.83 (3H, s), 2.07 (3H, s), 2.05 (3H, s).
Step C:
5-((3,5-dichloro-2,6-dimethylpyridin-4-yl)thio)-4-nitrothiophene-2-carboxylic acid: Prepared according to the procedure described for example 50 from methyl 5-((3,5-dichloro-2,6-dimethylpyridin-4-yl)thio)-4-nitrothiophene-2-carboxylate from the above (350 mg, 0.89 mmol). The titled product was obtained as a solid (200 mg, 58% yield). $^1$H NMR (400 MHz, d$_6$-DMSO) δ: 8.45 (1H, s), 2.93 (6H, s).
Step D:
5-((3,5-dichloro-2,6-dimethylpyridin-4-yl)thio)-N-(1-methylpiperidin-4-yl)-4-nitrothiophene-2-carboxamide: Prepared according to the procedure described for example 70 from 5-((3,5-dichloro-2,6-dimethylpyridin-4-yl)thio)-4-nitrothiophene-2-carboxylic acid from the above (200 mg, 0.53 mmol) and 1-methylpiperidin-4-amine hydrogen chloride salt (72.0 mg, 0.63 mmol). The title compound was obtained as a solid (180.0 mg, 72% yield). $^1$H NMR (400 MHz, d$_6$-DMSO) δ: 8.63 (1H, m), 8.49 (1H, s), 3.58 (1H, m), 2.75 (2H, m), 2.65 (6H, s), 2.14 (3H, s), 1.92 (2H, m), 1.72 (2H, m), 1.49 (2H, m). MS m/z: 475.18, 477.17 [M+H]$^+$.

Example 244

5-((3,5-dichloropyridin-4-yl)thio)-N-(3-(methylsulfinyl)propyl)-4-nitrothiophene-2-carboxamide: Prepared according to the procedure described for example 34 from 5-((3,5-dichloropyridin-4-yl)thio)-N-(3-(methylthio)propyl)-4-nitrothiophene-2-carboxamide (100 mg, 0.23 mmol) and MCPBA (198 mg, 1.15 mmol). The titled product was obtained as a white solid (72.0 mg, 69% yield). $^1$H NMR (400 MHz, d$_6$-DMSO) δ: 8.99 (2H, m), 8.93 (1H, m), 8.41 (1H, s), 3.30 (2H, m), 2.80 (1H, m), 2.64 (1H, m), 2.50 (3H, s), 1.84 (2H, m). MS m/z: 454.08, 456.08 [M+H]$^+$.

Example 245

5-((3,5-dichloropyridin-4-yl)thio)-N-(3-(methylsulfonyl)propyl)-4-nitrothiophene-2-carboxamide: Prepared according to the procedure described for example 35 from 5-((3,5-dichloropyridin-4-yl)thio)-N-(3-(methylsulfinyl)propyl)-4-nitrothiophene-2-carboxamide (60.0 mg, 0.13 mmol) and MCPBA (67.0 mg, 0.39 mmol). The titled product was obtained as a white solid (45.0 mg, 74% yield). $^1$H NMR (400 MHz, d$_6$-DMSO) δ: 8.99 (2H, m), 8.91 (1H, m), 8.41 (1H, s), 3.28 (2H, m), 3.13 (2H, m), 2.95 (3H, s), 1.90 (2H, m). MS m/z: 470.11, 472.06 [M+H]$^+$.

Example 246

5-((3,5-dichloropyridin-4-yl)thio)-N-(1-methylpiperidin-4-yl)-4-nitrothiophene-2-sulfonamide: Prepared according to the procedure described for step B of example 17 and step B of example 44 from 5-chloro-4-nitrothiophene-2-sulfonyl chloride (0.26 g, 1 mmol), 3,5-dichloropyridine-4-thiol sodium salt (0.18 g, 1.0 mmol) and 1-methylpiperidin-4-amine (0.55 g, 5.0 mmol). The title product was obtained as oil (2.0 mg, 0.4% yield). MS m/z: 482.97, 484.97 [M+H]$^+$.

Example 247

Step A:
Ethyl 4-cyano-5-(methylthio)-3-phenylthiophene-2-carboxylate: 3-oxo-3-phenylpropanenitrile (0.725 g, 5.0 mmol) was added to a suspension of potassium carbonate (1.98 g, 15.0 mmol) in N,N-dimethylformide (4.5 mL) and allowed to stir at ambient temperature. After 10 minutes, carbon disulfide (0.57 g, 7.5 mmol) was added in one portion and the resulting mixture stirred at ambient temperature for an additional 10 minutes then a solution of ethyl 2-chloroacetate (0.61 g, 5.0 mmol) in N,N-dimethylformide (5.0 mL) was added. After 1 hour, a solution of iodomethane (0.78 g, 5.0 mmol) in N,N-dimethylformide (2 mL) was added in a dropwise fashion then, after 30 minutes, the mixture was poured onto water and the resulting mixture was stirred for 16 hours to afford a suspension of the title product. The resulting precipitate was collected by filtration, washed with water (10 mL) and dried in vacuo overnight. The title product was obtained as a white solid (0.86 g, 56% yield). MS m/z: 326.89, 328.89 [M+Na]$^+$.
Step B:
Ethyl 4-cyano-5-(methylsulfonyl)-3-phenylthiophene-2-carboxylate: Prepared according to the procedure described for step B of example 22 from Ethyl 4-cyano-5-(methylthio)-3-phenylthiophene-2-carboxylate (0.3 g, 1 mmol) from the above. The title compound was obtained as a white solid (0.3 g, 89% yield). MS m/z: 336.05 [M+H]$^+$.
Step C:
Ethyl 4-cyano-5-((3,5-dichloropyridin-4-yl)thio)-3-phenylthiophene-2-carboxylate: Prepared according to the procedure described for step C of example 18 from Ethyl 4-cyano-5-(methylsulfonyl)-3-phenylthiophene-2-carboxylate (0.3 g, 0.89 mmol) from above and 3,5-dichloropyridine-4-thiol sodium salt (0.18 g, 1.0 mmol) at 90° C. for over night. The title product was obtained as a white solid. The crude product was used as such for the next step transformation. MS m/z: 434.98, 436.98 [M+H]$^+$.
Step D:
4-cyano-5-((3,5-dichloropyridin-4-yl)thio)-3-phenylthiophene-2-carboxylic acid: Prepared according to the procedure described for step A of example 44 from Ethyl 4-cyano-5-((3,5-dichloropyridin-4-yl)thio)-3-phenylthiophene-2-carboxylate (1 mmol) from above at 60° C. for 2 hours. The title product was obtained as a white solid. The crude product was used as such for the next step transformation. MS m/z: 406.95, 408.94 [M+H]$^+$.
Step E:
4-cyano-5-((3,5-dichloropyridin-4-yl)thio)-N-(1-methylpiperidin-4-yl)-3-phenylthiophene-2-carboxamide: Prepared according to the procedure described for step A of example 44 from 4-cyano-5-((3,5-dichloropyridin-4-yl) thio)-3-phenylthiophene-2-carboxylic acid from above and 1-methylpiperidin-4-amine (0.11 g, 1.0 mmol). The title product was obtained as a white solid (29.5 mg, 6.0% yield). MS m/z: 503.04, 505.04 [M+H]+.

Example 248

Step A:
3-oxo-3,4-dihydro-2H-benzo[b][1,4]oxazine-6-sulfonyl chloride: To a ice cold solution of chlorosulfonic acid (4.4 mL, 66.9 mmol), was added the benzothiazinone (11 g, 74.8 mmol) portion-wise. The dark blue solution was warmed to ambient temperature over 1 h, then heated at 45° C. for 2 hours. After cooling, addition of the solution to ice-water resulted in the formation of a white precipitate. The solid was filtered, washed with water/hexane and dried affording the title compound as a white solid (11 g, 60% yield). $^1$H NMR (400 MHz, d$_6$-DMSO) δ: 10.74 (1H, s), 7.23 (2H, s), 7.15 (2H, m), 6.87 (1H, dd). MS m/z: 247.22 [M+H]+.

Step B:
6-mercapto-2H-benzo[b][1,4]oxazin-3(4H)-one: To a solution of 3-oxo-3,4-dihydro-2H-benzo[b][1,4]oxazine-6-sulfonyl chloride (5.8 g, 20.2 mmol), was added the hydrogen chloride in 1,4-dioxane (30 mL) followed by tin powder (12 g, 10.1 mmol). The resulting mixture was heated under reflux for 2 hours. After this time, the solvent of the reaction mixture was removed under vacuum to give the crude residue. The resulting residue was treated with ethyl acetate and washed with brine and water. The organic layer was separated, dried (Na$_2$SO$_4$) and concentrated. The crude material was purified by silica gel chromatography using a 60:40 mixture of hexane and ethyl acetate as eluent to afford the title product as a white solid (0.59 g, 16% yield). $^1$H NMR (400 MHz, d$_6$-DMSO) δ: 10.82 (1H, s), 6.86 (2H, m), 6.81 (1H, m), 5.40 (1H, s), 4.53 (2H, s).

Step C:
Methyl 4-nitro-5-((2-oxo-2,3-dihydro-1H-benzo[b][1,4]oxazin-7-yl)thio)thiophene-2-carboxylate: Prepared according to the procedure described for step A of example 18 from 6-mercapto-2H-benzo[b][1,4]oxazin-3(4H)-one (532 mg, 2.94 mmol) and methyl 5-chloro-4-nitro-thiophene-2-carboxylate (590 mg, 2.94 mmol). The title compound was obtained as a white solid (520 mg, 48% yield). The solid was used as such for the next step transformation.

Step D:
4-nitro-5-((2-oxo-2,3-dihydro-1H-benzo[b][1,4]oxazin-7-yl)thio)thiophene-2-carboxylic acid: Prepared according to the procedure described for step A of example 44 from Methyl 4-nitro-5-((2-oxo-2,3-dihydro-1H-benzo[b][1,4]oxazin-7-yl)thio)thiophene-2-carboxylate (515 mg, 1.4 mmol). The title compound was obtained as a white solid (480 mg, 97% yield). The solid was used as such for the next step transformation.

Step E:
N-(3-cyclopropyl-1H-pyrazol-5-yl)-4-nitro-5-((3-oxo-3,4-dihydro-2H-benzo[b][1,4]oxazin-6-yl)thio)thiophene-2-carboxamide: Prepared according to the procedure described for example 70 from 4-nitro-5-((2-oxo-2,3-dihydro-1H-benzo[b][1,4]oxazin-7-yl)thio)thiophene-2-carboxylic acid (150 mg, 0.4 mmol) from above and 3-cyclopropyl-1H-pyrazol-5-amine (59 mg, 0.48 mmol). The title compound was obtained as a solid (5.0 mg, 3% yield). $^1$H NMR (400 MHz, d$_6$-DMSO) δ: 12.24 (1H, m), 11.12 (1H, m), 11.00 (1H, m), 8.70 (1H, s), 7.36 (1H, m), 7.22 (2H, m), 6.16 (1H, s), 5.31 (2H, s), 2.03 (1H, m), 1.86 (1H, m), 0.91 (2H, m), 0.83 (1H, m), 0.65 (2H, m). MS m/z: 458.26 [M+H]+.

Example 249

5-((2,4-dichlorophenyl)thio)-4-nitro-N-(3-(piperidin-1-yl)propyl)thiophene-2-carboxamide: Prepared according to the procedure described for example 81 from 5-(2,6-dichlorophenoxy)-4-nitrothiophene-2-carboxylic acid (400 mg, 1.14 mmol) and 3-(piperidin-1-yl)propan-1-amine (195 mg, 1.37 mmol). The title compound was obtained as a solid (150.0 mg, 26% yield). $^1$H NMR (400 MHz, d$_6$-DMSO) δ: 8.77 (1H, m), 8.36 (2H, s), 8.05 (1H, s), 7.99 (1H, m), 7.70 (1H, m), 3.18 (2H, m), 2.28 (3H, m), 2.22 (3H, m), 1.62 (2H, m), 1.47 (4H, m), 1.37 (2H, m). MS m/z: 474.23, 476.21 [M+H]+.

Example 250

Step A:
7-hydroxy-2H-benzo[b][1,4]oxazin-3(4H)-one: To a solution of 4-aminobenzene-1,3-diol (2.5 g, 20 mmol) in tetrahydrofuran (30 mL), sodium bicarbonate (2.52 g, 30 mmol) was added and stirred for 10 minutes. Then 2-chloroacetyl chloride (1.6 mL, 20 mmol) was added to the above mixture. The resulting reaction mixture was stirred at ambient temperature for 18 hours. A precipitate formed and removed by filtration. The filtrate was concentrated to give the oil residue. The resulting residue was treated with 10% NaOH aqueous solution for 30 minutes. The aqueous layer was acidified with 1N hydrogen chloric acid and extracted with ethyl acetate, washed with brine and water. The organic layer was separated, dried (Na$_2$SO$_4$) and concentrated. The crude material was purified by silica gel chromatography using a 90:10 mixture of hexane and ethyl acetate as eluent to afford the title product as a white solid (1.4 g, 42% yield). $^1$H NMR (400 MHz, d$_6$-DMSO) δ: 10.42 (1H, s), 9.23 (1H, s), 6.69 (1H, m), 6.35 (2H, m), 4.47 (2H, s). MS m/z: 164.01 [M+H]+.

Step B:
Methyl 4-nitro-5-((3-oxo-3,4-dihydro-2H-benzo[b][1,4]oxazin-7-yl)oxy)thiophene-2-carboxylate: Prepared according to the procedure described for step A of example 18 from 7-hydroxy-2H-benzo[b][1,4]oxazin-3(4H)-one (826 mg, 5.0 mmol) and methyl 5-chloro-4-nitro-thiophene-2-carboxylate (1.1 g, 5.0 mmol). The title compound was obtained as a white solid (400 mg, 23% yield). $^1$H NMR (400 MHz, d$_6$-DMSO) δ: 10.92 (1H, S), 8.04 (1H, S), 7.22 (1H, M), 7.10 (2H, S), 7.03 (1H, M), 4.66 (2H, S), 3.80 (3H, S). MS m/z: 349.20 [M+H]+.

Example 251

Methyl 5-(benzo[d]thiazol-2-ylthio)-4-nitrothiophene-2-carboxylate: Prepared according to the procedure described for example 43 from methyl 5-chloro-4-nitro-thiophene-2-carboxylate (330 mg, 1.5 mmol) and 1,3-benzothiazole-6-thiol (250 mg, 1.5 mmol). The title compound was obtained as a yellow solid (275 mg, 51% yield). MS m/z: 353.00 [M+H]+.

Example 252

Step A:
5-(1,3-benzothiazol-2-ylsulfanyl)-4-nitro-thiophene-2-carboxylic acid was prepared according to the procedure described for step A of example 44 from methyl 5-(1,3-benzothiazol-2-ylsulfanyl)-4-nitro-thiophene-2-carboxylate of example 255 (250 mg, 0.71 mmol). The titled compound was obtained as a yellow solid. (102 mg, 43% yield). The solid was used as such for the next step transformation.

Step B:
5-(benzo[d]thiazol-2-ylthio)-N-benzyl-4-nitrothiophene-2-carboxamide: Prepared according to the procedure described for example 44 from 5-(1,3-benzothiazol-2-ylsulfanyl)-4-nitro-thiophene-2-carboxylic acid (34 mg, 0.1 mmol) and benzylamine (13.0 mg, 0.12 mmol). The title compound was obtained as a solid (10 mg, 23% yield). MS m/z: 428.08 [M+H]$^+$.

Example 253

5-(benzo[d]thiazol-2-ylthio)-N-(1-isopropylpiperidin-4-yl)-4-nitrothiophene-2-carboxamide: Prepared according to the procedure described for example 44 from 5-(1,3-benzothiazol-2-ylsulfanyl)-4-nitro-thiophene-2-carboxylic acid as in step A of example 256 (34 mg, 0.1 mmol) and 1-isopropylpiperidin-4-amine (17.0 mg, 0.12 mmol). The title compound was obtained as a solid (6.5 mg, 15% yield). MS m/z: 463.09, 465.09 [M+H]$^+$.

Example 254

5-(benzo[d]thiazol-2-ylthio)-N-(3-(dimethylamino)-1-phenylpropyl)-4-nitrothiophene-2-carboxamide: Prepared according to the procedure described for example 44 from 5-(1,3-benzothiazol-2-ylsulfanyl)-4-nitro-thiophene-2-carboxylic acid as in step A of example 256 (34 mg, 0.1 mmol) and N',N'-dimethyl-1-phenyl-propane-1,3-diamine (21.3 mg, 0.12 mmol). The title compound was obtained as a solid (6.5 mg, 13% yield). MS m/z: 499.08, 501.07 [M+H]$^+$.

Example 255

Step A:
Methyl 5-((3,5-difluoropyridin-4-yl)thio)-4-nitrothiophene-2-carboxylate: Prepared according to the procedure described for example 17 from 3,4,5-trifluoropyridine (500 mg, 3.8 mmol) and Sodium hydrosulfide hydrate (300 mg, 3.8 mmol) to give titled product (560 mg, 87% yield). $^1$H NMR (400 MHz, d$_6$-DMSO) δ: 7.68 (2H, s). MS m/z: 148.07 [M+H]$^+$.
Step B:
Methyl 5-((3,5-difluoropyridin-4-yl)thio)-4-nitrothiophene-2-carboxylate: Prepared according to the procedure described for example 18, sodium 3,5-difluoropyridine-4-thiolate (529 mg, 3.6 mmol) reacted with methyl 5-chloro-4-nitro-thiophene-2-carboxylate (800 mg, 3.6 mmol) to afford the titled product (800 mg, 67% yield). $^1$H NMR (400 MHz, d$_6$-DMSO) δ: 8.91 (2H, s), 8.18 (1H, s), 3.85 (3H, s). MS m/z: 333.04 [M+H]$^+$.

Example 256

Step A:
5-((3,5-difluoropyridin-4-yl)thio)-4-nitrothiophene-2-carboxylic acid: Prepared according to the procedure described for step A of example 50 from methyl 5-((3,5-difluoropyridin-4-yl)thio)-4-nitrothiophene-2-carboxylate (750 mg, 2.25 mmol) from example 255. The titled product was obtained as a white solid (700 mg, 98% yield). $^1$H NMR (400 MHz, d$_6$-DMSO) δ: 9.00 (2H, s), 8.08 (1H, s). MS m/z: 317.05 [M+H]$^+$.
Step B:
5-((3,5-difluoropyridin-4-yl)thio)-N-(1-methylpiperidin-4-yl)-4-nitrothiophene-2-carboxamide: Prepared according to the procedure described for example 70 from 5-((3,5-difluoropyridin-4-yl)thio)-4-nitrothiophene-2-carboxylic acid (200 mg, 0.63 mmol) from above and 1-methylpiperidin-4-amine (86.0 mg, 0.76 mmol). The title compound was obtained as a solid (50.0 mg, 19% yield). $^1$H NMR (400 MHz, d$_6$-DMSO) δ: 8.89 (2H, s), 8.64 (1H, m), 8.48 (1H, s), 3.57 (1H, m), 2.72 (2H, m), 2.14 (3H, s), 1.91 (2H, m), 1.73 (2H, m), 1.52 (2H, m). MS m/z: 415.13 [M+H]$^+$.

Example 257

5-((3,5-difluoropyridin-4-yl)thio)-N-(4-(3-(dimethylamino)propoxy)phenyl)-4-nitrothiophene-2-carboxamide: Prepared according to the procedure described for example 44 from 5-((3,5-difluoropyridin-4-yl)thio)-4-nitrothiophene-2-carboxylic acid (25 mg, 0.79 mmol) and 4-(3-(dimethylamino)propoxy)aniline (26.7 mg, 0.79 mmol). The title compound was obtained as a solid (12 mg, 15%). MS m/z: 495.10, [M+H]$^+$.

Example 258

Methyl 5-((3,5-dichloropyridin-4-yl)oxy)-4-nitrothiophene-2-carboxylate: Prepared according to the procedure described for step A of example 18 from 3,5-dichloropyridin-4-ol (370 mg, 2.26 mmol) and methyl 5-chloro-4-nitro-thiophene-2-carboxylate (500 mg, 2.26 mmol). The title compound was obtained as a solid (510 mg, 65% yield). $^1$H NMR (400 MHz, d$_6$-DMSO) δ: 8.65 (2H, s), 8.26 (1H, s), 3.93 (3H, s). MS m/z: 348.00, 350.99 [M+H]$^+$.

Example 259

Step A:
5-((3,5-dichloropyridin-4-yl)oxy)-4-nitrothiophene-2-carboxylic acid: Prepared according to the procedure described for step A of example 50 from methyl 5-((3,5-difluoropyridin-4-yl)thio)-4-nitrothiophene-2-carboxylate (100 mg, 0.29 mmol) from example 258. The titled product was obtained as a white solid (70 mg, 73% yield). $^1$H NMR (400 MHz, d$_6$-DMSO) δ: 8.64 (2H, s), 8.11 (1H, s). MS m/z: 335.01, 336.98 [M+H]$^+$.
Step B:
5-((3,5-dichloropyridin-4-yl)oxy)-N-(1-methylpiperidin-4-yl)-4-nitrothiophene-2-carboxamide: Prepared according to the procedure described for example 70 from 5-((3,5-dichloropyridin-4-yl)oxy)-4-nitrothiophene-2-carboxylic acid (70 mg, 0.21 mmol) from above and 1-methylpiperidin-4-amine (28.5 mg, 0.25 mmol). The title compound was obtained as a solid (35.0 mg, 39% yield). $^1$H NMR (400 MHz, d$_6$-DMSO) δ: 9.03 (1H, m), 8.62 (2H, m), 8.57 (1H, s), 3.88 (1H, m), 3.12 (2H, m), 2.60 (2H, m), 2.50 (3H, s), 1.93 (2H, m), 1.77 (2H, m). MS m/z: 431.05, 433.14 [M+H]$^+$.

Example 260

5-((3,5-dichloropyridin-4-yl)oxy)-N-(1-isopropylpiperidin-4-yl)-4-nitrothiophene-2-carboxamide: Prepared according to the procedure described for example 44 from 5-((3,5-dichloropyridin-4-yl)oxy)-4-nitrothiophene-2-carboxylic acid (10 mg, 0.03 mmol) from above and 1-isopropylpiperidin-4-amine (17.4 mg, 0.1 mmol). The title compound was obtained as a solid (1.0 mg, 7% yield). MS m/z: 459.01, 461.01 [M+H]$^+$.

Example 261

Step A:
Methyl 5-(2,6-dichlorophenoxy)-4-nitrothiophene-2-carboxylate: Prepared according to the procedure described for step A of example 18 from 2,6-dichloro-phenol (368 mg, 2.26 mmol) and methyl 5-chloro-4-nitro-thiophene-2-carboxylate (500 mg, 2.26 mmol). The title compound was obtained as a white solid (500 mg, 65% yield). $^1$H NMR (400 MHz, d$_6$-DMSO) δ: 8.12 (1H, m), 7.80 (2H, m), 7.58 (1H, m), 3.80 (3H, s). MS m/z: 365.07, 367.00 [M+H]$^+$.

Step B:

5-(2,6-dichlorophenoxy)-4-nitrothiophene-2-carboxylic acid: Prepared according to the procedure described for step A of example 50 from methyl 5-(2,6-dichlorophenoxy)-4-nitrothiophene-2-carboxylate (100 mg, 0.27 mmol). The title compound was obtained as a white solid (75 mg, 96% yield). $^1$H NMR (400 MHz, d$_6$-DMSO) δ: 8.01 (1H, s), 7.82 (2H, m), 7.57 (1H, m). MS m/z: 288.01, 290.04 [M+H]$^+$. Step C: 5-(2,6-dichlorophenoxy)-N-(1-methylpiperidin-4-yl)-4-nitrothiophene-2-carboxamide: Prepared according to the procedure described for example 70 from 5-(2,6-dichlorophenoxy)-4-nitrothiophene-2-carboxylic acid (70 mg, 0.27 mmol) from above and 1-methylpiperidin-4-amine (28.0 mg, 0.30 mmol). The title compound was obtained as a solid (30.0 mg, 26% yield). $^1$H NMR (400 MHz, d$_6$-DMSO) δ: 8.68 (1H, m), 8.39 (1H, s), 7.78 (2H, m), 7.56 (1H, m), 3.66 (1H, m), 2.85 (2H, m), 2.24 (3H, s), 1.78 (2H, m), 1.57 (2H, m), 1.23 (2H, m). MS m/z: 430.12, 432.09 [M+H]$^+$.

Example 262

5-((3,5-dichloropyridin-4-yl)thio)-N-(1-ethylpiperidin-4-yl)-4-nitrothiophene-2-carboxamide: Prepared according to the procedure described for example 199 from 5-((3,5-dichloropyridin-4-yl)thio)-4-nitro-N-(piperidin-4-yl)thiophene-2-carboxamide (0.2 g, 0.46 mmol) and acetaldehyde (81.0 mg, 1.38 mmol). The title compound was obtained as a solid (8.0 mg, 4% yield). $^1$H NMR (400 MHz, d$_6$-DMSO) δ:8.98 (2H, m), 8.73 (1H, m), 8.52 (1H, s), 4.28 (1H, m), 3.67 (2H, m), 3.17 (1H, m), 2.97 (2H, m), 2.16 (2H, m), 1.79 (2H, m), 1.58 (2H, m), 1.03 (3H, m). MS m/z: 461.08, 463.09 [M+H]$^+$.

Example 263

5-((3,5-dichloropyridin-4-yl)thio)-N-(3-isopropyl-1H-pyrazol-5-yl)-4-nitrothiophene-2-carboxamide: Prepared according to the procedure described for example 44 from 5-[(3,5-dichloro-4-pyridyl)sulfanyl]-4-nitro-thiophene-2-carboxylic acid (35 mg, 0.1 mmol) and 3-isopropyl-1H-pyrazol-5-amine (12.5 mg, 0.1 mmol). The title compound was obtained as a solid (7.1 mg, 16% yield). MS m/z: 458.00, 460.00 [M+H]$^+$.

Example 264

5-((3,5-dichloropyridin-4-yl)thio)-N-(4-(methylthio)benzyl)-4-nitrothiophene-2-carboxamide: Prepared according to the procedure described for example 70 from 5-[(3,5-dichloro-4-pyridyl)sulfanyl]-4-nitro-thiophene-2-carbonyl chloride (200 mg, 0.54 mmol) from above and 4-methylthiobenzylamine (99.0 mg, 0.65 mmol). The title compound was obtained as a solid (100 mg, 19% yield). $^1$H NMR (400 MHz, d$_6$-DMSO) δ: 9.35 (1H, m), 8.98 (2H, s), 8.46 (1H, s), 7.22 (4H, m), 4.35 (2H, m), 2.34 (3H, s). MS m/z: 484.11, 486.14 [M+H]$^+$.

Example 265

Methyl 5-((5-chloro-6-fluoro-1H-benzo[d]imidazol-2-yl)thio)-4-nitrothiophene-2-carboxylate: Prepared according to the procedure described for example 18 from 1-(5-Chloro-4-nitro-2-thienyl)ethanone (330 mg, 1.5 mmol) and 5-chloro-6-fluoro-1H-benzo[d]imidazole-2-thiol (303 mg, 1.5 mmol). The title compound was obtained as a yellow solid (570 mg, 98% yield) MS m/z: 387.85, 389.90 [M+H]$^+$.

Example 266

Methyl 5-((5,7-dimethyl-[1,2,4]triazolo[1,5-a]pyrimidin-2-yl)thio)-4-nitrothiophene-2-carboxylate: Prepared according to the procedure described for example 18 from 1-(5-Chloro-4-nitro-2-thienyl)ethanone (221 mg, 1.0 mmol) and 5,7-dimethyl-[1,2,4]triazolo[1,5-a]pyrimidine-2-thiol (180 mg, 1.0 mmol). The title compound was obtained as a solid (300 mg, 82% yield). MS m/z: 366.02 [M+H]$^+$.

Example 267

Step A:

Methyl 5-((2,4-difluorophenyl)thio)-4-nitrothiophene-2-carboxylate: Prepared according to the procedure described for step A of example 18 from 2,4-difluoro-phenol (0.5 mL, 4.52 mmol) and methyl 5-chloro-4-nitro-thiophene-2-carboxylate (1.0 g, 4.52 mmol). The title compound was obtained as a white solid (1.1 g, 74% yield) $^1$H NMR (400 MHz, d$_6$-DMSO) δ: 8.14 (1H, s), 7.98 (1H, m), 7.69 (1H, m), 7.43 (1H, m), 3.78 (3H, s). The crude was used as such for further transformation.

Step B:

5-((2,4-difluorophenyl)thio)-4-nitrothiophene-2-carboxylic acid: Prepared according to the procedure described for step A of example 44 from methyl 5-(2,4-difluorophenoxy)-4-nitrothiophene-2-carboxylate (0.8 g, 2.92 mmol). The title compound was obtained as a white solid (0.605 g, 65% yield). The crude was used for further transformation without further purification. $^1$H NMR (400 MHz, d$_6$-DMSO) δ: 8.05 (1H, s), 7.98 (1H, m), 7.69 (1H, m), 7.41 (1H, m).

Step C:

5-((2,4-difluorophenyl)thio)-4-nitro-N-(3-(piperidin-1-yl)propyl)thiophene-2-carboxamide: Prepared according to the procedure described for example 70 from 5-(2,4-difluorophenoxy)-4-nitrothiophene-2-carboxylic acid (200 mg, 0.57 mmol) from above and 3-(piperidin-1-yl)propan-1-amine (108 mg, 0.68 mmol). The title compound was obtained as a solid (130.0 mg, 52% yield). $^1$H NMR (400 MHz, d$_6$-DMSO) δ: 8.77 (1H, m), 8.35 (2H, s), 7.95 (1H, m), 7.68 (1H, m), 7.40 (1H, m), 3.19 (2H, m), 2.27 (3H, m), 2.21 (3H, m), 1.60 (2H, m), 1.46 (4H, m), 1.36 (2H, m). MS m/z: 442.29, 444.24 [M+H]$^+$.

Example 268

Step A:

tert-butyl (3-oxo-3-(pyrrolidin-1-yl)propyl)carbamate: 2-(7-Aza-1H-benzotriazole-1-yl)-1,1,3,3-tetramethyluronium hexafluorophosphate (5.9 g, 15.4 mmol), pyrrolidine (3.2 g, 16.8 mmol) and diisopropylethylamine (5.4 mL, 42.2 mmol) was added to a suspension of 3-((tert-butoxycarbonyl)amino)propanoic acid (1.0 g, 14.0 mmol) in dichloromethane (20 mL) and the resulting mixture was stirred at ambient temperature for 6 hours. TLC analysis showed no acid remaining so the mixture was diluted with dichloromethane and washed with water and brine. The organic layer was separated, dried (Na$_2$SO$_4$), filtered and the solvent was removed to afford a solid. The crude material was purified by silica gel chromatography using a 70:30 mixture of hexane and ethyl acetate as eluent to afford the title product as a solid (3.0 g, 88% yield). MS m/z: 243.26 [M+H]$^+$.

Step B:
3-amino-1-(pyrrolidin-1-yl)propan-1-one: Prepared according to the procedure described for step B of example 197 from tert-butyl (3-oxo-3-(pyrrolidin-1-yl)propyl)carbamate (2.5 g, 10.33 mmol). The title compound was obtained as a solid (1.2 g). MS m/z: 143.13 [M+H]$^+$. The solid was used as such for next step transformation.
Step C:
5-((3,5-dichloropyridin-4-yl)thio)-4-nitro-N-(3-oxo-3-(pyrrolidin-1-yl)propyl)thiophene-2-carboxamide: Prepared according to the procedure described for example 70 from 5-((3,5-dichloropyridin-4-yl)thio)-4-nitrothiophene-2-carboxylic acid (500 mg, 1.4 mmol) and 3-amino-1-(pyrrolidin-1-yl)propan-1-one (240 mg, 1.7 mmol). The title compound was obtained as a solid (22.0 mg, 3% yield). $^1$H NMR (400 MHz, d$_6$-DMSO) δ: 8.99 (2H, m), 8.92 (1H, m), 8.43 (1H, s), 3.40 (2H, m), 3.34 (2H, m), 3.26 (2H, m), 2.47 (2H, m), 1.84 (2H, m), 1.73 (2H, m). MS m/z: 475.10, 477.11 [M+H]$^+$.

Example 269

Step A:
Methyl 5-((2,6-dichlorophenyl)thio)-4-nitrothiophene-2-carboxylate: Prepared according to the procedure described for step A of example 18 from methyl 5-chloro-4-nitrothiophene-2-carboxylate (5 g, 22.7 mmol) and 2,6-dichlorothiophenol (4.4 g, 24.8 mmol), The titled product was obtained as an off-white solid (5.5 g, 67% yield). $^1$H NMR (400 MHz, d$_6$-DMSO) δ: 8.17 (1H, s), 7.83 (2H, m), 7.62 (1H, m), 3.77 (3H, s). MS m/z: 363.92, 365.93 [M+H]$^+$.
Step B:
5-((2,6-dichlorophenyl)thio)-4-nitrothiophene-2-carboxylic acid: Prepared according to the procedure described for step A of example 50 from methyl 5-((2,6-dichlorophenyl)thio)-4-nitrothiophene-2-carboxylate (0.2 g, 0.95 mmol). The titled product was obtained as a white solid (0.17 g, 59% yield). MS m/z: 303.88, 305.85 [M+H]$^+$.
Step C:
5-((2,6-dichlorophenyl)thio)-N-(1-methylpiperidin-4-yl)-4-nitrothiophene-2-carboxamide: Prepared according to the procedure described for example 70 from 4-((5-carboxy-3-nitrothiophen-2-yl)thio)-3,5-dichloropyridine N-oxide (2.0 g, 5.7 mmol) from above and 1-methylpiperidin-4-amine (0.78 g, 6.8 mmol). The title compound was obtained as a solid (1.9 g, 75% yield). $^1$H NMR (400 MHz, d$_6$-DMSO) δ: 8.60 (1H, m), 8.47 (1H, m), 7.82 (2H, m), 7.72 (1H, m), 3.57 (1H, m), 2.72 (2H, m), 2.14 (3H, s), 1.91 (2H, m), 1.70 (2H, m), 1.54 (2H, m). MS m/z: 446.14, 448.12 [M+H]$^+$.

Example 270

Step A:
5-chloro-4-nitrothiophene-2-carbonyl azide: oxalyl chloride (460 mg, 3.62 mmol) followed by N,N-dimethylformide (0.05 mL) was added to a solution of 5-chloro-4-nitrothiophene-2-carboxylic acid (1.0 g, 14.0 mmol) in dichloromethane (20 mL) under nitrogen atmosphere and the resulting mixture was stirred at ambient temperature for 4 hours. TLC analysis showed no acid remaining so the mixture was allowed to be concentrated in vacuo. The resulting acid chloride was dissolved in dry tetrahydrofuran (10 mL). Sodium azide (190 mg, 2.89 mmol) was added to the above solution. The resulting mixture was stirred at ambient temperature for 10 hours. After this time, TLC analysis showed no acid chloride remaining so the mixture was diluted with ethyl acetate and washed with water and brine. The organic layer was separated, dried (Na$_2$SO$_4$), filtered and the solvent was removed to afford the title product as a brown solid (400 mg, 59% yield). $^1$H NMR (400 MHz, d$_6$-DMSO) δ: 8.23 (2H, s).
Step B:
1-(5-chloro-4-nitrothiophen-2-yl)-3-(1-methylpiperidin-4-yl)urea: 5-chloro-4-nitrothiophene-2-carbonyl azide (400 mg, 1.23 mmol) from above was dissolved in toluene (10 mL) and the resulting solution was refluxed for 2 hours. After this time, the reaction mixture was cooled to ambient temperature. 1-methylpiperidin-4-amine (155 mg, 1.36 mmol) was added drop-wise to the above solution. The resulting mixture was stirred at ambient temperature for 9 hours. After this time, TLC analysis showed no intermediate isocyanate remaining so the mixture was diluted with ethyl acetate and washed with water and brine. The organic layer was dried (Na$_2$SO$_4$), filtered and the solvent was removed to give the crude residue. The crude material was purified by silica gel chromatography using a 95:5 mixture of dichloromethane and methanol as eluent to afford the title product as a brown solid (200 mg, 51% yield). $^1$H NMR (400 MHz, d$_6$-DMSO) δ: 10.03 (1H, br), 6.97 (1H, m), 6.86 (1H, s), 3.51 (1H, m), 2.88 (2H, m), 2.77 (1H, m) 2.32 (4H, m), 1.55 (2H, m), 1.23 (2H, m).
Step C:
1-(5-((3,5-dichloropyridin-4-yl)thio)-4-nitrothiophen-2-yl)-3-(1-methylpiperidin-4-yl)urea: Prepared according to the procedure described for step A of example 18 from 1-(5-chloro-4-nitrothiophen-2-yl)-3-(1-methylpiperidin-4-yl) urea (100 mg, 0.31 mmol) and 3,5-dichloropyridine-4-thiol sodium salt (62 mg, 0.35 mmol). The title compound was obtained as a white solid (120 mg, 85% yield). $^1$H NMR (400 MHz, d$_6$-DMSO) δ: 10.01 (1H, m), 8.92 (2H, m), 6.91 (1H, m), 3.43 (2H, m), 2.87 (2H, m), 2.33 (3H, m), 1.91 (1H, m), 1.74 (2H, m), 1.46 (2H, m). MS m/z: 459.94, 461.94 [M+H]$^+$.

Example 271

1-(5-(2,4-dichlorophenoxy)-4-nitrothiophen-2-yl)ethanone: Potassium t-butoxide (0.30 g, 2.67 mmol) was suspended in anhydrous tetrahydrofuran (25 mL), 2,4-dichlorophenol (0.40 g, 2.43 mmol) was added and the resulting mixture was stirred at ambient temperature under nitrogen for 30 minutes. After this time, 1-(5-chloro-4-nitro-2-thienyl)ethanone (0.5 g, 2.43 mmol) was added, the resulting mixture was stirred at ambient temperature for 45 minutes, then it was poured into water (100 mL) and stirred at ambient temperature overnight. The resulting solid was collected by filtration, washed with water (2×10 mL) and dried in air. The crude product was dissolved in acetonitrile (7 mL), the resulting solution was evaporated to near dryness and the residue was triturated with diethyl ether (2 mL). The resulting solid was collected by filtration and dried in vacuo at 40° C. overnight to afford the title product as a solid (0.45 g, 55% yield). $^1$H NMR (300 MHz, d$^6$-acetone) δ: 8.15 (1H, s), 7.68 (1H, d), 7.51 (2H, m), 2.45 (3H, s).

Example 272

1-(5-((4-chloro-2,3,5,6-tetrafluorophenyl)thio)-4-nitrothiophen-2-yl)ethanone: Prepared by a similar procedure to that described for example 1 from the 1-(5-chloro-4-nitro-2-thienyl)ethanone (205 mg, 1.0 mmol) and 2,3,5,6-tetrafluoro-4-chloro-benzenethiol (216 mg, 0.98 mmol) to afford the title product as a solid (220 mg, 57% yield). $^1$H NMR (400 MHz, d$_6$-DMSO) δ: 8.55 (1H, s), 3.37 (3H, s). MS m/z: 384.12, 386.12 [M+H]$^+$.

The biological activity of compounds of the invention can be determined using, e.g., the assays and screening techniques set forth in the following examples.

In these examples, full length human USP7 protein and the fusion protein Ub-PLA$_2$ were cloned, expressed and purified in the manner described in B. Nicholson et al., Protein Sci., 17(6): 1035-1043 (2008).

Example 273

USP7, Ub-PLA$_2$ assay

The purpose of this assay is to measure the inhibition of USP7 by various compounds of the invention synthesized according to the above-described methods. The stock solution of test compound was diluted to 2.55 mM in 100% (v/v) DMSO. Subsequently, the test compound was serially diluted in 100% (v/v) DMSO in two fold increments resulting in compound concentrations ranging from 2.55 mM to 199 µM. The control compound N-ethylmaleimide (NEM; Fisher Scientific) was dissolved in 100% (v/v) DMSO at a concentration of 1 M and then diluted to 510 mM in 100% (v/v) DMSO. The vehicle control was 100% (v/v) DMSO. 1.6 µL aliquots of the diluted test compound and controls were dispensed into individual wells in a black walled 96 well plate. USP7 was diluted to a concentration of 24.8 nM in assay buffer (20 mM Tris, pH 8, 2 mM CaCl2, 2 mM =-mercaptoethanol). Subsequently, 80 µL aliquots of 24.8 nM USP7 were added to the serially diluted test compound and the mixtures were incubated at room temperature for 30 minutes, protected from light. 6His (SEQ ID NO: 1)-Ub-PLA$_2$ and NBD C$_6$-HPC (Invitrogen) were mixed to concentrations of 101.6 nM and 101.6 pM respectively in assay buffer. Cleavage of 6His (SEQ ID NO: 1)-Ub-PLA$_2$ by USP7 releases PLA$_2$ that is then free to cleave NBD C$_6$-HPC thus releasing fluorescent NBD. After the 30 minute incubation of USP7 and test compound (see above), 20 µL aliquots of 101.6 nM 6His (SEQ ID NO: 1)-Ub-PLA$_2$/ 101.6 µM NBD C$_6$-HPC were added to each well and the increase in fluorescence was determined by measuring on a fluorescence plate reader with $=_{ex}$=475 nm, $=_{em}$=555 nm filters. The data were normalized within a plate relative to the control wells using the equation % inhibition= (100−(((RFU$_{compound}$−RFU$_{mean\ NEM}$) / (RFU$_{mean\ DMSO}$− RFU$_{mean\ NEM}$))×100)). The EC$_{50}$ value (the test compound concentration at which 50% of the maximal observed inhibition is established) was determined by fitting the normalized data to a standard sigmoidal dose response equation (BioAssay, CambridgeSoft).

The compounds of Examples 1-273 were tested in this assay. Example 96 to 197, 200 to 202, 205, 208, 222, 225 to 227, 229, 230, 233 to 240 and 264 exhibited EC$_{50}$ values less than or equal to 1 µM in this assay. Example 2 to 4, 6 to 10, 12, 13, 15, 17, 18, 22 to 25, 32, 35 to 37, 40, 42 to 75, 77, 79 to 83, 85 to 95, 198, 199, 203, 204, 206, 207, 209 to 221, 223, 224, 228, 231, 232, 241 to 258, 265, 268, 269, 270, 271, 272 exhibited EC$_{50}$ values greater than 1 µM and less than or equal to 10 µM in this assay. Example 1, 5, 11, 14, 16, 19 to 21, 26 to 31, 33, 34, 38, 39, 41, 76, 78, 84, 259, 260, 261, 266, 267, 272 exhibited EC$_{50}$ values greater than 10 µM in this assay.

Particularly good results have been exhibited by the following compounds: N-(3-cyclopropyl-1H-pyrazol-5-yl)-5-((3,5-dichloropyridin-4-yl)thio)-4-nitrothiophene-2-carboxamide; 5-((3,5-dichloropyridin-4-yl)thio)-N-(4-(methylsulfonyl)phenyl)-4-nitrothiophene-2-carboxamide; 5-((3,5-dichloropyridin-4-yl)thio)-N-(4-methoxyphenyl)-4-nitrothiophene-2-carboxamide; 5-((3,5-dichloropyridin-4-yl)thio)-4-nitro-N-(quinolin-3-yl)thiophene-2-carboxamide; 5-((3,5-dichloropyridin-4-yl)thio)-N-(4-(3-(dimethylamino)propoxy)phenyl)-4-nitrothiophene-2-carboxamide; and 5-((3,5-dichloropyridin-4-yl)thio)-N-(4-guanidinophenyl)-4-nitrothiophene-2-carboxamide.

Example 274

NCI-60 Human Tumor Cell Line Growth Inhibition Screen

Various human tumor cell lines representing the NCI-60 cancer screening panel were grown in RPMI 1640 medium containing 5% fetal bovine serum and 2 mM L-glutamine. For a typical screening experiment, cells were inoculated into 96 well microtiter plates in 100 µL at plating densities ranging from 5,000 to 40,000 cells/well depending on the doubling time of individual cell lines. After cell inoculation, the microtiter plates were incubated at 37° C., 5% CO$_2$, 95% air and 100% relative humidity for 24 hours prior to addition of the test compound. After 24 hours, two plates of each cell line were fixed in situ with TCA, to represent a measurement of the cell population for each cell line at the time of test compound addition (Tz). Experimental test compounds were solubilized in 100% (v/v) DMSO at 400-fold the desired final maximum test concentration and stored frozen prior to use. At the time of test compound addition, an aliquot of frozen concentrate was thawed and diluted to twice the desired final maximum test concentration with complete medium containing 50 µg/ml gentamicin. Additional four, 10-fold or ½ log serial dilutions were made to provide a total of five test compound concentrations plus control. Aliquots of 100 µl of these different test compound dilutions were added to the appropriate microtiter wells already containing 100 µl of medium, resulting in the required final test compound concentrations.

Following test compound addition, the plates were incubated for an additional 48 hours at 37° C., 5% CO$_2$, 95% air, and 100% relative humidity. For adherent cells, the assay was terminated by the addition of cold TCA. Cells were fixed in situ by the gentle addition of 50 µl of cold 50% (w/v) TCA and incubated for 60 minutes at 4° C. The supernatant was discarded, and the plates were washed five times with tap water and air dried. Sulforhodamine B (SRB) solution (100 µl) at 0.4% (w/v) in 1% acetic acid was added to each well, and plates were incubated for 10 minutes at room temperature. After staining, unbound dye was removed by washing five times with 1% acetic acid and the plates were air dried. Bound stain was subsequently solubilized with 10 mM trizma base, and the absorbance was read on an automated plate reader at a wavelength of 515 nm. For suspension cells, the methodology was the same except that the assay was terminated by fixing settled cells at the bottom of the wells by gently adding 50 µl of 80% TCA. Using the seven absorbance measurements [time zero, (Tz), control growth, (C), and test growth in the presence of test compound at the five concentration levels (Ti)], the percentage growth was calculated at each of the test compound concentrations levels. Percentage growth inhibition was calculated as: [(Ti−Tz)/(C−Tz)]×100 for concentrations for which Ti≥Tz or [(Ti−Tz)/Tz]×100 for concentrations for which Ti<Tz. Growth inhibition of 50% (GI$_{50}$) was calculated from [(Ti−Tz)/(C−Tz)]×100=50, which is the test compound concentration resulting in a 50% reduction in the net protein increase (as measured by SRB staining) in control cells during the test compound incubation.

TABLE I

Test compounds exhibit growth inhibition in the NCI-60 panel.

| Cell line | Tumor type | P5091 GI$_{50}$ (μM) | Example 3 GI$_{50}$ (μM) | Example 17 GI$_{50}$ (μM) | Example 23 GI$_{50}$ (μM) | Example 22 GI$_{50}$ (μM) |
|---|---|---|---|---|---|---|
| HL-60(TB) | Leukemia | 1.82 | 2.75 | 1.91 | 2.19 | 1.41 |
| A549/ATCC | Non-Small Cell Lung Cancer | 16.3 | 15.5 | 3.09 | 12.6 | 13.8 |
| HT29 | Colon Cancer | 2.07 | 3.80 | 1.86 | 1.78 | 2.04 |
| U251 | CNS Cancer | 2.33 | 4.79 | 1.95 | 6.31 | 12.9 |
| LOX IMVI | Melanoma | 1.84 | 1.51 | 1.51 | 1.74 | 10.0 |
| OVCAR-3 | Ovarian Cancer | 1.65 | 2.04 | 1.41 | 1.62 | 1.82 |
| CAKI-1 | Renal Cancer | 2.17 | 1.82 | 1.86 | 2.24 | 1.82 |
| PC-3 | Prostate Cancer | 1.78 | 12.0 | 2.75 | 3.98 | 3.72 |
| MCF7 | Breast Cancer | 1.94 | 2.57 | 1.91 | 1.70 | 2.04 |

Example 275

HCT-116 Cellular Cytotoxicity Assay

The purpose of this assay is to determine if any of the synthesized compounds are cytotoxic against HCT-116 cells, as measured by resazurin metabolism. Resazurin is metabolized only by living cells from a non-fluorescent molecule into Resorufin, a highly red fluorescent dye. HCT-116 (ATCC; CRL-247), a human colorectal carcinoma cell line, was maintained in HCT-116 media (Dulbecco's modification of Eagle's medium supplemented with 10% (v/v) fetal bovine serum, 2 mM L-glutamine, 100 IU/ml penicillin, 100 μg/ml streptomycin and 10 mM HEPES, pH 7.2). The cells were cultured in an incubator at 37° C. in 5% $CO_2$ and 95% humidified air. For cytotoxicity assays, the HCT-116 cells were seeded into individual wells in tissue culture treated black walled 96 well plates at a density of 2.5×10$^3$ cells/well in 90 μL of HCT-116 media and the plate was incubated overnight to allow the cells to establish and enter log phase growth. The stock solution of test compound was serially diluted in 100% (v/v) DMSO in two fold increments resulting in compound concentrations ranging from 10 mM to 78.1 μM. 10 μL aliquots of the diluted test compound, or 100% (v/v) DMSO were dispensed into individual wells in a sterile 96 well plate and mixed with 190 μL of HCT-116 media. 10 μl of the diluted compound or DMSO were dispensed into individual wells of HCT-116 cells resulting in final compound concentrations ranging from 50 μM to 391 nM. The final concentration DMSO was 0.5% (v/v) in all samples. The plates were returned to the incubator for 72 hours. Following 72 hours of test compound exposure, 10 μL of 0.2 mg/mL Resazurin (Sigma) in phosphate buffered saline was added to each well and the plate was returned to the incubator for 3-6 hours. Since living cells metabolize Resazurin, the fluorescence of the reduction product of Resazurin was measured using a microplate fluorometer with $\lambda_{ex}$=531 nm and $\lambda_{em}$=590 nm filters. Resazurin dye in medium without cells was used to determine the background, which was subtracted from the data for all experimental wells. The data were normalized to the average fluorescence of the cells treated with media+0.5% (v/v) DMSO (100% cell growth) and EC$_{50}$ values (the test compound concentration at which 50% of the maximal observed cytotoxicity is established) were determined using a standard sigmoidal dose response curve fitting algorithm (BioAssay, CambridgeSoft).

TABLE II

Cytotoxic activity of test compounds vs HCT-116 cells

| Entry | EC$_{50}$ (μM) |
|---|---|
| P005091 | 9.21 |
| Example 2 | 16.1 |
| Example 7 | 30.6 |
| Example 8 | 14.8 |
| Example 9 | 8.13 |
| Example 17 | 8.66 |
| Example 21 | 32.5 |
| Example 24 | 27.3 |
| Example 25 | 15.2 |
| Example 103 | 7.18 |
| Example 123 | 11.0 |
| Example 129 | 5.89 |
| Example 155 | 5.49 |
| Example 157 | 27.3 |
| Example 160 | 6.17 |
| Example 168 | 6.52 |
| Example 171 | 10.9 |
| Example 172 | 12.9 |
| Example 173 | 5.15 |
| Example 175 | 7.23 |
| Example 179 | 4.23 |
| Example 180 | 7.62 |
| Example 182 | 14.3 |
| Example 188 | 7.9 |
| Example 192 | 4.9 |
| Example 193 | 3.37 |
| Example 201 | 12.9 |
| Example 203 | 10.4 |
| Example 205 | 3.1 |
| Example 238 | 3.96 |
| Example 271 | 8.54 |

Example 276

HCT-116 Combination Cytotoxicity Assay

The purpose of this assay is to determine if any of the synthesized compounds exhibit synergistic cytotoxicity when combined with a genotoxic agent (exemplified by Doxorubicin, Etoposide or Chlormethine) against HCT-116 cells, as measured by resazurin metabolism. Resazurin is metabolized only by living cells from a non-fluorescent molecule into Resorufin, a highly red fluorescent dye. HCT-116 (ATCC; CRL-247), a human colorectal carcinoma cell line, were cultured as described in the cellular cytotoxicity assay. For combination cytotoxicity assays, the HCT-116 cells were seeded into individual wells in tissue culture treated black walled 96 well plates at a density of 2.5×10³ cells/well in 80 µL of HCT-116 media and the plate was incubated overnight to allow the cells to establish and enter log phase growth. To determine the dose-effect of two compounds they must be tested both individually and in combination. For the combination experiments the compounds were tested at constant ratios. Dose ranges of the test compounds were prepared in 100% (v/v) DMSO in two fold increments ranging from 19 mM-0.15 mM (P5091), 9.6 mM-75 µM (Example 168), 40 µM-313 nM (Doxorubicin), 4 mM-31.3 µM (Etoposide) or 1.6 µM-12.5 µM (Chlormethine). 10 µL aliquots of the diluted test compounds, or 100% (v/v) DMSO were dispensed into individual wells in a sterile 96 well plate and mixed with 190 µL of HCT-116 media. 10 µl of the diluted compound or DMSO were dispensed into individual wells of HCT-116 cells resulting in final compound concentrations ranging from 96 µM-750 nM (P5091), 48 µM-375 nM (Example 168), 200 nM-1.56 nM (Doxorubicin), 20 µM-156 nM (Etoposide) or 8 µM-62.5 nM (Chlormethine). The plates were returned to the incubator for 72 hours. Following 72 hours of test compound exposure, 10 µL, of 0.2 mg/mL resazurin (Sigma) in phosphate buffered saline was added to each well and the plate was returned to the incubator for 3-6 hours. Since living cells metabolize Resazurin, the fluorescence of the reduction product of Resazurin was measured using a microplate fluorometer with $\lambda_{ex}$=531 nm and $\lambda_{em}$=590 nm filters. Resazurin dye in medium without cells was used to determine the background, which was subtracted from the data for all experimental wells. The data were normalized to the average fluorescence of the cells treated with media+0.5% (v/v) DMSO (100% cell growth) and the combination index (CI) values were determined using the Chou-Talalay method dose-effect analyzer (CalcuSyn, BioSoft). CI values <1.0 indicate synergy; CI=1.0 indicate additive effects; and CI>1.0 indicate antagonism [1]. CI values for the 50%, 75 and 90% effective doses ($ED_{50}$, $ED_{75}$ and $ED_{90}$ respectively) were calculated.

As the biological data set forth above shows, the compounds of the invention demonstrated desired potency, having $EC_{50}$ values of less than 25 µM for inhibition of USP7 enzyme, and substantially less in many cases. The compounds tested generally possess activity in the range of less than 50 µM in the cancer cellular cytotoxicity assay. Furthermore, a combination of the compounds of this invention and a DNA-damaging chemotherapeutic agent were found to exhibit synergistic tumor cell killing effect in the HCT-116 cellular cytotoxicity assay.

A number of patent documents and non-patent documents are cited in the foregoing specification in order to describe the state of the art to which this invention pertains. The entire disclosure of each of the cited documents is incorporated by reference herein.

It should be noted that, as used in the preceding description and the appended claims, the singular articles "a", "an" and "the" also include the plural, unless the context clearly indicates otherwise.

While various embodiments of the present invention have been described and/or exemplified above, numerous other embodiments will be apparent to those skilled in the art upon review of the foregoing disclosure. The present invention is, therefore, not limited to the particular embodiments described and/or exemplified, but is capable of considerable variation and modification without departure from the scope of the appended claims. Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the

TABLE III

Summary of CI values

| Combination agent | P005091 CI (mean ± SD) | | | Example 168 CI (mean ± SD) | | |
|---|---|---|---|---|---|---|
| | $ED_{50}$ | $ED_{75}$ | $ED_{90}$ | $ED_{50}$ | $ED_{75}$ | $ED_{90}$ |
| Doxorubicin | 0.68 ± 0.15 | 0.73 ± 0.08 | 0.81 ± 0.02 | 0.69 ± 0.11 | 0.73 ± 0.09 | 0.81 ± 0.11 |
| Etoposide | 0.52 ± 0.09 | 0.54 ± 0.04 | 0.63 ± 0.01 | 0.55 ± 0.13 | 0.54 ± 0.10 | 0.59 ± 0.14 |
| Chlormethine | 0.61 ± 0.09 | 0.67 ± 0.07 | 0.77 ± 0.05 | 0.66 ± 0.13 | 0.70 ± 0.10 | 0.78 ± 0.13 |

Example 277

In vivo Efficacy of P5091

Severe combined immunodeficient mice inoculated subcutaneously with human multiple myeloma tumor cells were treated intravenously twice a week for three weeks with 10 mg/kg P5091. Data from this study revealed that P5091 significantly inhibited human plasmacytoma growth in SCID mice. Furthermore, P5091 significantly enhanced survival in the same model. See D. Chauhan et al., Abstract No. 610 (Deubiquitylating Enzyme USP-7, a Novel Therapeutic Target in Multiple Myeloma), 51st ASH Annual Meeting and Exposition, New Orelans, La., December 2009.

latter instance, impurities ordinary associated with the specified material(s). The term "consisting essentially of" limits the scope of a claim to the specified elements, steps or material(s) and those that do not materially affect the basic and novel characteristic(s) of the claimed invention. All of the cysteine protease inhibitors, pharmaceutical compositions comprising such inhibitors and the methods of use thereof which embody the present invention can, in alternate embodiments, be more specifically defined by any of the transitional terms "comprising", "consisting essentially of" and "consisting of".

What is claimed is:

1. A compound of the formula

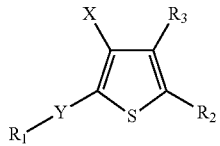

(I)

wherein
X represents nitro or cyano;
Y represents —S— or —O—;
$R_1$ represents substituted aryl or substituted heteroaryl;
$R_2$ represents (i) —CONR$_4$R$_5$, or (ii) —COR$_a$ or —CH(OH)R$_a$, wherein R$_a$ represents an unsubstituted or substituted lower alkyl group;
$R_3$ represents —H, lower alkyl, —NR'R" or an unsubstituted or substituted aryl group wherein R' and R" independently represent —H, unsubstituted or substituted lower alkyl or unsubstituted or substituted phenyl;
$R_4$ and $R_5$ each, independently, represent —H, an unsubstituted or substituted lower alkyl group, an unsubstituted or substituted cycloalkyl group, an unsubstituted or substituted aryl group, an unsubstituted or substituted heteroaryl group, an unsubstituted or substituted heterocycle group, or $R_4$ and $R_5$ together with the nitrogen atom to which they are attached form an unsubstituted or substituted heterocycle group;
$R_6$ represents —H or an unsubstituted or substituted alkyl ($C_1$-$C_6$) group;
said substituted lower alkyl group, and said substituted cycloalky group have 1-3 substituents selected from the group of —NR'R", —OR', oxo, unsubstituted or substituted phenyl, unsubstituted or substituted heteroaryl, unsubstituted or substituted heterocycle, unsubstituted or substituted cycloalkyl, —SR$_6$, —COOR$_6$, —CONR$_{4a}$R$_{5a}$, —SOR$_6$, —SO$_2$R$_6$, wherein R' and R" are as previously defined, and R$_{4a}$ and R$_{5a}$ independently represent —H, unsubstituted or substituted lower alkyl, unsubstituted or substituted cycloalkyl, unsubstituted or substituted heterocycle or R$_{4a}$ and R$_{5a}$ together with the nitrogen atom to which they are attached form an unsubstituted or substituted heterocycle group;
said substituted aryl group, and said substituted phenyl group have 1-5substituents selected from the group of —NO$_2$, unsubstituted or substituted lower alkyl, —NR'R", —SO$_2$R$_6$, halogen, —OR$_6$, heterocycle, —SO$_2$NR'R", —SR$_6$, lower alkanoyl, —NRCOOR$_6$, —NHC(=NH)—NH$_2$, —NHCOR, —C(=NH)—NH$_2$ and —CN;
said substituted heteroaryl group and substituted heterocycle group have 1-5 substituents selected from the group of unsubstituted or substituted lower alkyl, unsubstituted or substituted cycloalkyl, —OR$_6$, —NR'R", —COOR$_6$, lower alkanoyl, oxo, —SO$_2$R$_6$,—C(=NH)—NH$_2$, _NHC(=NH)—NH$_2$, —C(=NH)—NH$_2$ and —CN; and the stereoisomer, pharmaceutically acceptable salt and N-oxide forms of said compound; and
with the proviso that said formula does not include the compounds selected from the group consisting of 1-[5-(2,3-dichlorophenyl)sulfanyl-4-nitro-2-thienyl]ethanone; 1-[5-(4-chlorophenyl)sulfanyl-4-nitro-2-thienyl]ethanone.

2. The compound of claim 1, wherein:
X represents —NO$_2$; Y represents —S—;
$R_1$ represents a halogen-substituted heteroaryl group, or a halogen-substituted aryl group; and $R_2$ represents —CONR$_4$R$_5$, wherein one of $R_4$ or $R_5$ represents —H and the other of $R_4$ and $R_5$ represents a phenyl group substituted with at least one alkoxy, said alkoxy being unsubstituted or substituted, alkylsulfonyl, sulfamoyl, heterocycle or guanidine group; an alkyl-substituted piperidino group; an alkyl-substituted pyrazinyl group or a heteroaryl group selected from the group of quinolinyl, isoquinolinly or a 5-membered heteroaryl group having one or two heteroatoms selected from the group of N, O, S; a substituted heteroaryl, which is a substituted pyridyl group, a substituted isoxazolyl group or a substituted pyrazolyl group, which are substituted by at least one optionally substituted alkyl, cycloalkyl, alkoxy, monoalkylaminoalkyl, dialkylaminoalkyl, dialkylaminoalkylamino group; substituted heterocyclic, which is an alkyl-substituted piperidino group; and substituted heteroarylalkyl, which is an alkyl-substituted pyrazinylalkyl group.

3. The compound of claim 1, selected from the group consisting of:
1-[5-(2-chlorophenyl)sulfanyl-4-nitro-2-thienyl]ethanone;
1-[5-(2,4-dichlorophenyl)sulfanyl-4-nitro-2-thienyl]ethanone;
1-[5-(2,4-difluorophenyl)sulfanyl-4-nitro-2-thienyl]ethanone;
1-[4-nitro-5-[2-(trifluoromethyl)phenyl]sulfanyl-2-thienyl]ethanone;
1-[5-(1-naphthylsulfanyl)-4-nitro-2-thienyl]ethanone;

1-[5-(3-chlorophenyl)sulfanyl-4-nitro-2-thienyl]ethanone;
1-[5-(2,6-dichlorophenyl)sulfanyl-4-nitro-2-thienyl]ethanone;
1-[5-(3,4-dichlorophenyl)sulfanyl-4-nitro-2-thienyl]ethanone;
1-[5-(3,5-dichlorophenyl)sulfanyl-4-nitro-2-thienyl]ethanone;
1-[4-nitro-5-[3-(trifluoromethyl)phenyl]sulfanyl-2-thienyl]ethanone;
1-[5-(2-Naphthylsulfanyl)-4-nitro-2-thienyl]ethanone;
1-[5-(4-bromophenyl)sulfanyl-4-nitro-2-thienyl]ethanone;
1-[4-nitro-5-(4-nitrophenyl)sulfanyl-2-thienyl]ethanone;
1-(4-nitro-5-thiazol-2-ylsulfanyl-2-thienyl)ethanone;
1-[5-(1-methylimidazol-2-yl)sulfanyl-4-nitro-2-thienyl]ethanone;
1-[4-nitro-5-(4-phenylphenyl)sulfanyl-2-thienyl]ethanone;
1-[5-[(3,5-dichloro-4-pyridyl)sulfanyl]-4-nitro-2-thienyl]ethanone;
1-[5-(3,5-dichloro-1-oxido-pyridin-1-ium-4-yl)sulfanyl-4-nitro-2-thienyl]ethanone;
1-[5-(2,3-dichlorophenyl)sulfanyl-4-nitro-2-thienyl]ethanol;
1-[5-(2,4-dichlorophenyl)sulfanyl-4-cyano-2-thienyl]ethanone;
3,5-dichloro-4-[(5-methylsulfonyl-3-nitro-2-thienyl)sulfanyl]pyridine;
2-(2,4-dichlorophenyl)sulfanyl-5-methylsulfonyl-3-nitrothiophene;
1-[5-(2,4-dichlorophenyl)sulfanyl-4-nitro-2-thienyl]-3-dimethylamino-propan-1-one;
1-[5-(2,4-dichlorophenyl)sulfanyl-4-nitro-2-thienyl]-3-dimethylamino-propan-1-ol;
1-[5-(2,4-dichlorophenyl)sulfanyl-4-nitro-2-thienyl]ethanol;
[5-(2,4-dichlorophenyl)sulfanyl-4-nitro-2-thienyl]-(3-nitrophenyl)methanone;
1-[5-(2,4-dichlorophenyl)sulfinyl-4-nitro-2-thienyl]ethanone;
1-[5-(2,4-dichlorophenyl)sulfonyl-4-nitro-2-thienyl]ethanone;
1-[4-nitro-5-(2,3,5,6-tetrafluorophenyl)sulfanyl-2-thienyl]ethanone;
1-(4-nitro-5-quinoxalin-2-ylsulfanyl-2-thienyl)ethanone;
7-[(5-acetyl-3-nitro-2-thienyl)sulfanyl]-4-methylchromen-2-one;
1-[5-[(3-chloro-4-pyridyl)sulfanyl]-4-nitro-2-thienyl]ethanone;
1-[5-[3,5-bis(trifluoromethyl)phenyl]sulfanyl-4-nitro-2-thienyl]ethanone;
5-((2,3-dichlorophenyl)thio)-N-methyl-4-nitrothiophene-2-carboxamide;
5-[(3,5-dichloro-4-pyridyl)sulfanyl]-N-isopropyl-4-nitrothiophene-2-carboxamide;
N-benzyl-5-[(3,5-dichloro-4-pyridyl)sulfanyl]-4-nitrothiophene-2-carboxamide;
5-[(3,5-dichloro-4-pyridyl)sulfanyl]-4-nitro-thiophene-2-carboxamide;
5-[(3,5-dichloro-4-pyridyl)sulfanyl]-N-(2-hydroxyethyl)-4-nitro-thiophene-2-carboxamide;
5-[(3,5-dichloro-4-pyridyl)sulfanyl]-N-(2-dimethylaminoethyl)-4-nitro-thiophene-2-carboxamide;
5-[(3,5-dichloro-4-pyridyl)sulfanyl]-N,N-dimethyl-4-nitro-thiophene-2-carboxamide;
5-((3,5-dichloropyridin-4-yl)thio)-N-(2-(methylthio)ethyl)-4-nitrothiophene-2-carboxamide;
5-((3,5-dichloropyridin-4-yl)thio)-N-(2-methoxybenzyl)-4-nitrothiophene-2-carboxamide;
5-((3,5-dichloropyridin-4-yl)thio)-N-(furan-2-ylmethyl)-4-nitrothiophene-2-carboxamide;
5-((3,5-dichloropyridin-4-yl)thio)-N-(2-methoxyethyl)-4-nitrothiophene-2-carboxamide;
5-((3,5-dichloropyridin-4-yl)thio)-4-nitro-N-(2-phenoxyethyl)thiophene-2-carboxamide;
5-((3,5-dichloropyridin-4-yl)thio)-4-nitro-N-(2-(thiophen-2-yl)ethyl)thiophene-2-carboxamide;
5-((3,5-dichloropyridin-4-yl)thio)-N-((3-methylthiophen-2-yl)methyl)-4-nitrothiophene-2-carboxamide;
N-(3-chlorobenzyl)-5-((3,5-dichloropyridin-4-yl)thio)-4-nitrothiophene-2-carboxamide;
N-([1,1'-biphenyl]-3-ylmethyl)-5-((3,5-dichloropyridin-4-yl)thio)-4-nitrothiophene-2-carboxamide;
5-((3,5-dichloropyridin-4-yl)thio)-N-(2-morpholinoethyl)-4-nitrothiophene-2-carboxamide;
N-(2-chlorobenzyl)-5-((3,5-dichloropyridin-4-yl)thio)-4-nitrothiophene-2-carboxamide;
(5-((3,5-dichloropyridin-4-yl)thio)-4-nitrothiophen-2-yl)(4-(2-hydroxyethyl)piperazin-1-yl)methanone;
tert-butyl 2-(5-((3,5-dichloropyridin-4-yl)thio)-4-nitrothiophene-2-carboxamido)acetate;
N-([1,1'-biphenyl]-4-ylmethyl)-5-((3,5-dichloropyridin-4-yl)thio)-4-nitrothiophene-2-carboxamide;
5-((3,5-dichloropyridin-4-yl)thio)-N-(2-(4-methylpiperazin-1-yl)ethyl)-4-nitrothiophene-2-carboxamide;
5-((3,5-dichloropyridin-4-yl)thio)-N-(3-(4-methylpiperazin-1-yl)propyl)-4-nitrothiophene-2-carboxamide;
(5-((3,5-dichloropyridin-4-yl)thio)-4-nitrothiophen-2-yl)(4-methylpiperazin-1-yl)methanone;
5-((3,5-dichloropyridin-4-yl)thio)-N-(3-methoxybenzyl)-N-methyl-4-nitrothiophene-2-carboxamide;
5-((3,5-dichloropyridin-4-yl)thio)-4-nitro-N-(3-(trifluoromethoxy)benzyl)thiophene-2-carboxamide;
5-((3,5-dichloropyridin-4-yl)thio)-N-(3,5-dimethoxybenzyl)-4-nitrothiophene-2-carboxamide;
5-((3,5-dichloropyridin-4-yl)thio)-N-((2,3-dihydrobenzofuran-5-yl)methyl)-4-nitrothiophene-2-carboxamide;
5-((3,5-dichloropyridin-4-yl)thio)-4-nitro-N-(3-phenyl-1H-pyrazol-5-yl)thiophene-2-carboxamide;
1-(5-((3,5-dichloropyridin-4-yl)thio)-4-nitrothiophene-2-carbonyl)piperidine-4-carboxamide;
(5-((3,5-dichloropyridin-4-yl)thio)-4-nitrothiophen-2-yl)(4-(hydroxymethyl)piperidin-1-yl)methanone;
(5-((3,5-dichloropyridin-4-yl)thio)-4-nitrothiophen-2-yl)(4-fluoropiperidin-1-yl)methanone;
N-((1r,3r,5r,7r)-adamantan-2-yl)-5-((3,5-dichloropyridin-4-yl)thio)-4-nitrothiophene-2-carboxamide;
N-((3s,5s,7s)-adamantan-1-yl)-5-((3,5-dichloropyridin-4-yl)thio)-4-nitrothiophene-2-carboxamide;
5-((3,5-dichloropyridin-4-yl)thio)-N-(4-hydroxycyclohexyl)-4-nitrothiophene-2-carboxamide;
5-((3,5-dichloropyridin-4-yl)thio)-4-nitro-N-(quinolin-8-yl)thiophene-2-carboxamide;
5-((3,5-dichloropyridin-4-yl)thio)-N-(4-(4-methylpiperazin-1-yl)phenyl)-4-nitrothiophene-2-carboxamide;
(5-((3,5-dichloropyridin-4-yl)thio)-4-nitrothiophen-2-yl)(4,4-dimethylpiperidin-1-yl)methanone;
5-((2,4-dichlorophenyl)thio)-N-(1-methylpiperidin-4-yl)-4-nitrothiophene-2-carboxamide;
5-((2,4-dichlorophenyl)thio)-4-nitro-N-(3-(2-oxopyrrolidin-1-yl)propyl)thiophene-2-carboxamide;

(5-((3,5-dichloropyridin-4-yl)thio)-4-nitrothiophen-2-yl)(3-hydroxypiperidin-1-yl)methanone;
N-(2-(1-benzylpyrrolidin-3-yl)ethyl)-5-((3,5-dichloropyridin-4-yl)thio)-4-nitrothiophene-2-carboxamide;
tert-butyl 4-(5-((3,5-dichloropyridin-4-yl)thio)-4-nitrothiophene-2-carboxamido)piperidine-1-carboxylate;
5-((3,5-dichloropyridin-4-yl)thio)-N-(4-(dimethylamino)phenyl)-4-nitrothiophene-2-carboxamide;
5-((3,5-dichloropyridin-4-yl)thio)-N-(4-methylthiazol-2-yl)-4-nitrothiophene-2-carboxamide;
5-((3,5-dichloropyridin-4-yl)thio)-N-(4,5-dimethylthiazol-2-yl)-4-nitrothiophene-2-carboxamide;
5-((3,5-dichloropyridin-4-yl)thio)-N-(5-methylthiazol-2-yl)-4-nitrothiophene-2-carboxamide;
5-((3,5-dichloropyridin-4-yl)thio)-N-((4-hydroxy-1-methylpiperidin-4-yl)methyl)-4-nitrothiophene-2-carboxamide;
5-((3,5-dichloropyridin-4-yl)thio)-N-((1-ethylpyrrolidin-3-yl)methyl)-4-nitrothiophene-2-carboxamide;
5-((3,5-dichloropyridin-4-yl)thio)-N-((3S,4S)-1-ethyl-4-methoxypyrrolidin-3-yl)-4-nitrothiophene-2-carboxamide;
5-((3,5-dichloropyridin-4-yl)thio)-N-(1-(2-methoxyethyl)-5-oxopyrrolidin-3-yl)-4-nitrothiophene-2-carboxamide;
5-((3,5-dichloropyridin-4-yl)thio)-N-(1-methylpyrrolidin-3-yl)-4-nitrothiophene-2-carboxamide;
5-((3,5-dichloropyridin-4-yl)thio)-4-nitro-N-(2-oxopiperidin-3-yl)thiophene-2-carboxamide;
5-((3,5-dichloropyridin-4-yl)thio)-4-nitro-N-phenethylthiophene-2-carboxamide;
5-((3,5-dichloropyridin-4-yl)thio)-N-(2,3-dimethoxybenzyl)-4-nitrothiophene-2-carboxamide;
5-((3,5-dichloropyridin-4-yl)thio)-N-(3,4-dimethoxybenzyl)-4-nitrothiophene-2-carboxamide;
5-((3,5-dichloropyridin-4-yl)thio)-N-(3-methoxybenzyl)-4-nitrothiophene-2-carboxamide;
5-((3,5-dichloropyridin-4-yl)thio)-4-nitro-N-(3-(piperidin-1-yl)propyl)thiophene-2-carboxamide;
5-((3,5-dichloropyridin-4-yl)thio)-4-nitro-N-(pyridin-3-ylmethyl)thiophene-2-carboxamide;
5-((3,5-dichloropyridin-4-yl)thio)-N-(4-(methylsulfonyl)benzyl)-4-nitrothiophene-2-carboxamide;
5-((3,5-dichloropyridin-4-yl)thio)-N-((5-methylpyrazin-2-yl)methyl)-4-nitrothiophene-2-carboxamide;
5-((3,5-dichloropyridin-4-yl)thio)-4-nitro-N-(3-(2-oxopyrrolidin-1-yl)propyl)thiophene-2-carboxamide;
N-(4-bromophenethyl)-5-((3,5-dichloropyridin-4-yl)thio)-4-nitrothiophene-2-carboxamide;
N-(4-chlorobenzyl)-5-((3,5-dichloropyridin-4-yl)thio)-4-nitrothiophene-2-carboxamide;
5-((3,5-dichloropyridin-4-yl)thio)-N-(4-fluorobenzyl)-4-nitrothiophene-2-carboxamide;
5-((3,5-dichloropyridin-4-yl)thio)-4-nitro-N-(2-(pyridin-3-yl)ethyl)thiophene-2-carboxamide;
5-((3,5-dichloropyridin-4-yl)thio)-4-nitro-N-(2-(pyridin-2-yl)ethyl)thiophene-2-carboxamide;
5-((3,5-dichloropyridin-4-yl)thio)-N-isopentyl-4-nitrothiophene-2-carboxamide;
5-(3,5-dichloropyridin-4-yl)thio)-N-(2-fluorophenethyl)-4-nitrothiophene-2-carboxamide;
5-((3,5-dichloropyridin-4-yl)thio)-N-(2,3-dihydro-1H-inden-4-yl)-4-nitrothiophene-2-carboxamide;
5-((3,5-dichloropyridin-4-yl)thio)-N-(2-methoxyphenethyl)-4-nitrothiophene-2-carboxamide;
5-((3,5-dichloropyridin-4-yl)thio)-4-nitro-N-(4-(trifluoromethoxy)benzyl)thiophene-2-carboxamide;
5-((3,5-dichloropyridin-4-yl)thio)-4-nitro-N-(3-(pyridin-2-yl)propyl)thiophene-2-carboxamide;
5-((3,5-dichloropyridin-4-yl)thio)-4-nitro-N-phenylthiophene-2-carboxamide;
N-(2-(4-benzylpiperazin-1-yl)ethyl)-5-((3,5-dichloropyridin-4-yl)thio)-4-nitrothiophene-2-carboxamide;
N-(4-bromobenzyl)-5-((3,5-dichloropyridin-4-yl)thio)-4-nitrothiophene-2-carboxamide;
5-((3,5-dichloropyridin-4-yl)thio)-N-(3-methoxypropyl)-4-nitrothiophene-2-carboxamide;
5-((3,5-dichloropyridin-4-yl)thio)-N-(4-fluorophenethyl)-4-nitrothiophene-2-carboxamide;
5-((3,5-dichloropyridin-4-yl)thio)-N-(4-(dimethylamino)benzyl)-4-nitrothiophene-2-carboxamide;
N-(3-acetamidobenzyl)-5-((3,5-dichloropyridin-4-yl)thio)-4-nitrothiophene-2-carboxamide;
N-(3-cyclopropyl-1H-pyrazol-5-yl)-5-((3,5-dichloropyridin-4-yl)thio)-4-nitrothiophene-2-carboxamide;
N-cyclopropyl-5-((3,5-dichloropyridin-4-yl)thio)-4-nitrothiophene-2-carboxamide;
5-((3,5-dichloropyridin-4-yl)thio)-N-(3-(methylsulfonyl)benzyl)-4-nitrothiophene-2-carboxamide;
5-[(3,5-dichloro-4-pyridyl)sulfanyl]-N-[[3-(3-dimethylaminopropoxy)phenyl]methyl]-4-nitro-thiophene-2-carboxamide;
5-((3,5-dichloropyridin-4-yl)thio)-N-methyl-N-(3-(methylthio)benzyl)-4-nitrothiophene-2-carboxamide;
5-((3,5-dichloropyridin-4-yl)thio)-N-(3-fluorobenzyl)-4-nitrothiophene-2-carboxamide;
5-((3,5-dichloropyridin-4-yl)thio)-N-(4-(methylsulfonyl)phenyl)-4-nitrothiophene-2-carboxamide;
N-(5-chloro-2-methoxyphenyl)-5-((3,5-dichloropyridin-4-yl)thio)-4-nitrothiophene-2-carboxamide;
5-((3,5-dichloropyridin-4-yl)thio)-N-(4-(1-hydroxyethyl)phenyl)-4-nitrothiophene-2-carboxamide;
5-((3,5-dichloropyridin-4-yl)thio)-N-(4-methoxy-2-methylphenyl)-4-nitrothiophene-2-carboxamide;
N-(3-bromophenyl)-5-((3,5-dichloropyridin-4-yl)thio)-4-nitrothiophene-2-carboxamide;
N-(2-chlorophenyl)-5-((3,5-dichloropyridin-4-yl)thio)-4-nitrothiophene-2-carboxamide;
N-(2,6-dichlorophenyl)-5-((3,5-dichloropyridin-4-yl)thio)-4-nitrothiophene-2-carboxamide;
5-((3,5-dichloropyridin-4-yl)thio)-N-(4-fluorophenyl)-4-nitrothiophene-2-carboxamide;
N-(3-chloro-4-fluorophenyl)-5-((3,5-dichloropyridin-4-yl)thio)-4-nitrothiophene-2-carboxamide;
5-((3,5-dichloropyridin-4-yl)thio)-N-(3-fluorophenyl)-4-nitrothiophene-2-carboxamide;
5-((3,5-dichloropyridin-4-yl)thio)-N-(4-fluoro-2-(trifluoromethyl)phenyl)-4-nitrothiophene-2-carboxamide;
5-((3,5-dichloropyridin-4-yl)thio)-N-(4-fluoro-3-(trifluoromethyl)phenyl)-4-nitrothiophene-2-carboxamide;
N-(2,4-dichlorophenyl)-5-((3,5-dichloropyridin-4-yl)thio)-4-nitrothiophene-2-carboxamide;
N-(3-chlorophenyl)-5-((3,5-dichloropyridin-4-yl)thio)-4-nitrothiophene-2-carboxamide;
5-((3,5-dichloropyridin-4-yl)thio)-N-(2,4-difluorophenyl)-4-nitrothiophene-2-carboxamide;
5-((3,5-dichloropyridin-4-yl)thio)-N-(3-fluoro-2-methylphenyl)-4-nitrothiophene-2-carboxamide;
5-((3,5-dichloropyridin-4-yl)thio)-N-(3-(difluoromethoxy)benzyl)-4-nitrothiophene-2-carboxamide;
5-((3,5-dichloropyridin-4-yl)thio)-N-(3-(dimethylamino)benzyl)-4-nitrothiophene-2-carboxamide;

5-((3,5-dichloropyridin-4-yl)thio)-N-((2,3-dihydrobenzo[b][1,4]dioxin-6-yl)methyl)-4-nitrothiophene-2-carboxamide;
5-((3,5-dichloropyridin-4-yl)thio)-4-nitro-N-(3-(trifluoromethyl)benzyl)thiophene-2-carboxamide;
5-((3,5-dichloropyridin-4-yl)thio)-N-(3-ethoxybenzyl)-4-nitrothiophene-2-carboxamide;
5-((3,5-dichloropyridin-4-yl)thio)-N-(3-methylbenzyl)-4-nitrothiophene-2-carboxamide;
N-(benzo[d][1,3]dioxol-5-ylmethyl)-5-((3,5-dichloropyridin-4-yl)thio)-4-nitrothiophene-2-carboxamide;
N-(4-bromophenyl)-5-((3,5-dichloropyridin-4-yl)thio)-4-nitrothiophene-2-carboxamide;
N-(tert-butyl)-5-((3,5-dichloropyridin-4-yl)thio)-4-nitrothiophene-2-carboxamide;
N-cyclohexyl-5-((3,5-dichloropyridin-4-yl)thio)-4-nitrothiophene-2-carboxamide;
5-((3,5-dichloropyridin-4-yl)thio)-N-(4-methoxyphenyl)-4-nitrothiophene-2-carboxamide;
5-((3,5-dichloropyridin-4-yl)thio)-N-(3-methoxyphenyl)-4-nitrothiophene-2-carboxamide;
5-((3,5-dichloropyridin-4-yl)thio)-N-(4-morpholinophenyl)-4-nitrothiophene-2-carboxamide;
N-(benzo[d][1,3]dioxol-1-5-yl)-5-((3,5-dichloropyridin-4-yl)thio)-4-nitrothiophene-2-carboxamide;
5-((3,5-dichloropyridin-4-yl)thio)-N-(2,5-difluorophenyl)-4-nitrothiophene-2-carboxamide;
5-((3,5-dichloropyridin-4-yl)thio)-4-nitro-N-(4-sulfamoylphenyl)thiophene-2-carboxamide;
5-((3,5-dichloropyridin-4-yl)thio)-4-nitro-N-(2-(piperidin-1-yl)ethyl)thiophene-2-carboxamide;
N-((6-chloropyridin-3-yl)methyl)-5-((3,5-dichloropyridin-4-yl)thio)-4-nitrothiophene-2-carboxamide;
methyl 4-((5-((3,5-dichloropyridin-4-yl)thio)-4-nitrothiophene-2-carboxamido)methyl)benzoate;
5-((3,5-dichloropyridin-4-yl)thio)-4-nitro-N-(3-(trifluoromethyl)-1H-pyrazol-5-yl)thiophene-2-carboxamide;
5-((3,5-dichloropyridin-4-yl)thio)-N-(4-hydroxybenzyl)-4-nitrothiophene-2-carboxamide;
5-[(3,5-dichloro-4-pyridyl)sulfanyl]-N-(1-ethyltriazol-4-yl)-4-nitro-thiophene-2-carboxamide;
5-((3,5-dichloropyridin-4-yl)thio)-N-(1-methyl-1H-pyrazol-5-yl)-4-nitrothiophene-2-carboxamide;
5-((3,5-dichloropyridin-4-yl)thio)-N-(1-methylpiperidin-4-yl)-4-nitrothiophene-2-carboxamide;
5-((3,5-dichloropyridin-4-yl)thio)-4-nitro-N-(3,4,5-trimethoxyphenyl)thiophene-2-carboxamide;
5-((3,5-dichloropyridin-4-yl)thio)-N-(3,4-dimethoxyphenyl)-4-nitrothiophene-2-carboxamide;
5-((3,5-dichloropyridin-4-yl)thio)-N-(isoxazol-3-yl)-4-nitrothiophene-2-carboxamide;
5-((3,5-dichloropyridin-4-yl)thio)-4-nitro-N-(thiazol-2-yl)thiophene-2-carboxamide;
5-((3,5-dichloropyridin-4-yl)thio)-4-nitro-N-(quinolin-3-yl)thiophene-2-carboxamide;
5-((3,5-dichloropyridin-4-yl)thio)-N-(4-(methylthio)phenyl)-4-nitrothiophene-2-carboxamide;
5-((3,5-dichloropyridin-4-yl)thio)-N-(6-methoxypyridin-3-yl)-4-nitrothiophene-2-carboxamide;
5-((3,5-dichloropyridin-4-yl)thio)-N-((1r,3s,5R,7S)-3-hydroxyadamantan-1-yl)-4-nitrothiophene-2-carboxamide;
N-(bicyclo[2.2.1]heptan-2-yl)-5-((3,5-dichloropyridin-4-yl)thio)-4-nitrothiophene-2-carboxamide;
5-((3,5-dichloropyridin-4-yl)thio)-4-nitro-N-(2,2,6,6-tetramethylpiperidin-4-yl)thiophene-2-carboxamide;
5-((3,5-dichloropyridin-4-yl)thio)-N-(isoquinolin-5-yl)-4-nitrothiophene-2-carboxamide;
5-((3,5-dichloropyridin-4-yl)thio)-4-nitro-N-(quinolin-6-yl)thiophene-2-carboxamide;
5-((3,5-dichloropyridin-4-yl)thio)-N-(4-hydroxyphenyl)-4-nitrothiophene-2-carboxamide;
5-((3,5-dichloropyridin-4-yl)thio)-N-(1-(2-(dimethylamino)ethyl)-3-methyl-1H-pyrazol-5-yl)-4-nitrothiophene-2-carboxamide;
N-(4-acetylphenyl)-5-((3,5-dichloropyridin-4-yl)thio)-4-nitrothiophene-2-carboxamide;
5-((3,5-dichloropyridin-4-yl)thio)-N-(8-methyl-8-azabicyclo[3.2.1]octan-3-yl)-4-nitrothiophene-2-carboxamide;
5-((3,5-dichloropyridin-4-yl)thio)-N-(2-(1-ethylpiperidin-4-yl)ethyl)-4-nitrothiophene-2-carboxamide;
5-((3,5-dichloropyridin-4-yl)thio)-N-(1-ethyl-1H-1,2,4-triazol-3-yl)-4-nitrothiophene-2-carboxamide;
5-((3,5-dichloropyridin-4-yl)thio)-N-(1-isopropylpiperidin-4-yl)-4-nitrothiophene-2-carboxamide;
5-((3,5-dichloropyridin-4-yl)thio)-4-nitro-N-(1,2,2,6,6-pentamethylpiperidin-4-yl)thiophene-2-carboxamide;
5-((3,5-dichloropyridin-4-yl)thio)-N-(1-methylpiperidin-3-yl)-4-nitrothiophene-2-carboxamide;
5-((3,5-dichloropyridin-4-yl)thio)-N-((1-methylpiperidin-4-yl)methyl)-4-nitrothiophene-2-carboxamide;
5-((3,5-dichloropyridin-4-yl)thio)-4-nitro-N-(3-(pyrrolidin-1-yl)propyl)thiophene-2-carboxamide;
5-((3,5-dichloropyridin-4-yl)thio)-N-(4-(2-(dimethylamino)ethoxy)phenyl)-4-nitrothiophene-2-carboxamide;
5-[(3,5-dichloro-4-pyridyl)sulfanyl]-N-[4-(3-dimethylaminopropoxy)phenyl]-4-nitro-thiophene-2-carboxamide;
5-((3,5-dichloropyridin-4-yl)thio)-N-(3-(methylthio)propyl)-4-nitrothiophene-2-carboxamide;
5-((3,5-dichloropyridin-4-yl)thio)-4-nitro-N-(pyrrolidin-3-yl)thiophene-2-carboxamide;
5-((3,5-dichloropyridin-4-yl)thio)-4-nitro-N-(piperidin-4-yl)thiophene-2-carboxamide;
5-((3,5-dichloropyridin-4-yl)thio)-N-(1-ethylpyrrolidin-3-yl)-4-nitrothiophene-2-carboxamide;
N-(1-cyclopropylpyrrolidin-3-yl)-5-((3,5-dichloropyridin-4-yl)thio)-4-nitrothiophene-2-carboxamide;
N-(1-acetylpyrrolidin-3-yl)-5-((3,5-dichloropyridin-4-yl)thio)-4-nitrothiophene-2-carboxamide;
5-((3,5-dichloropyridin-4-yl)thio)-N-(3-(dimethylamino)-1-phenylpropyl)-4-nitrothiophene-2-carboxamide;
N-(5-(tert-butyl)isoxazol-3-yl)-5-((3,5-dichloropyridin-4-yl)thio)-4-nitrothiophene-2-carboxamide;
5-((3,5-dichloropyridin-4-yl)thio)-4-nitro-N-(quinuclidin-3-yl)thiophene-2-carboxamide;
4-cyano-5-((3,5-dichloropyridin-4-yl)thio)-N-(1-methylpiperidin-4-yl)thiophene-2-carboxamide;
4-cyano-5-((3,5-dichloropyridin-4-yl)thio)-N-(4-(3-(dimethylamino)propoxy)phenyl)thiophene-2-carboxamide;
4-cyano-5-((3,5-dichloropyridin-4-yl)thio)-N-(4-(3-(dimethylamino)propoxy)-3-methoxyphenyl)thiophene-2-carboxamide;
4-cyano-5-((3,5-dichloropyridin-4-yl)thio)-N-(3-(3-(dimethylamino)propoxy)benzyl)thiophene-2-carboxamide;
4-cyano-5-((3,5-dichloropyridin-4-yl)thio)-N-(quinolin-3-yl)thiophene-2-carboxamide;

4-cyano-5-((3,5-dichloropyridin-4-yl)thio)-N-(4-(methylsulfonyl)phenyl)thiophene-2-carboxamide;
ethyl 2-(5-((3,5-dichloropyridin-4-yl)thio)-4-nitrothiophene-2-carboxamido)acetate;
2-(5-((3,5-dichloropyridin-4-yl)thio)-4-nitrothiophene-2-carboxamido)acetic acid;
5-((3,5-dichloropyridin-4-yl)thio)-N-(2-(4-hydroxypiperidin-1-yl)-2-oxoethyl)-4-nitrothiophene-2-carboxamide;
5-((3,5-dichloropyridin-4-yl)thio)-N-(2-(3-hydroxypiperidin-1-yl)-2-oxoethyl)-4-nitrothiophene-2-carboxamide;
5-((3,5-dichloropyridin-4-yl)thio)-N-(2-((3-methoxypropyl)amino)-2-oxoethyl)-4-nitrothiophene-2-carboxamide;
5-((3,5-dichloropyridin-4-yl)thio)-N-(2-((2-methoxyethyl)amino)-2-oxoethyl)-4-nitrothiophene-2-carboxamide;
5-((3,5-dichloropyridin-4-yl)thio)-N-(2-(4-(hydroxymethyl)piperidin-1-yl)-2-oxoethyl)-4-nitrothiophene-2-carboxamide;
5-((3,5-dichloropyridin-4-yl)thio)-N-(2-(4-fluoropiperidin-1-yl)-2-oxoethyl)-4-nitrothiophene-2-carboxamide;
5-((3,5-dichloropyridin-4-yl)thio)-N-(2-((2-(dimethylamino)ethyl)amino)-2-oxoethyl)-4-nitrothiophene-2-carboxamide;
5-((3,5-dichloropyridin-4-yl)thio)-N-(2-(4-methylpiperazin-1-yl)-2-oxoethyl)-4-nitrothiophene-2-carboxamide;
5-((3,5-dichloropyridin-4-yl)thio)-N-(2-((2,2-difluoroethyl)amino)-2-oxoethyl)-4-nitrothiophene-2-carboxamide;
N-(2-(cyclohexylamino)-2-oxoethyl)-5-((3,5-dichloropyridin-4-yl)thio)-4-nitrothiophene-2-carboxamide;
5-((3,5-dichloropyridin-4-yl)thio)-4-nitro-N-(2-oxo-2-(piperidin-1-yl)ethyl)thiophene-2-carboxamide;
5-((3,5-dichloropyridin-4-yl)thio)-N-(2-((1-methylpiperidin-4-yl)amino)-2-oxoethyl)-4-nitrothiophene-2-carboxamide;
5-((3,5-dichloropyridin-4-yl)thio)-N-(3-(3-hydroxypiperidin-1-yl)propyl)-4-nitrothiophene-2-carboxamide;
5-((3,5-dichloropyridin-4-yl)thio)-N-(3-(4-(dimethylamino)piperidin-1-yl)propyl)-4-nitrothiophene-2-carboxamide;
5-((3,5-dichloropyridin-4-yl)thio)-N-(3-(4-hydroxypiperidin-1-yl)propyl)-4-nitrothiophene-2-carboxamide;
1-(3-(5-((3,5-dichloropyridin-4-yl)thio)-4-nitrothiophene-2-carboxamido)propyl) piperidine-4-carboxamide;
5-((3,5-dichloropyridin-4-yl)thio)-N-(3-(4-(hydroxymethyl)piperidin-1-yl)propyl)-4-nitrothiophene-2-carboxamide;
5-((3,5-dichloropyridin-4-yl)thio)-N-(3-(4-fluoropiperidin-1-yl)propyl)-4-nitrothiophene-2-carboxamide;
5-((3,5-dichloropyridin-4-yl)thio)-N-(3-(4,4-dimethylpiperidin-1-yl)propyl)-4-nitrothiophene-2-carboxamide;
5-((3,5-dichloropyridin-4-yl)thio)-4-nitro-N-(1-propylpiperidin-4-yl)thiophene-2-carboxamide;
N-(1-cyclopropylpiperidin-4-yl)-5-(3,5-dichloropyridin-4-yl)thio)-4-nitrothiophene-2-carboxamide;
N-(1-acetylpiperidin-4-yl)-5-((3,5-dichloropyridin-4-yl)thio)-4-nitrothiophene-2-carboxamide;
5-((3,5-dichloropyridin-4-yl)thio)-N-(1-(methylsulfonyl)piperidin-4-yl)-4-nitrothiophene-2-carboxamide;
tert-butyl (4-(5-((3,5-dichloropyridin-4-yl)thio)-4-nitrothiophene-2-carboxamido)phenyl)carbamate;
N-(4-aminophenyl)-5-((3,5-dichloropyridin-4-yl)thio)-4-nitrothiophene-2-carboxamide;
5-((3,5-dichloropyridin-4-yl)thio)-N-(4-guanidinophenyl)-4-nitrothiophene-2-carboxamide;
N-(1-carbamimidoylpiperidin-4-yl)-5-((3,5-dichloropyridin-4-yl)thio)-4-nitrothiophene-2-carboxamide;
5-((3,5-dichloropyridin-4-yl)thio)-N-(6-((2-(dimethylamino)ethyl)amino)pyridin-3-yl)-4-nitrothiophene-2-carboxamide;
5-((3,5-dichloropyridin-4-yl)thio)-N-((5-methoxypyridin-3-yl)methyl)-4-nitrothiophene-2-carboxamide;
5-((3,5-dichloropyridin-4-yl)thio)-N-(4-(3-(dimethylamino)propoxy)-3-methoxyphenyl)-4-nitrothiophene-2-carboxamide;
5-((3,5-dichloropyridin-4-yl)thio)-N-(2-hydroxy-3-(piperidin-1-yl)propyl)-4-nitrothiophene-2-carboxamide;
3,5-dichloro-4-((5-((1-methylpiperidin-4-yl)carbamoyl)-3-nitrothiophen-2-yl)thio)pyridine-1-oxide;
5-((3,5-dichloro-2,6-dimethylpyridin-4-yl)thio)-N-(1-methylpiperidin-4-yl)-4-nitrothiophene-2-carboxamide;
5-((3,5-dichloropyridin-4-yl)thio)-N-(3-(methylsulfinyl)propyl)-4-nitrothiophene-2-carboxamide;
5-((3,5-dichloropyridin-4-yl)thio)-N-(3-(methylsulfonyl)propyl)-4-nitrothiophene-2-carboxamide;
4-cyano-5-((3,5-dichloropyridin-4-yl)thio)-N-(1-methylpiperidin-4-yl)-3-phenylthiophene-2-carboxamide;
5-((2,4-dichlorophenyl)thio)-4-nitro-N-(3-(piperidin-1-yl)propyl)thiophene-2-carboxamide;
methyl 5-((benzo[d]thiazol-2-yl)thio)-4-nitrothiophene-2-carboxylate;
5-((benzo[d]thiazol-2-yl)thio)-N-benzyl-4-nitrothiophene-2-carboxamide;
5-((benzo[d]thiazol-1-2-yl)thio)-N-(1-isopropylpiperidin-4-yl)-4-nitrothiophene-2-carboxamide;
5-((benzo[d]thiazol-2-yl)thio)-N-(3-(dimethylamino)-1-phenylpropyl)-4-nitrothiophene-2-carboxamide;
methyl 5-((3,5-difluoropyridin-4-yl)thio)-4-nitrothiophene-2-carboxylate;
5-((3,5-difluoropyridin-4-yl)thio)-N-(1-methylpiperidin-4-yl)-4-nitrothiophene-2-carboxamide;
5-((3,5-difluoropyridin-4-yl)thio)-N-(4-(3-(dimethylamino)propoxy)phenyl)-4-nitrothiophene-2-carboxamide;
methyl 5-((3,5-dichloropyridin-4-yl)oxy)-4-nitrothiophene-2-carboxylate;
5-((3,5-dichloropyridin-4-yl)oxy)-N-(1-methylpiperidin-4-yl)-4-nitrothiophene-2-carboxamide;
5-((3,5-dichloropyridin-4-yl)oxy)-N-(1-isopropylpiperidin-4-yl)-4-nitrothiophene-2-carboxamide;
5-(2,6-dichlorophenoxy)-N-(1-methylpiperidin-4-yl)-4-nitrothiophene-2-carboxamide;
5-((3,5-dichloropyridin-4-yl)thio)-N-(1-ethylpiperidin-4-yl)-4-nitrothiophene-2-carboxamide;
5-((3,5-dichloropyridin-4-yl)thio)-N-(3-isopropyl-1H-pyrazol-5-yl)-4-nitrothiophene-2-carboxamide;
5-((3,5-dichloropyridin-4-yl)thio)-N-(4-(methylthio)benzyl)-4-nitrothiophene-2-carboxamide;
methyl 5-((5-chloro-6-fluoro-1H-benzo[d]imidazol-2-yl)thio)-4-nitrothiophene-2-carboxylate;
methyl 5-((5,7-dimethyl-[1,2,4]triazolo[1,5-a]pyrimidin-2-yl)thio)-4-nitrothiophene-2-carboxylate;
5-((2,4-difluorophenyl)thio)-4-nitro-N-(3-(piperidin-1-yl)propyl)thiophene-2-carboxamide;
5-((3,5-dichloropyridin-4-yl)thio)-4-nitro-N-(3-oxo-3-(pyrrolidin-1-yl)propyl)thiophene-2-carboxamide;

5-((2,6-dichlorophenyl)thio)-N-(1-methylpiperidin-4-yl)-4-nitrothiophene-2-carboxamide;

1-(5-(2,4-dichlorophenoxy)-4-nitrothiophen-2-yl)ethanone;

1-(5-((4-chloro-2,3,5,6-tetrafluorophenyl)thio)-4-nitrothiophen-2-yl)ethanone.

4. The compound of claim 1 selected from the group consisting of:

5-((3,5-dichloropyridin-4-yl)thio)-N-((5-methylpyrazin-2-yl)methyl)-4-nitrothiophene-2-carboxamide;

N-(3-cyclopropyl-1H-pyrazol-5-yl)-5-((3,5-dichloropyridin-4-yl)thio)-4-nitrothiophene-2-carboxamide;

5-((3,5-dichloropyridin-4-yl)thio)-N-(4-(methylsulfonyl)phenyl)-4-nitrothiophene-2-carboxamide;

5-((3,5-dichloropyridin-4-yl)thio)-N-(4-methoxyphenyl)-4-nitrothiophene-2-carboxamide;

5-((3,5-dichloropyridin-4-yl)thio)-N-(4-morpholinophenyl)-4-nitrothiophene-2-carboxamide;

5-((3,5-dichloropyridin-4-yl)thio)-4-nitro-N-(4-sulfamoylphenyl)thiophene-2-carboxamide;

5-((3,5-dichloropyridin-4-yl)thio)-N-(1-methylpiperidin-4-yl)-4-nitrothiophene-2-carboxamide;

5-((3,5-dichloropyridin-4-yl)thio)-N-(isoxazol-3-yl)-4-nitrothiophene-2-carboxamide;

5-((3,5-dichloropyridin-4-yl)thio)-4-nitro-N-(thiazol-2-yl)thiophene-2-carboxamide;

5-((3,5-dichloropyridin-4-yl)thio)-4-nitro-N-(quinolin-3-yl)thiophene-2-carboxamide;

5-((3,5-dichloropyridin-4-yl)thio)-N-(6-methoxypyridin-3-yl)-4-nitrothiophene-2-carboxamide;

5-((3,5-dichloropyridin-4-yl)thio)-N-(isoquinolin-5-yl)-4-nitrothiophene-2-carboxamide;

5-((3,5-dichloropyridin-4-yl)thio)-4-nitro-N-(quinolin-6-yl)thiophene-2-carboxamide;

5-((3,5-dichloropyridin-4-yl)thio)-N-(1-(2-(dimethylamino)ethyl)-3-methyl-1H-pyrazol-5-yl)-4-nitrothiophene-2-carboxamide;

5-((3,5-dichloropyridin-4-yl)thio)-4-nitro-N-(1,2,2,6,6-pentamethylpiperidin-4-yl)thiophene-2-carboxamide;

5-((3,5-dichloropyridin-4-yl)thio)-N-(4-(2-(dimethylamino)ethoxy)phenyl)-4-nitrothiophene-2-carboxamide;

5-((3,5-dichloropyridin-4-yl)thio)-N-(4-(3-(dimethylamino)propoxy)phenyl)-4-nitrothiophene-2-carboxamide;

4-cyano-5-((3,5-dichloropyridin-4-yl)thio)-N-(4-(3-(dimethylamino)propoxy) phenyl)thiophene-2-carboxamide;

N-(5-(tert-butyl)isoxazol-3-yl)-5-((3,5-dichloropyridin-4-yl)thio)-4-nitrothiophene-2-carboxamide;

5-((3,5-dichloropyridin-4-yl)thio)-N-(4-guanidinophenyl)-4-nitrothiophene-2-carboxamide;

5-((3,5-dichloropyridin-4-yl)thio)-N-(6-((2-(dimethylamino)ethyl) amino)pyridin-3-yl)-4-nitrothiophene-2-carboxamide;

4-cyano-5-((3,5-dichloropyridin-4-yl)thio)-N-(4-(3-(dimethylamino)propoxy)-3-methoxyphenyl)thiophene-2-carboxamide;

4-cyano-5-((3,5-dichloropyridin-4-yl)thio)-N-(quinolin-3-yl)thiophene-2-carboxamide; and 4-cyano-5-((3,5-dichloropyridin-4-yl)thio)-N-(4-(methylsulfonyl)phenyl)thiophene-2-carboxamide.

5. A compound of claim 1 selected from the group consisting of:

1-(5-((2,4-dichlorophenyl)thio)-4-nitrothiophen-2-yl)-3-(dimethylamino)propan-1-one;

1-(5-((2,4-dichlorophenyl)thio)-4-nitrothiophen-2-yl)-3-(dimethylamino)propan-1-ol;

1-(5-(2,4-dichlorophenoxy)-4-nitrothiophen-2-yl)ethanone;

1-(5-((3,5-dichlorophenyl)thio)-4-nitrothiophen-2-yl)ethanone;

1-(5-((3,4-dichlorophenyl)thio)-4-nitrothiophen-2-yl)ethanone;

1-(5-((2,4-dichlorophenyl)thio)-4-nitrothiophen-2-yl)ethanone;

1-(5-((2,6-dichlorophenyl)thio)-4-nitrothiophen-2-yl)ethanone;

5-acetyl-2-((2,4-dichlorophenyl)thio)thiophene-3-carbonitrile;

1-(5-((2,4-dichlorophenyl)amino)-4-nitrothiophen-2-yl)ethanone; and 1-(5-((3,5-dichloropyridin-4-yl)thio)-4-nitrothiophen-2-yl)ethanone.

6. The compound of claim 1 selected from the group consisting of:

N-(3-cyclopropyl-1H-pyrazol-5-yl)-5-((3,5-dichloropyridin-4-yl)thio)-4-nitrothiophene-2-carboxamide;

5-((3,5-dichloropyridin-4-yl)thio)-N-(4-(methylsulfonyl)phenyl)-4-nitrothiophene-2-carboxamide;

5-((3,5-dichloropyridin-4-yl)thio)-N-(4-methoxyphenyl)-4-nitrothiophene-2-carboxamide;

5-((3,5-dichloropyridin-4-yl)thio)-4-nitro-N-(quinolin-3-yl)thiophene-2-carboxamide;

5-((3,5-dichloropyridin-4-yl)thio)-N-(4-(3-(dimethylamino)propoxy)phenyl)-4-nitrothiophene-2-carboxamide; and 5-((3,5-dichloropyridin-4-yl)thio)-N-(4-guanidinophenyl)-4-nitrothiophene-2-carboxamide.

7. A pharmaceutical composition comprising at least one compound of claim 1 together with a pharmaceutically acceptable excipient, carrier or diluent.

8. A method of inhibiting cysteine protease activity of a deubiquitylating enzyme in a subject, comprising administering to said subject an effective amount of a compound as claimed in claim 1.

9. A method according to claim 8 wherein the deubiquitylating enzyme is USP7.

10. A method of inhibiting USP7 in a subject, comprising administering to said subject an effective amount of at least one compound as claimed in claim 1.

11. The compound of claim 1, wherein:

X represents —NO$_2$;

Y represents —S—;

R$_1$ represents a halogen-substituted heteroaryl group, or a halogen-substituted aryl group; and R$_2$ represents —CONR$_4$R$_5$, wherein one of R$_4$ or R$_5$ represents —H and the other of R$_4$ and R$_5$ represents a phenyl or benzyl group substituted with at least one alkoxy, said alkoxy being unsubstituted or substituted, alkylsulfonyl, sulfamoyl, halogen, heterocycle or guanidine group; an unsubstituted or alkyl-substituted piperidino group; an unsubstituted or alkyl-substituted pyrazinyl group or a heteroaryl group selected from the group of quinolinyl, isoquinolinly or a 5-membered heteroaryl group having one to three heteroatoms selected from the group of N, O, S; an unsubstituted or substituted heteroaryl, which is an unsubstituted or substituted pyridyl group, an unsubstitued or substituted isoxazolyl group or an unsubstituted or substituted pyrazolyl group, said substituents being at least one optionally substituted alkyl, cycloalkyl, alkoxy, monoalkylaminoalkyl, dialkylaminoalkyl, dialkylaminoalkylamino group; substituted heterocyclic, which is an alkyl-substituted piperidino group; and substituted heteroarylalkyl, which is an alkyl-substituted pyrazinylalkyl group.

12. The compound 1-[5-[(2,4-difluorophenyl)thio]-4-nitro-2-thienyl]-ethanone.

* * * * *

UNITED STATES PATENT AND TRADEMARK OFFICE
CERTIFICATE OF CORRECTION

PATENT NO.        : 8,680,139 B2
APPLICATION NO. : 13/262422
DATED             : March 25, 2014
INVENTOR(S)       : Cao et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 5 days.

Signed and Sealed this
Twenty-ninth Day of September, 2015

Michelle K. Lee
*Director of the United States Patent and Trademark Office*

SEQUENCE LISTING

<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: 6x histidine tag

<400> SEQUENCE: 1

His His His His His His
1               5